(12) United States Patent
Small et al.

(10) Patent No.: US 7,041,810 B2
(45) Date of Patent: May 9, 2006

(54) ALPHA-2 ADRENERGIC RECEPTOR POLYMORPHISMS

(75) Inventors: Kersten M. Small, Cincinnati, OH (US); Stephen B. Liggett, Cincinnati, OH (US)

(73) Assignee: University Of Cincinnati, Cincinnati, OH (US)

( * ) Notice: Subject to any disclaimer, the term of this patent is extended or adjusted under 35 U.S.C. 154(b) by 624 days.

(21) Appl. No.: 10/001,073

(22) Filed: Nov. 1, 2001

(65) Prior Publication Data

US 2003/0113725 A1 Jun. 19, 2003

Related U.S. Application Data

(63) Continuation-in-part of application No. 09/551,744, filed on Apr. 17, 2000, now abandoned, and a continuation-in-part of application No. 09/636,259, filed on Aug. 10, 2000, now abandoned, and a continuation-in-part of application No. 09/692,077, filed on Oct. 19, 2000, and a continuation-in-part of application No. PCT/US01/12575, filed on Apr. 17, 2001.

(51) Int. Cl.
*C07H 21/04* (2006.01)

(52) U.S. Cl. .................. 536/23.1; 536/24.3; 536/24.32; 536/24.33

(58) Field of Classification Search ................ 536/23.1, 536/24.3, 24.32, 24.33; 435/6, 91.1, 91.2
See application file for complete search history.

(56) References Cited

U.S. PATENT DOCUMENTS

| | | | |
|---|---|---|---|
| 5,595,880 A | 1/1997 | Weinshank et al. |
| 5,648,482 A | 7/1997 | Meyer |
| 5,846,710 A | 12/1998 | Bajaj |
| 5,856,092 A | 1/1999 | Dale |
| 5,888,819 A | 3/1999 | Goelet |
| 5,981,174 A | 11/1999 | Wolf |
| 6,004,744 A | 12/1999 | Goelet |
| 6,013,431 A | 1/2000 | Soderlund |
| 6,156,503 A | 12/2000 | Drazen |

FOREIGN PATENT DOCUMENTS

| | | |
|---|---|---|
| EP | 0 874 048 A2 * | 10/1998 |
| JP | 06121686 | 5/1994 |
| WO | WO 95/33048 | 12/1995 |
| WO | PCT/US98/21227 | 10/1998 |
| WO | PCT/US99/27963 | 11/1999 |
| WO | WO 00/20450 | 4/2000 |
| WO | WO 01/29082 | 4/2001 |

OTHER PUBLICATIONS

Heinonen P. et al: "Identification of a three–amino acid deletion in the alpha2B–adrenergic receptor that is associated with reduced basal metabolic rate in obese subjects." *The Journal of Clinical Endocrinology and Metabolism*, United States, Jul. 1999, vol. 84, No. 7, pp. 2429–2433.

Baldwin C.T., et al: "Identification of a polymorphic glutamic acid stretch in the alpha2B–adrenergic receptor and lack of linkage with essential hypertension." *American Journal of Hypertension: Journal of the American Society of Hypertension*, United States, Sep. 1999, vol. 12, No. 9, Pt. 1, pp. 853–857.

Jewell–Motz, E.A. et al: "An acidic motif within the third intracellular loop of the alpha2C2 adrenergic receptor is required for agonist–promoted phosphorylation and desensitization." *Biochemistry*, United States Sep. 19, 1995, vol. 34, No. 37, Sep. 19, 1995, pp. 11946–11953.

Comings, D.E., et al: "Additive effect of three noradrenergic genes (ADRA2a, ADRA2C, DBH) on attention–deficit hyperactivity disorder and learning disabilities in Tourette syndrome subjects." *Clinical Genetics*, Denmark, Mar. 1999, vol. 55, No. 3, pp. 160–172.

Makaritsis K.P., et al: "Role of the alpha2B–adrenergic receptor in the development of salt–induced hypertension." *Hypertension*. United States, Jan. 1999, vol. 33, No. 1, Jan. 1999, pp. 14–17.

Michel M.C., et al: "Functional correlates of alpha(2A)–adrenoceptor gene polymorphism in the HANE study." *Nephrology, Dialysis, Transplantation: Official Publication of the European Dialysis and Transplant Association–European Renal Association*. England, Nov. 1999, vol. 14, No. 11, pp. 2657–2663.

Freeman K., et al: "Genetic polymorphism of the alpha 2–adrenergic receptor is associated with increased platelet aggregation, baroreceptor sensitivity, and salt excretion in normotensive humans." *American Journal of Hypertension: Journal of the American Society of Hypertension*. United States, Sep. 1995, vol. 8, No. 9, pp. 863–869.

Small K.M., et al: "Polymorphic deletion of three intracellular acidic residues of the alpha 2B–adrenergic receptor decreases G protein–coupled receptor kinase–mediated phosphorylation and desensitization." *The Journal of Biological Chemistry*. United States, Feb. 16, 2001, vol. 276, No. 7, pp. 4917–4922.

(Continued)

*Primary Examiner*—Kenneth R. Horlick
*Assistant Examiner*—Cynthia Wilder
(74) *Attorney, Agent, or Firm*—Dinsmore & Shohl LLP

(57) ABSTRACT

The present invention includes polymorphisms in nucleic acids encoding the alpha-2B, alpha-2A, and alpha-2C adrenergic receptor and expressed alpha-2B, alpha-2A and alpha-2C adrenergic receptor molecule. The invention also pertains to methods and molecules for detecting such polymorphisms. The invention further pertains to the use of such molecules and methods in the diagnosis, prognosis, and treatment of diseases such as cardiovascular and central nervous system disease.

4 Claims, 15 Drawing Sheets

OTHER PUBLICATIONS

Snapir A., et al: "An insertion/deletion polymorphism in the alpha2B–adrenergic receptor gene is a novel genetic risk factor for acute coronary events." *Journal of the American College of Cardiology*. United States, May 2001, vol. 37, No. 6, pp. 1516–1522.

Ruffolo, R.R., Jr., Nichols, A.J., Stadel, J.M., and Hieble, J.P. (1993) Annu Rev Pharmacol Toxicol 32, 243–279.

Sallinen, J., Link, R.E., Haapalinna, A., Viitamaa, T., Kulatunga, M., Kobilka, B.K., Macdonald, E., Pelto–Huikko, M., Leino, T., Barsh, G.S., and Scheinin, M. (1997) Mol.Pharmacol. 51, 36–46.

Sallinen, J., Haapalinna, A., Viitamaa, T., Kobika, B.K., and Scheinin, M. (1998) The Journal of Neuroscience 18, 3035–3042.

Tanila, H., Mustonen, K., Sallinen, J., Scheinin, M., and Riekkinen, P., Jr. (1999) European Journal of Neuroscience 11, 599–603.

Bjorklund, M., Sirvio, J., Puolivali, J., Sallinen, J., Jakala, P., Scheinin, M., Kobilka, B.K., and Riekkinen, P., Jr. (1998) Mol Pharmacol 54, 569–576.

Kobilka, B.K., Matsui, H., kobilka, T.S., Yang–Feng, T.L., Francke, U., Caron, M.G., Lefkowitz, R.J., and Regan, J.W. (1987) Science 238, 650–656.

Lomasney, J.W., Lorenz, W., Allen, L.F., King, K., Regan, J.W., Yang–Geng, T.L., Caron, M.G., and Lefkowitz, R.J. (1990) Proc.Nat.Acad.Sci 87, 5094–5098.

Regan, J.W., Kobilka, T.S., Yang–Feng, T.L., Caron, M.G., Lefkowitz, R.J., and Kobilka, B.K. (1988) Proc.Natl.Acad. Sci., USA 85, 6301–6305.

Hein, L., Altman, J.D., and Kobilka, B.K. (1999) Nature 402, 181–184.

Gavin, K.T., Colgan, M.P., Moore, D., Shanik, G., and Docherty, J.R. (1997) Naunyn Schmiedeberg's Arch Pharmacol 355, 406–411.

Sallinen, J., Haapalinna, A., Macdonald, E., Viitamaa, T., Lahdesmaki, J., Rybnikova, E., Pelto–Huikko, M., Kobilka, B.K., and Scheinin, M. (1999) Mol Psychiatry 4, 443–452.

Green, S.A., Cole, G., Jacinto, M., Innis, M., and Liggett, S.B. (1993) J Biol Chem 268, 23116–23121.

Green, S.A., Turkl, J., Innis, M., and Liggett, S.B. (1994) Biochem 33, 9414–9419.

Mason, D.A., Moore, J.D., Green, S.A., and Liggett, S.B. (1999) J Biol Chem 274, 12670–12674.

Eason, M.G. and Liggett, S.B. (1992) J. Biol. Chem. 267, 25473–25479.

Fraser, C.M., Arakawa, S., McCombie, W.R., and Venter, J.C. (1989) J. Biol.Chem 264, 11754–11761.

Eason, M.G., Kurose, H., Holt, B.D., Raymond, J.R., and Liggett, S.B. (1992) J.Biol.Chem. 267, 15795–15801.

Jewell–Motz, E.A., Donnelly, E.T., Eason, M.G., and Liggett, S.B. (1998) Biochem 37, 15720–15725.

Schwim, D.A., Page, S.O., Middleton, J.P., Lorenz, W., Liggett, S.B., Yamamoto, K., Caron, M.G., Lefkowitz, R.J., and Cotecchia, S. (1991) Mol.Pharmacol. 40, 619–626.

Martin, T.F.J. (1983) J Biol Chem 258, 14816–14822.

Eason, M.G., Jacinto, M.T., Theiss, C.T., and Liggett, S.B. (1994) Proc.Natl.Acad.Sci., USA 91, 11178–11182.

Smith, P.K., Krohn, R.I., Hermanson, G.T., Mallia, A.K., Gartner, F.H., Provenzano, M.D., Fujimoto, E.K., Goeke, N.M., Olson, B.J., and Klenk, D.C. (1985) Anal.Biochem. 150, 76–85.

Okamoto, T. and Nishimoto, I. (1992) J.Biol.Chem. 267, 8342–8346.

Ikezu, T., Okamoto, T., Ogata, E., and Nishimoto, I. (1992) FEBS 311, 29–32.

Dorn, G.W., Oswald, K.J., McCluskey, T.S., Kuhel, D.G., and Liggett, S.B. (1997) Biochem 36, 6415–6423.

Luttrell, L.M., van Biesen, T., Hawes, B.E., Koch, W.J., Krueger, K.M., Touhara, K., and Lefkowitz, R.J. (1997) Adv Second Messenger Phosphoprotein Res 31, 263–277.

Schramm, N.L. and Limbird, L.E. (1999) J Biol Chem 274, 24935–24940.

Rosin, D.L., Talley, E.M., Lee, A., Stornetta, R.L., Gaylinn, B.D., Guyenet, P.G., and Lynch, K.R. (1996) J Comp Neurol 372, 135–165.

Shi, T.J., Winzer–Serhan, U., Leslie, F., and Hokfelt, T. (1999) NeuroReport 10, 2835–2839.

Morgan, C.A., Southwick, S.M., Grillon, C., Davis, M., Krystal, J.H., and Charney, D.S. (1993) Psychopharmacology 110, 342–346.

Eason, M.G. and Liggett, S.B. (1993) Mol.Pharmacol.44, 70–75.

Adolfsson, P.I., Dahle, L.O., Berg, G., and Svensson, S.P.S. (1998)Gynecol Obstet Invest 45, 145–150.

Tan, S., Hall, L.P., Dewar, J., Dow, E., and Lipworth, B. (1997) Lancet 350, 995–999.

Liggett, S.B., Wagoner, L.E., Craft, L.L., Hornung, R.W., Hoit, B.D., McIntosh, T.C., and Walsh, R.A. (1998) J Clin Invest 102, 1534–1539.

Large, V., Hellstrom, L., Reynisdottir, S., Lonnqvist, F., Eriksson, P., Lannfelt, L., and Arner, P. (1997) J Clin Invest 100, 3005–3013.

Comings, D.E., Gade–Andavolu, R., Gonzalez, N., Blake, H., Wu, S., and MacMurray, J.P. (1999) Clin Genet 55, 160–172.

Martin Blum, Anne Demierre, Dems M. Grant, Markus Heim, and Urs A. Meyer, Proc.Natl.Acad.Sci.USA, 88:5237–5241.

Louis M. Luttrell, Tim van Biesen, Brian E. Hawes, Walter J. Koch, Kathleen M. Krueger, Kazushige Touhara, and Robert J. Lefkowitz, Advances in Second Messenger and Phosphoprotein Research, 31:263–277 (1997).

http://www.adrenoceptor.com/alphaintro.htm

Small et al. Polymorphic Deletion of Three Intracellular Acidic Residues of the 2B–Adrenergic Receptor decreases G Protein–coupled Receptor K. Nase–Mediated Phosphorylation and Desensitization. The Journal of Biol. Chem. 276:4917–4922.

Kumari, F., Cotter, P., Corr, P.J., and Gray, J.A. (1996) Psychopharmacology 123, 353–360.

Jinong Feng, Janet L. Sobell, Leonard L. Heston, David Goldman, Edwin Cook Jr., Henry R. Kranzler, Joel Gelernter, and Steve S. Sommer Am. J. Med. Genet. 81:405–410 (1998).

* cited by examiner (SEQ ID NO. 59)
GCCCAANGGTCTGG
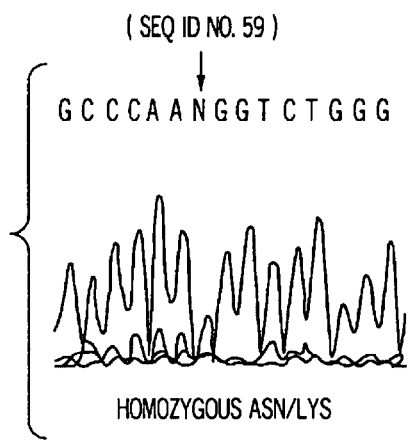
HOMOZYGOUS ASN/LYS
FIG. 5C
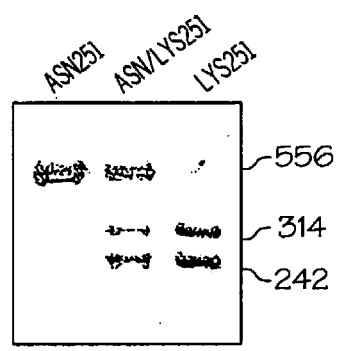
FIG. 5D
|  | 257 |  |  |  |  | 251 |  |  |  |  | 245 |  |  |
|---|---|---|---|---|---|---|---|---|---|---|---|---|---|
| HUMAN | R | E | P | G | L | G | N/K | P | R | R | E | T | G (SEQ ID NO. 60) |
| MOUSE | R | E | P | G | L | G | N | P | R | R | D | A | G (SEQ ID NO. 62) |
| RAT | R | E | P | G | V | A | N | P | R | R | D | A | G (SEQ ID NO. 63) |
| GUINEAS PIG | R | E | L | G | L | G | N | P | R | R | E | A | G (SEQ ID NO. 64) |
| BOS TAURUS | R | E | P | G | L | G | N | P | R | R | E | A | S (SEQ ID NO. 65) |
| PIG | R | E | P | G | L | G | N | P | R | R | E | A | G (SEQ ID NO. 66) |
FIG. 6

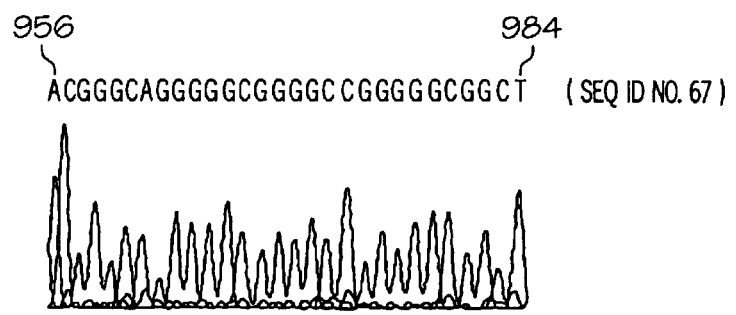
FIG. 11A
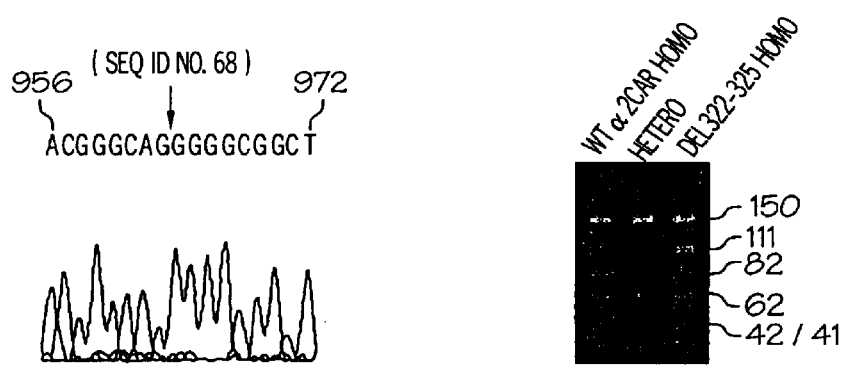
FIG. 11B
FIG. 11C

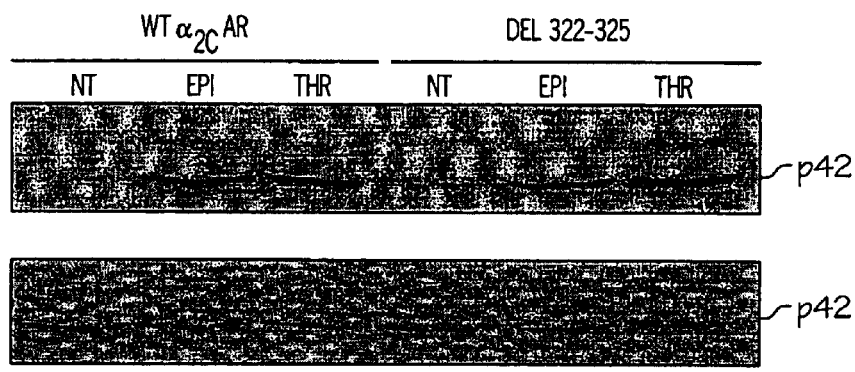
FIG. 15A
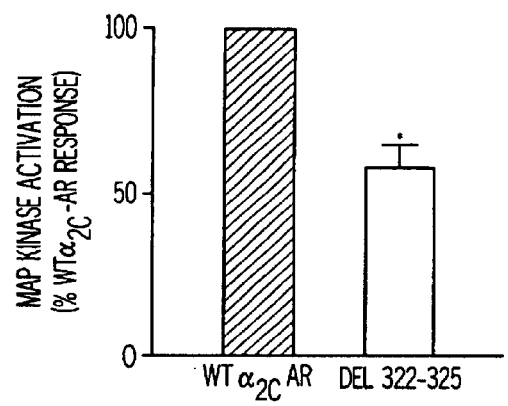 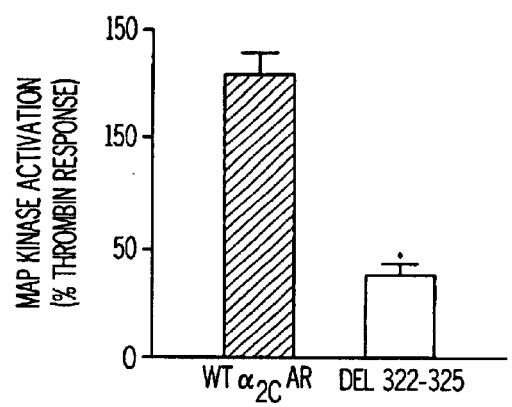
FIG. 15B
FIG. 15C

ALPHA-2 ADRENERGIC RECEPTOR POLYMORPHISMS

This application is a continuation-in-part and claims the benefit of the filing date of: U.S. application Ser. No. 09/551,744, filed Apr. 17, 2000, entitled "Alpha-2C-Adrenergic Receptor Polymorphisms", now abandonded U.S. application Ser. No. 09/636,259, filed Aug. 10, 2000, entitled "Alpha-2A-Adrenergic Receptor Polymorphisms", now abandonded and U.S. application Ser. No. 09/692,077, filed Oct. 19, 2000, entitled "Alpha-2B-Adrenergic Receptor Polymorphisms" and International Application No: PCT/US01/12575, filed Apr. 17, 2001, entitled "Alpha-2 Adrenergic Receptor Polymorphisms", these entire disclosures are hereby incorporated by reference into the present disclosure.

This invention was made, in part, with government support by National Institutes of Health grants ES06096, and HL53436. The U.S. Government may have certain rights in this invention.

FIELD OF THE INVENTION

The invention relates to polymorphisms in the gene encoding an alpha adrenergic receptor subtype. These polymorphisms result in altered alpha-adrenergic receptor function and can cause or modify a disease and/or alter the response to pharmacologic treatment. More specifically, the present invention relates to polymorphisms in the alpha-2B, alpha-2A and alpha-2C adrenergic receptor gene and the expressed alpha-2B, alpha-2A and the alpha-2C adrenergic receptor. The invention further relates to methods and molecules for identifying one or more polymorphisms in the alpha-2B, alpha-2A and alpha-2C adrenergic receptor gene and gene product. The present invention also provides methods of diagnosing, prognosing and treating individuals with diseases associated with one or more polymorphisms in the alpha-2B, alpha-2A and alpha-2C adrenergic receptor.

BACKGROUND OF THE INVENTION

Alpha adrenergic receptors are plasma membrane receptors which are located in the peripheral and central nervous systems throughout the body. They are members of a diverse family of structurally related receptors which contain seven putative helical domains and transduce signals by coupling to guanine nucleotide binding proteins (G-proteins).

The alpha adrenergic receptor family of adrenergic receptors (AR) consists of two groups: alpha-1 and alpha-2. Of the alpha-2 group, there are three distinct subtypes denoted alpha-2A, alpha-2B and alpha-2C. The subtypes are derived from different genes, have different structures, unique distributions in the body, and specific pharmacologic properties. (Due to localization of the genes to human chromosomes 10, 2 and 4, the alpha-2A, alpha-2B, and alpha-2C receptors have sometimes been referred to as alpha-2C10, alpha-2C2 and alpha-2C4 receptors, respectively). Like other adrenergic receptors, the alpha-2 receptors are activated by endogenous agonists such as epinephrine (adrenaline) and norepinephrine (noradrenaline), and synthetic agonists, which promote coupling to G-proteins that in turn alter effectors such as enzymes or channels.

The alpha-2 receptors couple to the $G_i$ and $G_o$ family of G-proteins. Alpha-2 receptors modulate a number of effector pathways in the cell: inhibition of adenylyl cyclase (decreases cAMP), stimulation of mitogen activated protein (MAP) kinase, stimulation of inositol phosphate accumulation, inhibition of voltage gated calcium channels and opening of potassium channels. (1,2). The alpha-2 receptors are expressed on many cell-types in multiple organs in the body including those of the central and peripheral nervous systems.

There has been a considerable research effort to clone and sequence the alpha-2AR. For example, the gene encoding the alpha-2A, alpha-2B, alpha-2C subtypes has been cloned and sequenced. (Kobilka et al. *Science* 238, 650–656 (1987); Regan et al., Lomasney et al. *Proc. Nat. Acad. Sci.* 87, 5094–5098 (1994)).

Alpha-2BAR

Alpha-2BAR have a distinct pattern of expression within the brain, liver, lung, and kidney, and recent studies using gene knockouts in mice have shown that disruption of this receptor effects mouse viability, blood pressure responses to alpha-2-AR agonists, and the hypertensive response to salt loading. See (13);(14).

It is known that the alpha-2BAR undergoes short-term agonist promoted desensitization(17). This desensitization is due to phosphorylation of the receptor, which evokes a partial uncoupling of the receptor from functional interaction with $G_i/G_o$ (18, 19)). Such phosphorylation appears to be due to G protein coupled receptor kinases (GRKs), a family of serine/threonine kinases which phosphorylate the agonist-occupied conformations of many G-protein coupled receptors (20). The phosphorylation process serves to finely regulate receptor function providing for rapid adaptation of the cell to its environment. Desensitization may also limit the therapeutic effectiveness of administered agonists. For the $\alpha_{2B}AR$, phosphorylation of serines/threonines in the third intracellular loop of the receptor is dependent on the presence of a stretch of acidic residues in the loop that appears to establish the milieu for GRK function (18).

A polymorphism occurring in the gene encoding the alpha-2BAR has been previously reported. This polymorphism has been described as a deletion of three glutamic acid residues in a highly acidic stretch of amino acids in the third intracellular loop of the receptor. (21, 22). However, no pharmacologic studies have been carried out to determine if this polymorphism alters receptor function.

Given the importance of the alpha-2BAR in modulating a variety of physiological functions, there is a need in the art for improved methods to identify polymorphisms and to correlate the identity of these polymorphisms with signaling functions of alpha-2BAR. The present invention addresses these needs and more by providing polynucleotide and amino acid polymorphisms, molecules, and methods for detecting, genotyping and haplotyping the polymorphisms in the alpha-2BAR. The present invention is useful for determining an individual's risk for developing a disease, assist the clinician in diagnosing and prognosing the disease. The present invention also provides methods for selecting appropriate drug treatment based on the identity of such polymorphism.

Alpha-2AAR

Alpha-2AAR are the principal presynaptic inhibitory autoreceptors of central and peripheral sympathetic nerves and inhibit neurotransmitter release in the brain and cardiac sympathetic nerves. (4). Such inhibition of neurotransmitter release in the brain is the basis for the central hypotensive, sedative, anesthetic-sparing, and analgesic responses of alpha-2AAR agonists (5,6). Indeed, alpha-2AAR agonists such as clonidine and guanabenz are potent antihypertensive agents which act via central presynaptic alpha-2AAR (7). The blood pressure and other responses to alpha-2AAR agonists and antagonists, though, are subject to interindividual variation in the human population (7–9). Such variation, of course, can be due to genetic variation in the structure of the receptor itself, its cognate G-proteins, the effectors, or downstream intracellular targets.

Of particular interest are physiologic and genetic studies which suggest that altered alpha-2AAR function can predispose individuals to essential hypertension ((7–9). Other physiologic functions of the alpha-2AAR are known. For example, the alpha-2AAR act to inhibit insulin secretion by pancreatic beta-cells, contract vascular smooth muscle, inhibit lipolysis in adipocytes, modulate water and electrolyte flux in renal cells, and aggregate platelets (3). Thus, like what has been shown with beta-AR polymorphisms (12), potential polymorphisms of the alpha-2AAR may act as risk factors for disease, act to modify a given disease, or alter the therapeutic response to agonists or antagonists.

Polymorphisms near the coding regions in the alpha-2A, alpha-2C and dopamine β-hydroxylase (DBH) genes have been reported causing increased levels of norepinephrine in children with attention-deficit hyperactivity disorder (Comings et al. Clin Genet 55, 160–172 (1999)). Indeed, there have been several reports of non-coding region polymorphisms (i.e., in the 5' and 3' untranslated region) of the human alpha-2A AR. One report has identified three SNPs in the coding region (Feng et al. Am. J. Med. Genet. (Neuropsychiatr. Genet.) 81, 405–410 (1998). In this work, though, no pharmacologic studies were carried out to determine if these polymorphisms alter receptor function.

Given the importance of the alpha-2AAR in modulating a variety of physiological functions, there is a need in the art for improved methods to identify polymorphisms and to correlate the identity of these polymorphisms with signaling functions of alpha-2AAR. The present invention addresses these needs and more by providing nucleic acid and amino acid polymorphisms, molecules, and methods for identifying the polymorphisms in the alpha-2AAR. The present invention is useful for determining an individual's risk for developing a disease, assist the clinician in diagnosing and prognosing the disease. The present invention also provides methods for selecting appropriate drug treatment based on the identity of such polymorphism.

Alpha-2CAR

Alpha-2CAR plays specific roles in certain central nervous system functions, such as for example, modulation of the acoustic startle reflex, prepulse inhibition, isolation induced aggregation, spatial working memory, development of behavioral despair, body temperature regulation, dopamine and serotonin metabolism, presynaptic control of neurotransmitter release from cardiac sympathetic nerves, central neurons, and postjunctional regulation of vascular tone Sallinen et al. Mol. Pharmacol. 51, 36–46 (1997); Sallinen et al. The Journal of Neuroscience 18, 3035–3042 (1998); Tanila et al. European Journal of Neuroscience 11, 599–603 (1999); Bjorklund et al. Mol Pharmacol 54, 569–576 (1998); Hein et al. Nature 402, 181–184 (1999); Gavin et al. Naunyn Schmiedebergs Arch Pharmacol 355, 406–411 (1997); Sallinen et al. Mol Psychiatry 4, 443–452 (1999).

Polymorphisms near the coding regions in the alpha-2A, alpha-2C and dopamine β-hydroxylase (DBH) genes have been reported causing increased levels of norepinephrine in children with attention-deficit hyperactivity disorder (Comings et al. Clin Genet 55, 160–172 (1999)).

To date polymorphisms occurring in nucleic acids encoding the alpha-2CAR receptor molecule and in the alpha-2C receptor have not been reported.

Given the importance of the alpha-2CAR in modulating a variety of physiological functions, there is a need in the art for improved methods to identify these polymorphisms and to correlate the identity of these polymorphisms with the physiological functions of alpha-2CAR. The present invention addresses these needs and more by providing nucleic acid and amino acid polymorphisms, molecules, and methods for identifying the polymorphisms in the alpha-2CAR. The present invention is useful for determining an individual's risk for developing a disease and to diagnosis and prognosis the disease. The present invention also provides methods for selecting appropriate drug treatment based on the identity of such polymorphisms.

SUMMARY OF THE INVENTION

The present invention provides methods, molecules, kits, and primers useful for detecting one or more polymorphic sites in polynucleotides encoding the alpha-2B, alpha-2A or alpha-2C adrenergic receptor gene and gene products.

In some embodiments, the present invention provides polymorphisms in nucleic acids encoding the alpha-2B, alpha-2A, and alpha-2C adrenergic receptor and expressed alpha-2B, alpha-2A and alpha-2C adrenergic receptor molecule.

In other embodiments, the present invention provides molecules and methods to diagnosis, prognosis, and treat diseases such as cardiovascular and central nervous system disease that are associated with the alpha-2B, alpha-2A or alpha-2C adrenergic receptor gene and/or gene products.

For a better understanding of the present invention together with other and further advantages and embodiments, reference is made to the following description taken in conjunction with the examples, the scope of which is set forth in the appended claims.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying figures, wherein:

FIG. 6 illustrates the location of the Lys251 alpha-2-AAR polymorphism and alignment of flanking amino acid residues of the third intracellular loop from various species. The locations of the Lys251 amino acid polymorphism in the third intracellular loop as well as two synonymous SNPs (single nucleotide polymorphisms) are indicated. Alignment of alpha-2AAR amino acid sequence from various species shows that this region is highly conserved and that Asn at position 251 is invariant in all mammalian species reported to date except for humans where we have noted the Lys polymorphism, SEQ ID NOS: 60 and 61. Amino acids in the mid-portion of the third intracellular loop are represented as solid dots for convenience.

FIG. 11 illustrates sequence variation of the human alpha-2CAR at nucleotides 964–975. Shown are automated sequencing chromatograms (sense strand) from individuals homozygous for the wild-type alpha-2CAR, SEQ ID NO: 67. (Panel A) and Del322–325 polymorphism, SEQ ID NO: 68, (Panel B). The underlined bases in A represent the nucleotides that were found to be deleted in the polymorphic sequence (arrow in B). Panel C shows agarose gel of PCR products from wild-type (WT) homozygous (384 bp), Del322–325 homozygous (372 bp), and heterozygous individuals digested with Nci 1. Wild-type receptor provides for the bands at the indicated molecular sizes (two products of 6 and 1 bp are not shown). The loss of one of the six Nci 1 sites due to the polymorphism results in a unique product of 111 bp and loss of the 82 and 41 bp products. Heterozygotes have all six fragments.

FIG. 15 illustrates stimulation of MAP kinase by wild-type and Del322–325 alpha-2CARs. Phosphorylation of MAP kinase was determined in CHO cells by quantitative immunoblotting with enhanced chemifluorescence using antibodies specific for phosphorylated Erk1/2. The same blots were stripped and reprobed for total MAP kinase expression, which was not significantly different between the two cell lines (Panel A). Cells were studied after incubation with carrier (basal), 10 μM epinephrine or 1 unit/ml thrombin. Results are depicted as the fold-stimulation over basal normalized to the wild-type response (Panel B) and the percent of the thrombin response (Panel C). *, p<0.005 compared to wild-type response (n=5 experiments).

DETAILED DESCRIPTION OF THE INVENTION

Alpha-2BAR, Alpha-2AAR and Alpha-2CAR Functions

Figure 1A:
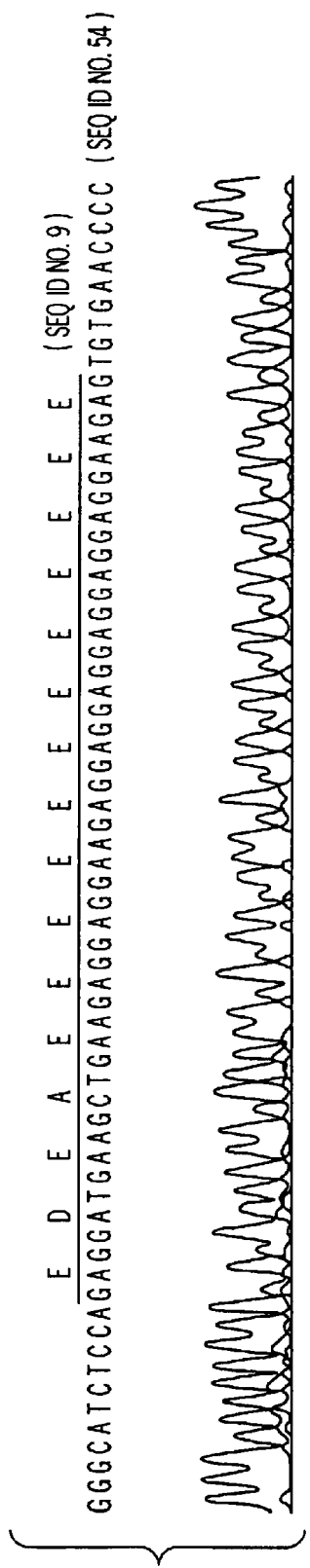
FIG. 1 illustrates identification of the human alpha-2BAR variant. Shown in Panels A and B are representative automated sequence chromatograms identifying a deletion of the nucleotides GAAGAGGAG (SEQ ID NO: 3). Panel C illustrates a rapid screening technique that identifies homozygous and heterozygous PCR products by size.

The alpha-2 adrenergic receptors are localized at the cell membrane and serves as receptors for endogenous catecholamine agonists i.e., epinephrine and norepinephrine, and synthetic agonists and antagonists. Upon binding of the agonist, the receptors stabilize in a conformation that favors contact with all activation of certain heterotrimeric G proteins. These include $G_{i1}$, $G_{i2}$, $G_{i3}$ and $G_o$. The $G_i$ G protein alpha subunits serve to decrease the activity of the enzyme adenylyl cyclase, which lowers the intracellular levels of cAMP (a classic second messenger). The alpha subunits, and/or the beta-gamma subunits of these G proteins also act to activate MAP kinase, open potassium channels, inhibit voltage gated calcium channels, and stimulate inositol phosphate accumulation. The physiologic consequences of the initiation of these events include inhibition of neurotransmitter release from central and peripheral noradrenergic neurons.

Alpha-2BARs are expressed in the brain, liver, lung, and kidney. Studies using gene knockouts in mice have shown that disruption of this receptor effects mouse viability, blood pressure responses to alpha-2-AR agonists, and the hypertensive response to salt loading. Alpha-2BAR when stimulated cause vasoconstriction.

Alpha-2BARs undergoes short-term agonist promoted desensitization. This desensitization is due to phosphorylation of the receptor, which evokes a partial uncoupling of the receptor from functional interaction with $G_i/G_o$. Such phosphorylation appears to be due to GRKs, a family of serine/threonine kinases which phosphorylate the agonist-occupied conformations of many G-protein coupled receptors. Desensitization may also limit the therapeutic effectiveness of administered agonists. For the alpha-2BAR, phosphorylation of serines/threonines in the third intracellular loop of the receptor is dependent on the presence of a stretch of acidic residues in the loop that appears to establish the milieu for GRK function (18).

The alpha-2A has been localized in brain, blood vessels, heart, lung, skeletal muscle, pancreas, kidney, prostate, ileum, jejunum, spleen, adrenal gland and spinal cord (Eason et al. Molecular Pharmacology 44, 70–75 (1993); Zeng et al. Mol Brain Res 10, 219–225 (1991).

Alpha-2AARs are widely expressed and participate in a broad spectrum of physiologic functions including metabolic, cardiac, vascular, and central and peripheral nervous systems, via pre-synaptic and post-synaptic mechanisms. At peripheral sites, alpha-2AARs act to inhibit insulin secretion by pancreatic beta-cells, contract vascular smooth muscle, inhibit lipolysis in adipocytes, modulate water and electrolyte flux in renal cells, and aggregate platelets (3). As discussed above, the alpha-2AAR is the principal presynaptic inhibitory autoreceptor of central and peripheral sympathetic nerves (4). Such inhibition of neurotransmitter release in the brain is the basis for the central hypotensive, sedative, anesthetic-sparing, and analgesic responses of alpha-2AAR agonists (5,6).

Alpha-2AAR agonists such as clonidine and guanabenz are potent antihypertensive agents which act via central presynaptic alpha-2AARs (7). The blood pressure and other responses to alpha-2AAR agonists and antagonists, though, are subject to interindividual variation in the human population (7–9). Such variation can be due to genetic variation in the structure of the receptor itself, its cognate G-proteins, the effectors, or downstream intracellular targets. Of particular interest are physiologic and genetic studies which suggest that altered alpha-2AAR function can predispose individuals to essential hypertension. See for example,(7–9) (10,11). Thus, like what has been shown with beta-AR polymorphisms (12), potential polymorphisms of the alpha-2AAR can act as risk factors for disease, act to modify a given disease, or alter the therapeutic response to agonists or antagonists.

The alpha-2C has been localized in brain, blood vessels, heart, lung, skeletal muscle, pancreas, kidney, prostate, ileum, jejunum, spleen, adrenal gland and spinal cord (Eason et al. Molecular Pharmacology 44, 70–75 (1993); Zeng et al. Mol Brain Res 10, 219–225 (1991).Alpha-2CAR plays specific roles in certain central nervous system functions, such as for example, modulation of the acoustic startle reflex, prepulse inhibition, isolation induced aggression, spatial working memory, development of behavioral despair, body temperature regulation, dopamine and serotonin metabolism, presynaptic control of neurotransmitter release from cardiac sympathetic nerves and central neurons, and postjunctional regulation of vascular tone Sallinen et al. *Mol. Pharmacol.* 51, 36–46 (1997); Sallinen et al. *The Journal of Neuroscience* 18, 3035–3042 (1998); Tanila et al. *European Journal of Neuroscience* 11, 599–603 (1999); Bjorklund et al. *Mol Pharmacol* 54, 569–576 (1998); Hein et al. *Nature* 402, 181–184 (1999); Gavin et al. *Naunyn Schmiedebergs Arch Pharmacol* 355, 406–411 (1997); Sallinen et al. *Mol Psychiatry* 4, 443–452 (1999).

Since most organs have innervation by these neurons, the activities of the alpha-2A, the alpha-2B and the alpha-2C receptors can alter processes in many organ systems. Of particular therapeutic interest has been the development of highly subtype-specific alpha-2 agonists and antagonists. Such compounds, then, can selectively block or activate one subtype, such as the alpha-2B, without affecting the others. This would provide for highly specific responses without side-effects from activating the other subtypes.

Alpha-2B, alpha-2A and alpha-2C adrenergic receptor molecule function or activity can be measured by methods known in the art. Some examples of such measurement include radio-ligand binding to the alpha-2B, alpha-2A or alpha-2C adrenergic receptor molecule by an agonist or antagonist, receptor-G protein binding, stimulation or inhibition of adenyly cyclase, MAP kinase, phosphorylation or inositol phosphate (IP3). However, the polymorphisms of the present invention (discussed below) alter their respective alpha-2 adrenergic receptor molecule function or activity.

In one embodiment of the present invention, the DEL301–303 polymorphism showed depressed phosphorylation resulting in loss of short-term agonist-promoted receptor desensitization in the alpha-2BAR molecule. The DEL301–303 polymorphism also showed altered or decreased receptor coupling.

Alpha-2 Adrenergic Receptor Diseases

Alpha-adrenergic receptors play an important role in regulating a variety of physiological functions because of their distribution in many organs of the body and the brain. Thus, dysfunctional alpha-2B, alpha-2A or alpha-2C receptors can predispose to, or modify, a number of diseases or alter response to therapy. The present invention stems in part from the recognition that certain polymorphisms in the alpha-2BAR, alpha-2AAR or alpha-2CAR result in receptor molecules with altered functions. These altered functions put an individual at risk for developing diseases associated with the alpha-2BAR, alpha-2AAR or the alpha-2ACR.

As used herein, "disease" includes but is not limited to any condition manifested as one or more physical and/or psychological symptoms for which treatment is desirable, and includes previously and newly identified diseases and other disorders. Such diseases include cardiovascular diseases such as hypertension, hypotension, congestive heart failure, arrhythmias, stroke, myocardial infarction, neurogenic and obstructive peripheral vascular disease, ischemia-reperfusion damage and intermittent claudication, migraine, metabolic rate and combinations thereof. Central nervous systems (CNS) diseases are also contemplated by the present invention. Some examples of CNS diseases include Parkinsonism, Alzheimers, attention deficit disorder, hyperreactivity, anxiety, manic-depression and combinations thereof. Since the alpha-2B, alpha-2A and alpha-2C control certain central nervous system and peripheral functions as discussed above, dysfunctional polymorphisms are likely to be important in as of yet unclassified disorders of memory and behavior.

In one embodiment, the present invention includes methods of determining the risk an individual has for developing a disease. Alternatively, the present invention can be used to diagnose or prognose an individual with a disease. For example, a polymorphic site in the polynucleotide encoding the mutant alpha-2BAR identified as SEQ ID NO: 2, such as for example, nucleotide positions 901 to 909 can be detected. This polymorphic site corresponds to GAGGAG-GAG (SEQ ID NO: 4). Thus, the mutant receptor has a deletion of nine nucleotides (DEL901–909) GAAGAGGAG (SEQ ID NO: 3) when compared to the polynucleotide encoding the wild-type alpha-2BAR (IN901–909). This exemplified polymorphism results in amino acid deletions at positions 301 to 303 of the mutant alpha-2B adrenergic receptor molecule resulting in the mutant receptor identified as SEQ ID NO: 8. More particularly, the preferred polymorphism results in a deletion of 3 glutamic acids at amino acid positions 301 to 303 (DEL 301–303) of the alpha-2B adrenergic receptor molecule resulting in a receptor with decreased alpha-agonist function. Such polymorphism can be correlated to increasing an individual's risk for developing a disease, or can be used to determine a diagnosis or prognosis for the disease.

In another embodiment of the present invention, a polymorphic site in SEQ ID NO: 1, such as for example, nucleotide position 901 to 909 can be detected. This polymorphic site corresponds to (IN901–909) GAAGAGGAG (SEQ ID NO: 3) that is an insertion of these nine nucleotides compared to the polynucleotide encoding the mutant alpha-2BAR. This exemplified polymorphism results in amino acid insertion at positions 301 to 303 (IN301–303) of the alpha-2B adrenergic receptor molecule resulting in the wild-type receptor identified as SEQ ID NO: 7. More particularly, the preferred polymorphism results in an insertion of 3 glutamic acids at amino acid positions 301 to 303 of the alpha-2B adrenergic receptor molecule resulting in a receptor with increased alpha-agonist function and increased agonist-promoted desensitization. Such polymorphism can be correlated to decreasing an individual's risk for developing a disease, or can be used to determine a diagnosis or prognosis for the disease.

For the alpha-2AAR, a polymorphic site in SEQ ID NO: 24, such as for example, nucleotide position 753 can be detected. This polymorphic site corresponds to a cytosine in nucleic acids encoding the alpha-2AAR. This exemplified polymorphism results in asparagine at amino acid position 251 of SEQ ID NO: 26 of the alpha-2A adrenergic receptor molecule resulting in a receptor with decreased alpha-agonist function. Such polymorphism can be correlated to increasing an individual's risk for developing a disease, or can be used to determine a diagnosis or prognosis for the disease.

In another embodiment of the present invention, a polymorphic site in SEQ ID NO: 25, such as for example, nucleotide position 753 can be detected. This polymorphic site corresponds to a guanine in nucleic acids encoding the alpha-2AAR. This exemplified polymorphism results in lysine at amino acid position 251 of SEQ ID NO: 27 of the alpha-2A adrenergic receptor molecule resulting in a receptor with increased alpha-agonist function. Such polymorphism can be correlated to increasing an individual's risk for developing a disease, or can be used to determine a diagnosis or prognosis for the disease.

For the alpha-2CAR, a polymorphic site in SEQ ID NO: 42, such as for example, SEQ ID NO: 43 which corresponds to a twelve nucleotide deletion in nucleic acids is detected. This exemplified polymorphism results in the deletion of amino acids 322–325 of alpha-2C adrenergic receptor molecule resulting in a defective receptor.

As used herein, "diagnosis" includes determining the nature and cause of the disease, based on signs and symptoms of the disease and laboratory finding. One such laboratory finding is the identification of at least one polymorphism in nucleic acids encoding the alpha-2BAR, the alpha-2AAR or the alpha-2CAR. Prognosis of a disease includes determining the probable clinical course and outcome of the disease. Increased risk for the disease includes an individual's propensity or probability for developing the disease.

The terms "correlate the polymorphic site with a disease" includes associating the polymorphism which occurs at a higher allelic frequency or rate in individuals with the disease than individuals without the disease. Correlation of the disease with the polymorphism can be accomplished by bio-statistical methods known in the art, such as for example, by Chi-squared tests or other methods described by L. D. Fisher and G. vanBelle, *Biostatistics: A Methodology for the Health Sciences*, Wiley-Interscience (New York) 1993.

Preferably, the identity of at least one polymorphic site in an alpha-2B, alpha-2A or alpha-2C adrenergic receptor molecule is determined. Generally, in performing the methods of the present invention, the identity of more than one polymorphic site is determined. As used herein a polymorphic site includes one or more nucleotide deletions (DEL), insertions (IN), or base changes at a particular site in a nucleic acid sequence. In some preferred embodiments, the identity of between about two and about six polymorphic sites is determined, though the identification of other numbers of sites is also possible. Most preferably, the polymorphisms and molecules of the present invention are utilized in determining the identity of at least one polymorphic site of the alpha-2BAR, alpha-2AAR or alpha-2CAR molecule and using that identity as a predictor of increased risk for developing a disease. The type of polymorphism present can also dictate the appropriate drug selection. In other embodiments, the polymorphisms and molecules of the present are used for diagnosing or prognosing an individual with a disease associated with an alpha-2BAR, alpha-2AAR or alpha-2CAR molecule.

Alpha-2 Adrenergic Receptor Polymorphisms

The particular gene sequences of interest to the present invention comprise "mutations" or "polymorphisms" in the genes encoding the alpha-2B, alpha-2A and alpha-2C adrenergic receptor. The genomes of animals and plants naturally undergo spontaneous mutation in the course of their continuing evolution (J. F. Gusella (1986) *Ann. Rev. Biochem.* 55:831–854). These mutations may be in the form of deletions (DEL), insertions (IN), or base changes at a particular site in a nucleic acid sequence. This altered sequence and the initial sequence may co-exist in a species' population. In some instances, these changes confer neither an advantage or a disadvantage to the species and multiple alleles of the sequence may be in stable or quasi-stable equilibrium. In some instances, however, these sequence changes will confer a survival or evolutionary advantage to the species, and accordingly, the altered allele may eventually (i.e. over evolutionary time) be incorporated into the genome of many or most members of that species. In other instances, the altered sequence confers a disadvantage to the species, as where the mutation causes or predisposes an individual to a genetic disease. As used herein, the terms "mutation" or "polymorphism" refer to the condition in which there is a variation in the DNA sequence between some members of a species. Typically, the term "mutation" is used to denote a variation that is uncommon (less than 1%), a cause of a rare disease, and that results in a gene that encodes a non-functioning protein or a protein with a substantially altered or reduced function. Such mutations or polymorphisms include, but are not limited to, single nucleotide polymorphisms (SNPs), one or more base deletions, and one or more base insertions.

Polymorphisms may be synonymous or nonsynonymous. Synonymous polymorphisms when present in the coding region typically do not result in an amino acid change. Nonsynonymous polymorphism when present in the coding region alter one or more codons resulting in an amino acid replacement in the amino acid chain. Such mutations and polymorphisms may be either heterozygous or homozygous within an individual. Homozygous individuals have identical alleles at one or more corresponding loci on homologous chromosomes. While heterozygous individuals have two different alleles at one or more corresponding loci on homologous chromosomes. A polymorphism is thus said to be "allelic," in that, due to the existence of the polymorphism, some members of a species carry a gene with one sequence (e.g., the original or wild-type "allele"), whereas other members may have an altered sequence (e.g., the variant or, mutant "allele"). In the simplest case, only one mutated variant of the sequence may exist, and the polymorphism is said to be diallelic. For example, if the two alleles at a locus are indistinguishable in their effects on the organism, then the individual is said to be homozygous at the locus under consideration. If the two alleles at a locus are distinguishable because of their differing effects on the organism, then the individual is said to be heterozygous at the locus. In the present application, typographically, alleles are distinguished + and −. Using these symbols, homozygous individuals are +/+, or −/−. Heterozygous individuals are +/−. The occurrence of alternative mutations can give rise to triallelic and tetra-allelic polymorphisms, etc. An allele may be referred to by the nucleotide(s) that comprise the mutation.

Alpha 2-BAR Polymorphisms

The wild-type gene encoding the third intracellular loop of the human alpha-2B receptor molecule is disclosed in GenBank Accession No. #AF009500, the entire disclosure is herein incorporated by reference. As used herein, the term "gene" includes a segment of DNA that contains all the information for the regulated biosynthesis of an RNA product, including promoters, exons, introns, and other untranslated regions that control expression.

The terms "alpha-2B-adrenergic receptor polymorphism" or "alpha-2BAR polymorphism", are terms of art and refer to at least one polymorphic site in the polynucleotide or amino acid sequence of an alpha-2B adrenergic receptor gene or gene product. For purposes of the present application, the wild-type polynucleotide encoding the alpha-2B-adrenergic receptor is designated SEQ ID NO: 1 and the wild-type gene product comprising the alpha-2B-adrenergic receptor molecule, is designated amino acid SEQ ID NO: 7.

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference may be made to either strand and still comprise the same polymorphic site and an oligonucleotide may be designed to hybridize to either strand. Throughout this specification, in identifying a polymorphic site, reference is made to the sense strand, only for the purpose of convenience.

Preferred polymorphisms of the present invention occur in the gene encoding the alpha-2B adrenergic receptor molecule identified as SEQ ID NO: 1 or 2 or fragments thereof or complements thereof.

For the purposes of identifying the location of at least one polymorphism or polymorphic site, the first nucleotide of the start codon of the coding region (the adenine of the ATG in a DNA molecule and the adenine of the AUG in an RNA molecule) of the alpha-2BAR gene is considered nucleotide "1." This corresponds to nucleotide 1 of SEQ ID NO: 1 or 2. The end of the coding region corresponds to adenine at position 1353 for SEQ ID NO: 1. The end of the coding region corresponds to adenine at position 1344 for SEQ ID NO: 2. According to the present invention, polymorphisms can occur any where in the coding region identified as SEQ ID NO: 1 or 2.

TABLE 1

Preferred Alpha-2BAR Polymorphisms

| Type | Nucleotide Position | Nucleotide | Amino Acid position | Designation |
|---|---|---|---|---|
| Wild Type | 901 to 999 of SEQ ID NO:1 | GAAGAGGAG SEQ ID NO:3 | 301 to 303 of SEQ ID NO:7 | IN301–303 EEE SEQ ID NO:11 |
| Mutant | 901 to 999 of SEQ ID NO:2 | GAGGAGGAG SEQ ID NO:4 | 301 to 303 of SEQ ID NO:8 | DEL301– 303 CEP SEQ ID NO:12 |

For example, the polymorphism occurring in the polynucleotide encoding the wild-type alpha-2BAR molecule (identified as SEQ ID NO: 1) is a nine nucleotide base insertion (IN901–909) at nucleotide positions 901 to 909 of SEQ ID NO: 1. This nine nucleotide base insertion is identified as GAAGAGGAG (SEQ ID NO: 3) and is a polymorphic site or fragment (FIG. 1A) of SEQ ID NO:1. A complement to this polymorphic site includes CTTCTCCTC (SEQ ID NO: 5).

Figure 1B:
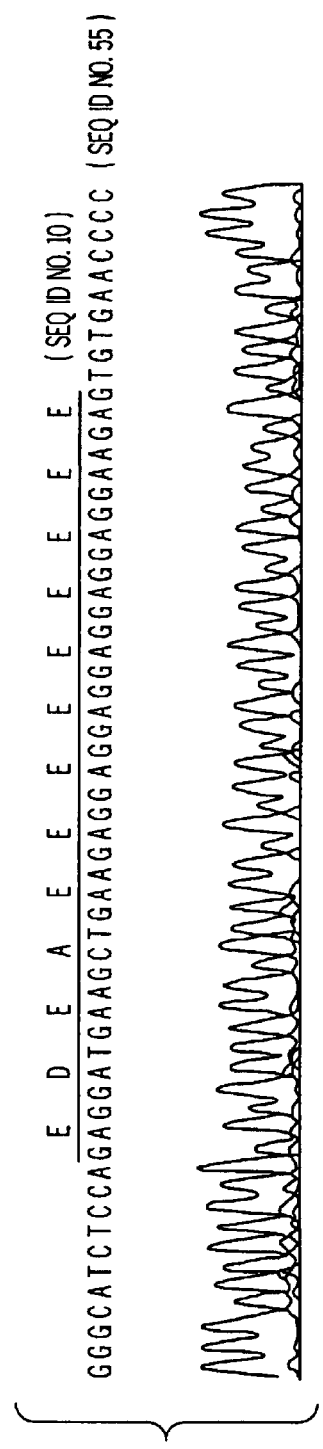
Figure 1C:
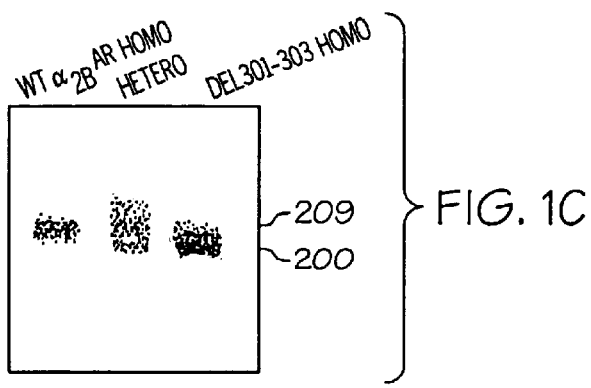

In another embodiment of the present invention, at least one polymorphic site has been identified in the polynucleotide encoding the mutant alpha-2BAR identified as SEQ ID NO: 2. This polymorphic site is a nine nucleotide deletion at nucleotide positions 901 to 909 (DEL901–909). This polymorphic site shifts GAGGAGGAG (SEQ ID NO: 4) into nucleotide positions 901 to 909. Thus, the polynucleotide encoding the mutant receptor has a deletion of nine nucleotides (FIG. 1B) GAAGAGGAG (SEQ ID NO: 3) when compared to the polynucleotide encoding the wild-type alpha-2BAR (identified as SEQ ID NO: 1). A compliment to the GAGGAGGAG (SEQ ID NO: 4) polymorphic site includes CTCCTCCTC (SEQ ID NO: 6).

An insertion or deletion polymorphism can change the exact position of at least one polymorphic site with respect to the polynucleotide encoding the alpha2-BAR identified as SEQ ID NO: 1 or 2. The present invention includes polymorphic sites occurring downstream of the IN/DEL901–909 polymorphic site. For example, detecting one or more single nucleotide polymorphisms (SNP) such as G at nucleotide position 915 and/or G at 951, will indicate the I901–909 polymorphism. Alternately, the end of the coding region of the polynucleotide can be probed to determine the longer polynucleotide indicating the IN901–909 polymorphism. For example, if a G SNP is detected at nucleotide position 1345, this indicates, the IN901–909 polymorphism of SEQ ID NO:1, since the mutant SEQ ID NO: 2 does not have this nucleotide position in the coding region. Thus, the IN/DEL901–909 polymorphic site can indirectly be detected by the nucleotide shift resulting from the insertion or deletion.

As used herein, "fragments of the polynucleotide encoding the alpha2-BAR" include less than the entire nucleotide sequence of SEQ ID NO: 1 or 2. The fragments comprise the polymorphic site or are associated with the polymorphic site. Preferred fragments comprise the IN901–909 or DEL901–909 polymorphic site. In order for a nucleic acid sequence to be a fragment, it must be readily identifiable by the molecular techniques as discussed such as with nucleic acid probes.

The polymorphisms of the present invention can occur in the translated alpha-2B adrenergic receptor molecule as well. For example, the first amino acid of the translated protein product or gene product (the methionine) is considered amino acid "1" in the wild-type alpha-2B adrenergic receptor molecule designated amino acid SEQ ID NO: 7. The end of the receptor corresponds to tryptophan at amino acid position 450 for SEQ ID NO: 7. Polymorphisms can occur anywhere in SEQ ID NO: 7. The wild-type alpha-2B adrenergic receptor molecule (FIG. 2) comprises an insertion of 3 glutamic acids at amino acid positions 301 to 303 (IN301–303) of the alpha-2B adrenergic receptor molecule designated EEE (SEQ ID NO: 11). Thus, in the stretch of amino acids at positions 294–309 identified as EDEAEEEEEEEEEE (SEQ ID NO: 9), there is an insertion of three additional glutamic acids when compared to the mutant alpha-2B adrenergic receptor molecule. Accordingly, EDEAEEEEEEEEEEEE (SEQ ID NO: 9) and EEE (SEQ ID NO: 11) are examples of polymorphic sites occurring in SEQ ID NO: 7.

Figure 2:
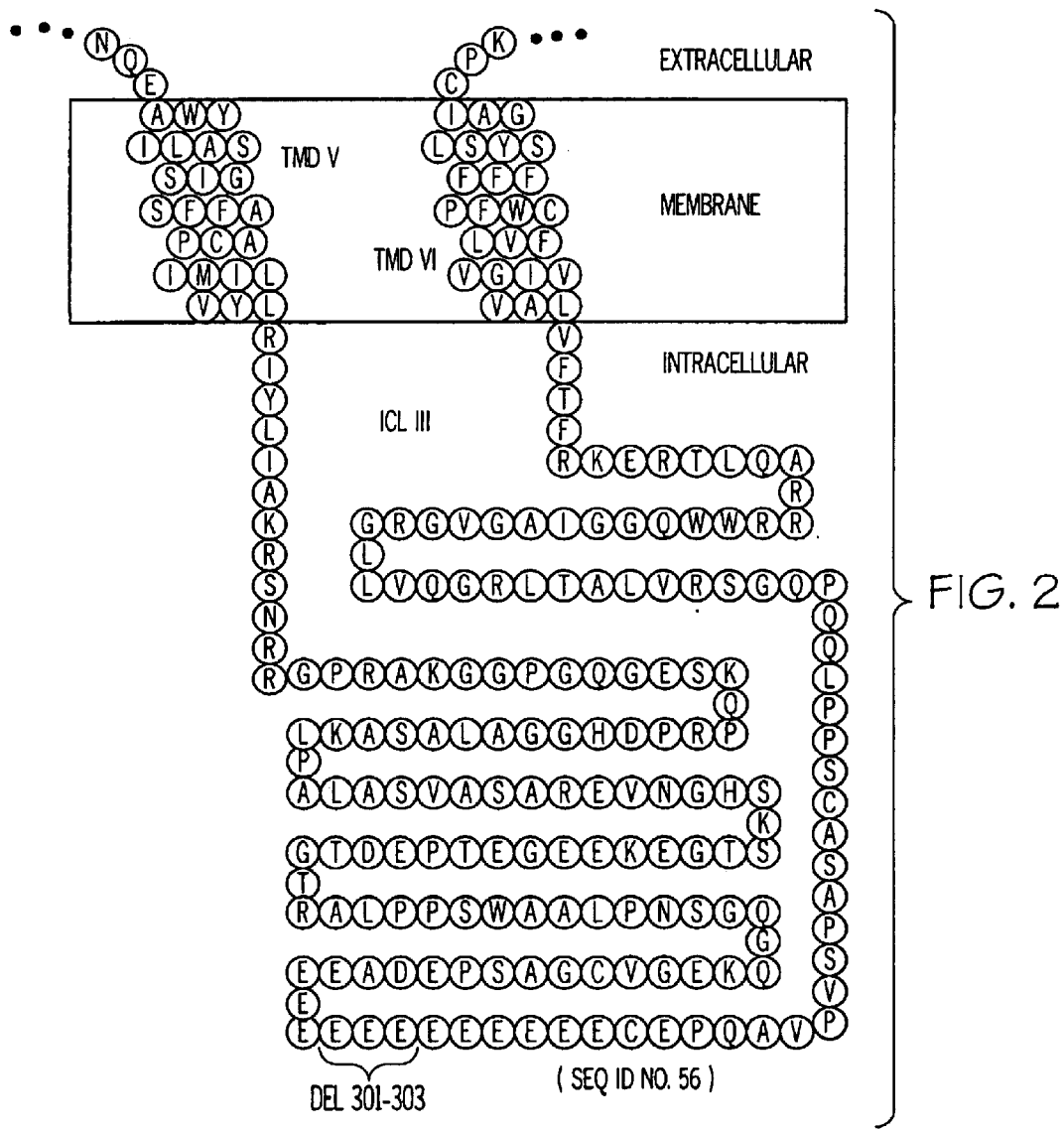
FIG. 2 illustrates localization of the expressed alpha-2BAR polymorphism. Shown is the fifth and sixth transmembrane spanning domain (TMD) and the third intracellular loop of the receptor, identified by the sequence designated as SEQ ID NO: 56.

In another embodiment of the present invention, SEQ ID NO: 8 comprises the entire mutant amino acid sequence of alpha-2B adrenergic receptor molecule with deletion of EEE at amino acid positions 301–303 (DEL301–303) (shown in FIG. 2). The first amino acid of the translated protein product or gene product (the methionine) is considered amino acid "1" in the mutant alpha-2B adrenergic receptor molecule designated amino acid SEQ ID NO: 8. The end of the receptor corresponds to tryptophan at amino acid position 447 for SEQ ID NO: 8. Polymorphisms can occur anywhere in the amino acid sequence designated SEQ ID NO: 8. For example, the mutant alpha-2B adrenergic receptor molecule comprises a deletion of EEE (SEQ ID NO: 11) or 3 glutamic acids in the mutant alpha-2B adrenergic receptor molecule. Thus, in the stretch of amino acids at positions 294–306 identified as EDEAEEEEEEEEE (SEQ ID NO: 10). There is a deletion of three glutamic acids when compared to the wild-type alpha-2B adrenergic receptor molecule. Accordingly, EDEAEEEEEEEEEEE (SEQ ID NO: 10) and EEE (SEQ ID NO: 11) are examples of polymorphic sites occurring in SEQ ID NO: 8.

Since the mutant alpha-2B adrenergic receptor molecule has DEL301–303, the rest of the molecule shifts causing amino acids 307, 308 and 309 to have CEP at these positions in the mutant receptor. Thus, another polymorphic site is CEP (SEQ ID NO: 12) at amino acid positions 307–309 of SEQ ID NO: 8, individually and/or collectively, these positions represent polymorphic sites when compared to the wild-type receptor. Alternatively, the mutant alpha-2B adrenergic receptor molecule lacks amino acids positions 448, 449 and 450. Thus, these are also polymorphic sites.

For example, an insertion or deletion polymorphisms can change the exact position of at least one polymorphic site with respect to the amino sequence of the alpha-2-BAR identified as SEQ ID NO: 7 or 8. The present invention includes one or more polymorphic sites occurring downstream of the IN/DEL301–303 polymorphic site. For example, detecting R at amino position 340 and/or R at 438, will indicate the IN301–303 polymorphism. Alternately, the end of the coding region of the polynucleotide can be probed to determine the longer chain of amino acids indicating the IN301–303 polymorphism. For example, if a T is detected at amino acid position 448, this indicates the wild-type IN301–303 polymorphism of SEQ ID NO: 7, since the mutant SEQ ID NO: 8 does not have this amino acid position with regards to the encoded gene product. Thus, the IN/DEL301–303 can be indirectly detected by detecting one or more amino acid positions downstream of IN/DEL301–303 polymorphic site.

The present invention includes fragments of gene products. Preferred gene product fragments of the alpha-2-BAR include less than the entire amino acid sequence of SEQ ID NO: 7 or 8. The fragments comprise the polymorphic site or are associated with the polymorphic site. Preferred gene product fragments comprise the IN301–303 or DEL301–303 polymorphic site. In order for an amino acid sequence to be a fragment, it must be readily identifiable by molecular and pharmacological techniques discussed below, such as for example, ligand binding.

The present invention includes homologs and fragments of the nucleic acids that encode alpha2-BAR. To be considered a homolog or active fragment, the sequence of an amino acid or a nucleic acid must satisfy two requirements. In the present specification, the sequence of a first nucleotide sequence (SEQ ID NO: 1 or 2) is considered homologous to that of a second nucleotide sequence if the first sequence is at least about 30% identical, preferably at least about 50% identical, and more preferably at least about 65% identical to the second nucleotide sequence. In the case of nucleotide sequences having high homology, the first sequence is at least about 75%, preferably at least about 85%, and more preferably at least about 95% identical to the second nucleotide sequence.

The amino acid sequence of a first protein (SEQ ID NO: 7 or 8) is considered to be homologous to that of a second protein if the amino acid sequence of the first protein shares at least about 20% amino acid sequence identity, preferably at least about 40% identity, and more preferably at least about 60% identity, with the sequence of the second protein. In the case of proteins having high homology, the amino acid sequence of the first protein shares at least about 75% sequence identity, preferably at least about 85% identity, and more preferably at least about 95% identity, with the amino acid sequence of the second protein.

In order to compare a first amino acid or nucleic acid sequence to a second amino acid or nucleic acid sequence for the purpose of determining homology, the sequences are aligned so as to maximize the number of identical amino acid residues or nucleotides. The sequences of highly homologous proteins and nucleic acid molecules can usually be aligned by visual inspection. If visual inspection is insufficient, other methods of determining homology are known in the art. For example, the proteins may be aligned in accordance with the FASTA method in accordance with Pearson et al. (1988). Preferably, any of the methods described by George et al., in Macromolecular Sequencing and Synthesis, Selected Methods and Applications, (1988).

A second test for homology of two nucleic acid sequences is whether they hybridize under normal hybridization conditions, preferably under stringent hybridization conditions. Also included in the invention are proteins that are encoded by nucleic acid molecules that hybridize under high stringent conditions to a sequence complementary to SEQ ID NO: 1 or 2. The term "stringent conditions," as used herein, is equivalent to "high stringent conditions" and "high stringency". These terms are used interchangeably in the art. High stringent conditions are defined in a number of ways. In one definition, stringent conditions are selected to be about 50° C. lower than the thermal melting point (Tm) for a specific sequence at a defined ionic strength and pH. The Tm is the temperature (under defined ionic strength and pH) at which 50% of the target sequence hybridizes to a perfectly matched sequence. Typical stringent conditions are those in which the salt concentration is at least about 0.02 M at pH 7 and the temperature is at least about 60° C. "Stringent conditions," in referring to homology or substantial similarity in the hybridization context, can be combined conditions of salt, temperature, organic solvents or other parameters that are typically known to control hybridization reactions. The combination of parameters is more important than the measure of any single parameter. If incompletely complementary sequences recognize each other under high stringency conditions, then these sequences hybridize under conditions of high stringency. See U.S. Pat. No. 5,786,210; Wetmur and Davidson J. Mol. Biol. 31:349–370 (1968). Control of hybridization conditions, and the relationships between hybridization conditions and degree of homology are understood by those skilled in the art. See, e.g., Sambrook, J. et al. (Eds.), Molecular Cloning, Second Edition, Cold Spring Harbor Laboratory Press, Cold Spring Harbor, N.Y. (1989) and Ausubel, F. M. et al. (Eds.), Current Protocols in Molecular Biology, John Wiley & Sons, New York (1999).

Substitutions, additions, and/or deletions in an amino acid sequence can be made as long as the protein encoded by the nucleic acid of the invention continues to satisfy the functional criteria described herein. An amino acid sequence that is substantially the same as another sequence, but that differs from the other sequence by means of one or more substitutions, additions, and/or deletions, is considered to be an equivalent sequence. Preferably, less than 50%, more preferably less than 25%, and still more preferably less than 10%, of the number of amino acid residues in a sequence are substituted for, added to, or deleted from the protein encoded by the nucleic acid of the invention.

Alpha-2AAR Polymorphisms

The wild-type gene encoding the third intracellular loop of the human alpha-2A receptor molecule is disclosed in GenBank Accession No. AF281308 which include the sequence corrections illuminated by (13), both references are herein incorporated by reference. The terms "alpha-2A-adrenergic receptor polymorphism" or "alpha-2AAR polymorphism", are terms of art and refer to at least one polymorphism in the nucleic acid or amino acid sequence of an alpha-2A adrenergic receptor gene or gene product.

For purposes of the present application, the wild-type gene encoding the alpha-2A-adrenergic receptor is designated SEQ ID NO: 24 and the wild-type gene product comprising the alpha-2A-adrenergic receptor molecule, is designated amino acid SEQ ID NO:26.

Preferred polymorphisms of the present invention occur in the gene encoding for the alpha-2A adrenergic receptor molecule identified as SEQ ID NO: 24 or 25 or fragments thereof or complements thereof.

For the purposes of identifying the location of at least one polymorphism or polymorphic site, the first nucleotide of the start codon of the coding region (the adenine of the ATG in a DNA molecule and the adenine of the AUG in an RNA molecule) of the alpha-2AAR gene is considered nucleotide "1." This corresponds to nucleotide 1 of SEQ ID NO:24 or 25. The end of the coding region corresponds to guanine at position 1350 of SEQ ID NO:24 or 25. According to the present invention, polymorphisms can occur any where in the coding region identified as SEQ ID NO:24 or 25.

Preferred single nucleotide polymorphisms and polymorphic sites occurring in the alpha-2AAR gene and the encoded protein or gene product include the following:

TABLE 2

Preferred Alpha-2AAR Polymorphisms

| Type | Nucleotide Position | Nucleot. | Amino Acid position | Designation |
| --- | --- | --- | --- | --- |
| Wild Type | 753 of SEQ ID NO: 24 | C | 251 of SEQ ID NO: 26 | Asn 251 |
| Mutant | 753 of SEQ ID NO: 25 | G | 251 of SEQ ID NO: 27 | Lys 251 |

Figure 5A:
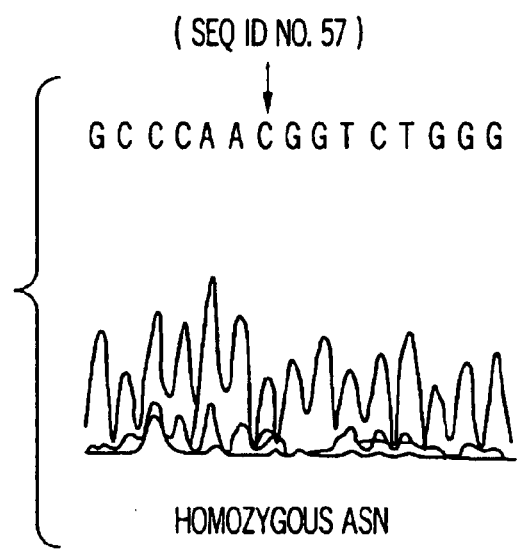
FIG. 5 illustrates sequence variation of the human alpha-2AAR at nucleoride position 753. Shown are sequence electropherograms (sense strand) of PCR products amplified from individuals homozygous for the wild-type alpha 2-AAR, GCCCAACGGTCTGGG; SEQ ID NO: 57, and Lys251 receptor, GCCCAAGGGTCTGGG; SEQ ID NO: 58, (Panels A and B), and a heterozygous individual, GCCCAANGGTCTGGG; SEQ ID NO: 59, (Panel C) as described below. The cytosine in the indicated position of codon 251 results in an Asn, whereas a guanine encodes for Lys. Panel D shows agarose gel of PCR products from homozygous wild-type (Asn), heterozygous (Asn/Lys), and homozygous polymorphic (Lys) individuals digested with Sty I. The C to G transversion at nucleotide 753 creates a unique Sty I site that results in partial and complete digestion of a 5566 bp fragment amplified from Lys251 heterozygous and bomozygous individuals, respectively.
Figure 5B:
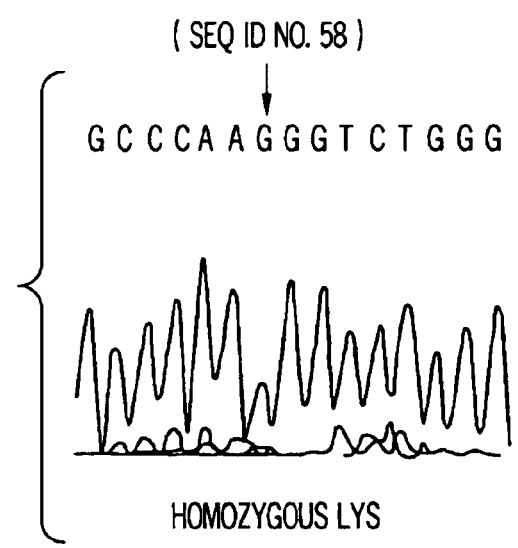

In one embodiment of the present invention, Applicants have discovered at least one polymorphic site on SEQ ID NO: 24 that encode the wild-type alpha-2AAR molecule (Table 2). Such polyimorphic site corresponds to C at nucleotide position 753 of SEQ ID NO: 24 in the coding region of the alpha-2AAR molecule (FIG. 5B). This SNP is localized within an intracellular domain of the alpha-2AAR molecule.

In another embodiment of the present invention at least one polymorphic site has been identified in SEQ ID NO: 25 that encodes the mutant alpha-2AAR molecule (Table 2). Such polymorphic site corresponds to G at nucleotide position 753 of SEQ ID NO: 25 in the coding region for the alpha-2AAR molecule (FIG. 5A). This SNP is localized within an intracellular domain of the alpha-2AAR molecule.

The polymorphisms of the present invention can occur in the translated alpha-2A adrenergic receptor molecule as well. For example, the first amino acid of the translated protein product or gene product (the methionine) is considered amino acid "1" in the wild-type or mutant alpha-2A adrenergic receptor molecule designated amino acid SEQ ID NO: 26 or 27, respectively. Polymorphisms can occur anywhere in SEQ ID NO: 26 or 27. The wild-type alpha-2A adrenergic receptor molecule (FIG. 6) comprises N at amino acid position 251 (Asn 251) of the alpha-2A adrenergic receptor molecule. Accordingly, amino acid position 251 is a polymorphic site (Table 2).

In another embodiment of the present invention, SEQ ID NO:27 is the entire mutant amino acid sequence of alpha-2A adrenergic receptor molecule. Polymorphisms can occur anywhere in the amino acid sequence designated SEQ ID NO:27. For example, the mutant alpha-2A adrenergic receptor molecule comprises G at amino acid position 251 (Lys 251) of the alpha-2A adrenergic receptor. Accordingly, amino acid position 251 is a polymorphic site (Table 2).

As used herein "fragments of the polynucleotide encoding the alpha-2A adrenergic receptor" include less than the entire nucleotide sequence of SEQ ID NO:24 or 25. The fragments comprise the polymorphic site or are associated with the polymorphic site. In order for a nucleic acid sequence to be a fragment, it must be readily identifiable by the molecular techniques as discussed below, such as with nucleic acid probes. Preferred gene product fragments of the alpha-2A adrenergic receptor include less than the entire amino acid sequence of SEQ ID NO: 26 or 27. The fragments comprise the polymorphic site or are associated with the polymorphic site. In order for an amino acid sequence to be a fragment, it must be readily identifiable by molecular and pharmacological techniques as discussed below, such as with ligand binding.

Alpha-2CAR

The wild-type gene encoding the third intracellular loop of the human alpha-2C receptor molecule is disclosed in GenBank Accession No. AF280399, which is herein incorporated by reference. The terms "alpha-2C-adrenergic receptor polymorphism" or "alpha-2CAR polymorphism", are terms of art and refer to at least one polymorphism in the nucleic acid or amino acid sequence of an alpha-2C adrenergic receptor gene or gene product. For purposes of the present application, the wild-type gene encoding the alpha-2C-adrenergic receptor is designated SEQ ID NO:40 and the wild-type gene product comprising the alpha-2C-adrenergic receptor molecule, is designated amino acid SEQ ID NO:44. For the purposes of identifying the location of at least one polymorphism or polymorphic site, the first nucleotide of the start codon of the coding region (the adenine of the ATG in a DNA molecule and the adenine of the AUG in an RNA molecule) of the alpha-2CAR gene is considered nucleotide "1." This corresponds to nucleotide 1 of SEQ ID NO:40. The end of the coding region corresponds to guanine at position 1383 of SEQ ID NO:40. According to the present invention, polymorphisms can occur any where in the coding region identified as SEQ ID NO:40.

TABLE 3

Preferred Alpha-2CAR Polymorphisms

| Type | Nucleotide Position | Nucleotide | Amino Acid position | Designation |
|---|---|---|---|---|
| Wild Type | 964–975 of SEQ ID NO: 40 | ggggcggggccg SEQ ID NO: 41 | 322–325 of SEQ ID NO: 44 | IN322–325 GAGP SEQ ID NO: 45 |
| Mutant | 964–975 of SEQ ID NO: 42 | ggggcggctgag SEQ ID NO: 43 | 322–325 of SEQ ID NO: 46 | DEL322–325 GAAE SEQ ID NO: 47 |

For example, Applicants have discovered at least one polymorphic site has been identified in SEQ ID NO:40 corresponding to an insertion of nucleotides at positions 964–975 of SEQ ID NO:40 which is the coding region for the alpha-2CAR molecule (FIG. 11A). This polymorphism is localized within an intracellular domain of the alpha-2CAR molecule. The twelve nucleotide insertion is listed as SEQ ID NO:41 ggggcggggccg which is an example of a fragment or polymorphic site of SEQ ID NO:40.

In another embodiment of the present invention at least one polymorphic site has been identified in SEQ ID NO: 42. Such polymorphic site is ggggcggctgag SEQ ID NO: 43. For example, the entire mutant nucleotide sequence encoding the alpha-2C adrenergic receptor molecule is identified as SEQ ID NO: 42. Polymorphisms can occur in the coding region identified as SEQ ID NO: 42. This polymorphic nucleotide sequence comprises ggggcggctgag SEQ ID NO: 43 at positions 964–975. Thus, SEQ ID NO: 42 comprises a twelve nucleotide deletion (FIG. 11B) at nucleotide positions 964–975 when compared to the wild-type acid sequence identified as SEQ ID NO:40.

The polymorphisms of the present invention can occur in the translated alpha-2C adrenergic receptor molecule as well. For example, the first amino acid of the translated protein product or gene product (the methionine) is considered amino acid "1" in the wild-type alpha-2C adrenergic receptor molecule designated amino acid SEQ ID NO:44. Polymorphisms can occur anywhere in SEQ ID NO:44. The wild-type alpha-2C adrenergic receptor molecule (FIG. 12) comprises GAGP at amino acid positions 322–325 of the alpha-2C adrenergic receptor molecule designated amino acid SEQ ID NO: 45. GAGP at amino acid positions 322–325 of the alpha-2C adrenergic receptor molecule is an example of a fragment or polymorphic site of SEQ ID NO:44.

Figure 12:
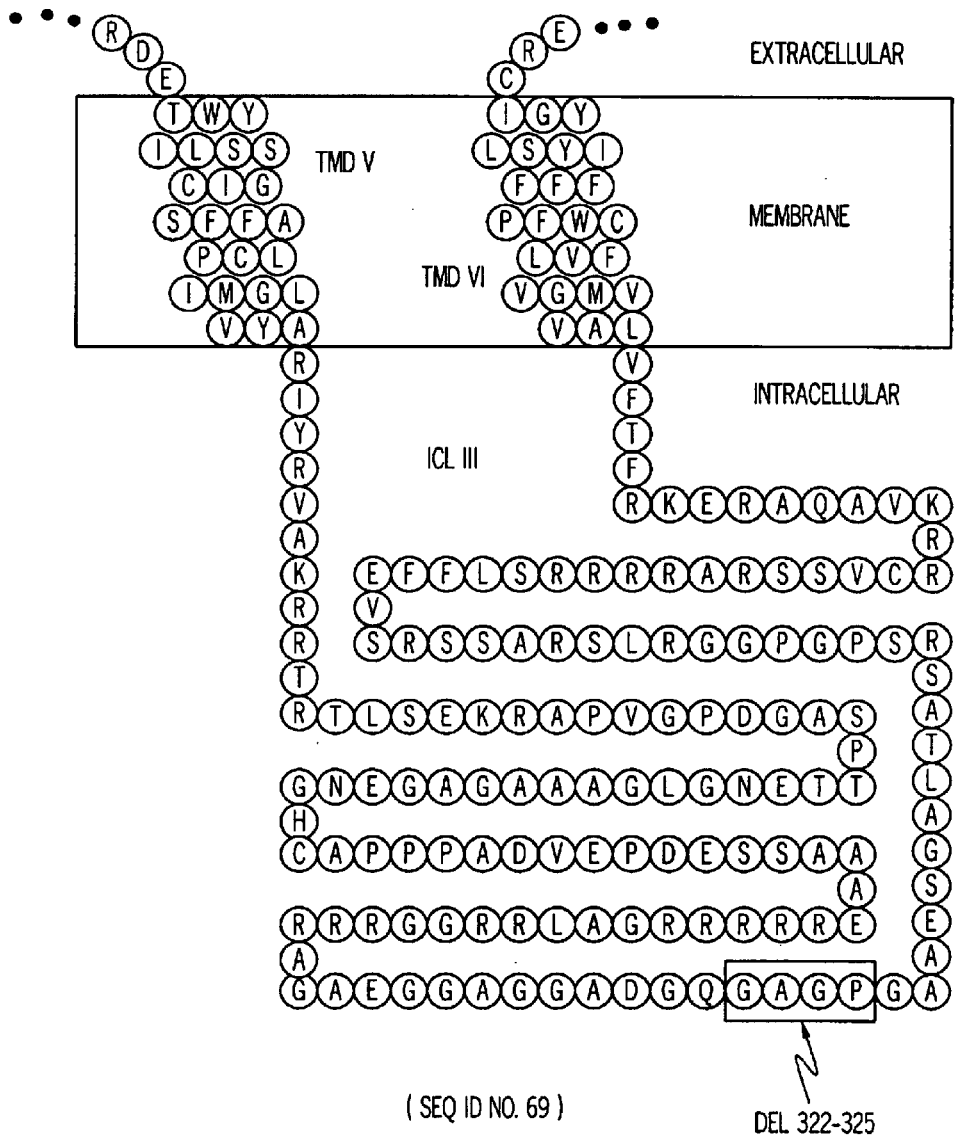
FIG. 12 illustrates the localization of the alpha-2CAR polymorphism. Shown is the amino acid sequence, SEQ ID NO: 69, and the proposed membrane topology of the fifth and sixth transmembrane spanning domains and the third intracellular loop. The polymorphism results in the loss of Gly-Ala-Gly-Pro at the indicated position. The third intracellular loop is shown in a compact form for illustrative purposes and is not intended to represent known secondary structure.

In another embodiment of the present invention, SEQ ID NO:46 is the entire mutant amino acid sequence of alpha-2C adrenergic receptor molecule with deletion of GAGP at amino acid positions 322–325 (shown in FIG. 12). Polymorphisms can occur anywhere in the amino acid sequence designated SEQ ID NO:46. For example, the mutant alpha-2C adrenergic receptor molecule comprises GAAE at amino acid positions 322–325 in alpha-2C adrenergic receptor molecule designated amino acid SEQ ID NO: 47. GAAE at amino acid positions 322–325 alpha-2C adrenergic receptor molecule is an example of a fragment or polymorphic site of SEQ ID NO:46. As used herein "fragments of the polynucleotide encoding the alpha-2C adrenergic receptor" include less than the entire nucleotide sequence of SEQ ID NO: 40 or 42. The fragments comprise the polymorphic site or are associated with the polymorphic site. In order for a nucleic acid sequence to be a fragment, it must be readily identifiable by the molecular techniques as discussed below, such as with nucleic acid probes. Preferred gene product fragments of the alpha-2C adrenergic receptor include less than the entire amino acid sequence of SEQ ID NO: 44 or 46. The fragments comprise the polymorphic site or are associated with the polymorphic site. In order for an amino acid sequence to be a fragment, it must be readily identifiable by molecular and pharmacological techniques as discussed below, such as with ligand binding.

In another embodiment, the present invention provides a computer readable medium recorded thereon the nucleotide sequence of SEQ ID NO: 43. As used herein, "computer readable medium" includes files in any of the following media: hard drive, diskette, magnetic tape, 8 mm data cartridge, compact disk and Magneto Optical Disk, and the like.

Alpha-2B, Alpha-2A, Alpha-2C Adrenergic Receptor Molecules

The molecules of the present invention are particularly relevant to determine increased risk an individual has for a disease and/or response to therapy. The molecules of the present invention can also be used to diagnosis and prognosis a disease.

The molecules of the present invention will preferably be "biologically active" with respect to either a structural attribute, such as the capacity of a nucleic acid to hybridize to another nucleic acid molecule or to be used by a polymerase as a primer. Alternatively, such an attribute may be catalytic, and thus involve the capacity of the agent to mediate a chemical reaction or response.

A preferred class of molecules of the present invention comprises adrenergic receptor molecules. Preferably, alpha-2B, alpha-2A, or alpha-2C adrenergic receptor molecules. These molecules may be either DNA or RNA, single-stranded or double-stranded. Alternatively, such molecules may be proteins and antibodies. These molecules may also be fragments, portions, and segments thereof and molecules, such as oligonucleotides, that specifically hybridize to nucleic acid molecules encoding the alpha-2B, alpha-2A, or alpha-2C adrenergic receptor. Such molecules may be isolated, derived, or amplified from a biological sample. Alternatively, the molecules of the present invention may be chemically synthesized. The term "isolated" as used herein refers to the state of being substantially free of other material such as nucleic acids, proteins, lipids, carbohydrates, or other materials such as cellular debris or growth media with which the alpha-2B, alpha-2A, or alpha-2C adrenergic receptor molecule, polynucleotide encoding the alpha-2B, alpha-2A, or alpha-2C adrenergic receptor molecule, primer oligonucleotide, or allele-specific oligonucleotide may be associated. Typically, the term "isolated" is not intended to refer to a complete absence of these materials. Neither is the term "isolated" generally intended to refer to water, buffers, or salts, unless they are present in amounts that substantially interfere with the methods of the present invention. The term "sample" as used herein generally refers to any material containing nucleic acid, either DNA or RNA or amino acids. Generally, such material will be in the form of a blood sample, stool sample, tissue sample, cells, bacteria, histology section, or buccal swab, either fresh, fixed, frozen, or embedded in paraffin.

As used herein, the term "polynucleotide" includes nucleotides of any number. A polynucleotide includes a nucleic acid molecule of any number of nucleotides including single-stranded RNA, DNA or complements thereof, double-stranded DNA or RNA, and the like. Preferred polynucleotides include SEQ ID NO: 1, 2, 24, 25, 40 or 42 and complements and fragments thereof. The term "oligonucleotide" as used herein includes a polynucleotide molecule comprising any number of nucleotides, preferably, less than about 200 nucleotides. More preferably, oligonucleotides are between 5 and 100 nucleotides in length. Most preferably, oligonucleotides are 10 to 50 nucleotides in length. The exact length of a particular oligonucleotide, however, will depend on many factors, which in turn depend on the ultimate function or use of the oligonucleotide. Short primer molecules generally require lower temperatures to form sufficiently stable hybrid complexes with the template.

Preferred oligonucleotides associated with the alpha-2BAR include:

```
5'-GCTCATCATCCCTTTCTCGCT-3';      (SEQ ID NO:13)

5'-AAAGCCCCACCATGGTCGGGT-3';      (SEQ ID NO:14)

5'-CTGATCGCCAAACGAGCAAC-3';       (SEQ ID NO:15)

5'-AAAAACGCCAATGACCACAG-3'        (SEQ ID NO:16)

5'-TGTAAAACGACGGCCAGT-3';         (SEQ ID NO:17)
and

5'-CAGGAAACAGCTATGACC-3';         (SEQ ID NO:18)

5'-AGAAGGAGGGTGTTTGTGGGG-3';      (SEQ ID NO:19)

5'-ACCTATAGCACCCACGCCCCT-3';      (SEQ ID NO:20)

5'-GGCCGACGCTCTTGTCTAGCC-3';      (SEQ ID NO:21)

5'-CAAGGGGTTCCTAAGATGAG-3';       (SEQ ID NO:22)
and complementary sequences thereof.
```

Preferred oligonucleotides associated with the alpha-2AAR include:

```
5'-TTTACCCATCGGCTCTCCCTAC-3';     (SEQ ID NO:28)

5'GAGACACCAGGAAGAGGTTTTGG-3';     (SEQ ID NO:29)

5'-TCGTCATCATCGCCGTGTTC-3';       (SEQ ID NO:30)

5'-CGTACCACTTCTGGTCGTTGATC-3';    (SEQ ID NO:31)

5'-GCCATCATCATCACCGTGTGGGTC-3';   (SEQ ID NO:32)

5'-GGCTCGCTCGGGCCTTGCCTTTG-3';    (SEQ ID NO:33)

5'-GACCTGGAGGAGAGCTCGTCTT-3';     (SEQ ID NO:34)

5'-TGACCGGGTTCAACGAGCTGTTG-3';    (SEQ ID NO:35)

5'-GCCACGCACGCTCTTCAAATTCT-3';    (SEQ ID NO:36)

5'-TTCCCTTGTAGGAGCAGCAGAC-3';     (SEQ ID NO:37)

5'-TGTAAAACGACGGCCAGT-3';         (SEQ ID NO:38)

5'-CAGGAAACAGCTATGACC-3'          (SEQ ID NO:39)
and complementary sequences thereof.
```

Preferred oligonucleotides associated with the alpha-2CAR include:

```
5'-CCACCATCGTCGCCGTGTGGCTCATCT-3', (SEQ ID NO:48)

5'-AGGCCTCGCGGCAGATGCCGTACA-3',    (SEQ ID NO:49)

5'-AGCCGGACGAGAGCAGCGCA-3',        (SEQ ID NO:50)
and complementary sequences thereof.
```

Oligonucleotides, such as primer oligonucleotides are preferably single stranded, but may alternatively be double stranded. If double stranded, the oligonucleotide is generally first treated to separate its strands before being used for hybridization purposes or being used to prepare extension products. Preferably, the oligonucleotide is an oligodeoxyribonucleotide. Oligonucleotides may be synthesized chemically by any suitable means known in the art or derived from a biological sample, as for example, by restriction digestion. The source of the oligonucleotides is not essential to the present invention. Oligonucleotides may be labeled, according to any technique known in the art, such as with radiolabels, fluorescent labels, enzymatic labels, proteins, haptens, antibodies, sequence tags, mass tags, fluorescent polarization etc. The term "nucleotide" or nucleic acid as used herein is intended to refer to ribonucleotides, deoxyribonucleotides, acylic derivatives of nucleotides, and functional equivalents thereof, of any phosphorylation state. Functional equivalents of nucleotides are those that act as substrates for a polymerase as, for example, in an amplification method. Functional equivalents of nucleotides are also those that may be formed into a polynucleotide that retains the ability to hybridize in a sequence specific manner to a target polynucleotide.

Such oligonucleotides may be used as probes of a nucleic acid sample, such as genomic DNA, mRNA, or other suitable sources of nucleic acid. For such purposes, the oligonucleotides must be capable of specifically hybridizing to a target polynucleotide or DNA nucleic acid molecule. As used herein, two nucleic acid molecules are said to be capable of specifically hybridizing to one another if the two molecules are capable of forming an anti-parallel, double-stranded nucleic acid structure under hybridizing conditions, whereas they are substantially unable to form a double-stranded structure when incubated with a non-alpha-2BAR, a non-alpha-2AAR or a non-alpha-2CAR nucleic acid molecule under the same conditions. A nucleic acid molecule is said to be the "complement" of another nucleic acid molecule if it exhibits complete complementarity. As used herein, molecules are said to exhibit "complete complementarity" when every nucleotide of one of the molecules is complementary to a nucleotide of the other. Two molecules are said to be "substantially complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described, for example, by Sambrook, J., et al., in *Molecular Cloning, a Laboratory Manual,* 2nd Edition, Cold Spring Harbor Press, Cold Spring Harbor, N.Y. (1989), and by Haymes, B. D., et al. in *Nucleic Acid Hybridization, A Practical Approach*, IRL Press, Washington, D.C. (1985), both herein incorporated by reference). Departures from complete complementarity are therefore permissible, as long as such departures do not completely preclude the capacity of the molecules to form a double-stranded structure.

For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith for the purposes employed. However, for detection purposes, particularly using labeled sequence-specific probes, the primers typically have exact complementarity to obtain the best results. Thus, for an oligonucleotide to serve as an allele-specific oligonucleotide, it must generally be complementary in sequence and be able to form a stable double-stranded structure with a target polynucleotide under the particular environmental conditions employed.

The term "allele-specific oligonucleotide" refers to an oligonucleotide that is able to hybridize to a region of a target polynucleotide spanning the sequence, mutation, or polymorphism being detected and is substantially unable to hybridize to a corresponding region of a target polynucleotide that either does not contain the sequence, mutation, or polymorphism being detected or contains an altered sequence, mutation, or polymorphism. As will be appreciated by those in the art, allele-specific is not meant to denote an absolute condition. Allele-specificity will depend upon a variety of environmental conditions, including salt and formamide concentrations, hybridization and washing conditions and stringency. Depending on the sequences being analyzed, one or more allele-specific oligonucleotides may be employed for each target polynucleotide. Preferably, allele-specific oligonucleotides will be completely complementary to the target polynucleotide. However, departures from complete complementarity are permissible. In order for an oligonucleotide to serve as a primer oligonucleotide, however, it typically need only be sufficiently complementary in sequence to be able to form a stable double-stranded structure under the particular environmental conditions employed. Establishing environmental conditions typically involves selection of solvent and salt concentration, incubation temperatures, and incubation times. The terms "primer" or "primer oligonucleotide" as used herein refer to an oligonucleotide as defined herein, which is capable of acting as a point of initiation of synthesis when placed under conditions in which synthesis of a primer extension product which is complementary to a nucleic acid strand is induced, as for example, in a PCR reaction. As with non-primer oligonucleotides, primer oligonucleotides may be labeled, according to any technique known in the art, such as with radiolabels, fluorescent labels, enzymatic labels, proteins, haptens, antibodies, sequence tags, and the like.

In performing the methods of the present invention, the oligonucleotides or the target polynucleotide may be either in solution or affixed to a solid support. Generally, allele-specific oligonucleotides will be attached to a solid support, though in certain embodiments of the present invention allele-specific oligonucleotides may be in solution. In some such embodiments, the target polynucleotide is preferably bound to a solid support. In those embodiments where the allele-specific oligonucleotides or the target polynucleotides are attached to a solid support, attachment may be either covalent or non-covalent. Attachment may be mediated, for example, by antibody-antigen-type interactions, poly-L-Lys, streptavidin or avidin-biotin, salt-bridges, hydrophobic interactions, chemical linkages, LTV cross-ag, baking, and the like. In addition, allele-specific oligonucleotides can be synthesized directly on a solid support or attached to the solid support subsequent to synthesis. In a preferred embodiment, allele-specific oligonucleotides are affixed on a solid support such that a free 3'-OH is available for polymerase-mediated primer extension.

Suitable solid supports for the present invention include substrates constructed of silicon, glass, plastic (polystyrene, nylon, polypropylene, etc.), paper, etc. Solid supports may be formed, for example, into wells (as in 96-well dishes), plates, slides, sheets, membranes, fibers, chips, dishes, and beads. The solid support can be an array of nucleotides with different discrete nucleotide sequences at positions on the arrays. In certain embodiments of the present invention, the solid support is treated, coated, or derivatized so as to facilitate the immobilization of an allele-specific oligonucleotide or a target polynucleotide. Preferred treatments include coating, treating, or derivatizing with poly-L-Lys, streptavidin, antibodies, silane derivatives, low salt, or acid. Providing Alpha-2B, Alpha-2A and Alpha-2C Adrenergic Receptor Molecules The nucleic acid molecules or DNA encoding the alpha-2B, alpha-2A or alpha-2C adrenergic receptor molecule identified as SEQ ID NO: 1 or 2, SEQ ID NO: 24 or 25, or SEQ ID NO: 40 or 42, respectively, of the invention may be obtained from a sample. The alpha-2B, alpha-2A, and alpha-2C-adrenergic receptor molecules (amino acids) can be obtained from the sample as well.

DNA encoding the protein (alpha-2B, alpha-2A, and alpha-2C-adrenergic receptor molecules) may also be chemically synthesized by methods known in the art. Suitable methods for synthesizing the protein are described by Stuart and Young in *Solid Phase Peptide Synthesis*, Second Edition, Pierce Chemical Company (1984), *Solid Phase Peptide Synthesis, Methods Enzymol.*, 289, Academic Press, Inc, New York (1997). Suitable methods for synthesizing DNA are described by Caruthers in *Science* 230:281–285 (1985) and "DNA Structure, Part A: Synthesis and Physical Analysis of DNA," Lilley, D. M. J. and Dahlberg, J. E. (Eds.), *Methods Enzymol.*, 211, Academic Press, Inc., New York (1992).

DNA may also be synthesized by preparing overlapping double-stranded oligonucleotides, using PCR, filling in the gaps, and ligating the ends together. The DNA may be cloned in a suitable recombinant host cell and expressed. The DNA and protein may be recovered from the host cell. See, generally, Sambrook, J. et al. (Eds.), *Molecular Cloning*, Second Edition, Cold Spring Harbor Laboratory Press, Cold Spring Harbor, N.Y. (1989) and Ausubel, F. M. et al. (Eds.), *Current Protocols in Molecular Biology*, John Wiley & Sons, Inc., New York (1999).

The nucleic acid molecules or DNA encoding the alpha-2B, alpha-2A or alpha-2C adrenergic receptor molecule identified as SEQ ID NO: 1 or 2, SEQ ID NO: 24 or 25, or SEQ ID NO: 40 or 42, respectively, of the invention may be replicated and used to express recombinant protein following insertion into a wide variety of host cells in a wide variety of cloning and expression vectors. The host may be prokaryotic or eukaryotic. The DNA may be obtained from natural sources and, optionally, modified. The genes may also be synthesized in whole or in part.

Cloning vectors may comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as M13 and other filamentous single-stranded DNA phages.

Vectors for expressing proteins in bacteria, especially *E. coli*, are also known. Such vectors include the pK233 (or any of the tac family of plasmids), T7, pBluescript II, bacteriophage lamba ZAP, and lambda $P_L$ (Wu, R. (Ed.), *Recombinant DNA Methodology II, Methods Enzymol.*, Academic Press, Inc., New York, (1995)). Examples of vectors that express fusion proteins are PATH vectors described by Dieckmann and Tzagoloff in *J. Biol. Chem.* 260, 1513–1520 (1985). These vectors contain DNA sequences that encode anthranilate synthetase (TrpE) followed by a polylinker at the carboxy terminus. Other expression vector systems are based on beta-galactosidase (pEX); maltose binding protein (pMAL); glutathione S-transferase (pGST or PGEX)—see Smith, D. B. *Methods Mol. Cell Biol.* 4:220–229 (1993); Smith, D. B. and Johnson, K. S., Gene 67:31–40 (1988); and *Peptide Res.* 3:167 (1990), and TRX (thioredoxin) fusion protein (TRXFUS)—see LaVallie, R. et al., *Bio/Technology* 11:187–193 (1993). A particularly preferred plasmid of the present invention is pBC12BI.

Vectors useful for cloning and expression in yeast are available. Suitable examples are 2 μm circle plasmid, Ycp50, Yep24, Yrp7, Yip5, and pYAC3 (Ausubel, F. M. et al. (Eds.), *Current Protocols in Molecular Biology*, John Wiley & Sons, Inc., New York, (1999)).

Suitable cloning/expression vectors for use in mammalian cells are also known. Such vectors include well-known derivatives of SV-40, adenovirus, cytomegalovirus (CMV) retrovirus-derived DNA sequences. Any such vectors, when coupled with vectors derived from a combination of plasmids and phage DNA, i.e. shuttle vectors, allow for the isolation and identification of protein coding sequences in prokaryotes.

Further eukaryotic expression vectors are known in the art (e.g., P. J. Southern and P. Berg, *J. Mol. Appl. Genet.* 1:327–341 (1982); S. Subramani et al., *Mol. Cell. Biol.* 1:854–864 (1981); R. J. Kaufmann and P. A. Sharp, "Amplification And Expression Of Sequences Cotransfected with A Modular Dihydrofolate Reductase Complementary DNA Gene," *J. Mol. Biol.* 159:601–621 (1982); R. J. Kaufmann and P. A. Sharp, *Mol. Cell. Biol.* 159:601–664 (1982); S. I. Scahill et al, "Expression And Characterization Of The Product Of A Human Immune Interferon DNA Gene In Chinese Hamster Ovary Cells," *Proc. Natl. Acad. Sci. USA* 80:4654–4659 (1983); G. Urlaub and L. A. Chasin, *Proc. Natl. Acad. Sci. USA* 77:4216–4220 (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, the tet system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli*, such as *E. coli* SG-936, *E. coli* HB 101, *E. coli* W3110, *E. coli* X1776, *E. coli* X2282, *E. coli* DH1, *E. coli* DH5alphaF, and *E. coli* MRCl, Pseudomonas, Bacillus, such as *Bacillus subtilis*, and Streptomyces. Suitable eukaryotic cells include yeasts and other fungi, insect, animal cells, such as COS cells and CHO cells, human cells and plant cells in tissue culture. A particularly preferred host cell is CHO.

The alpha-2B adrenergic receptor molecule identified as SEQ ID NO: 7 or 8 can be the entire protein as it exists in nature isolated from the sample, or an antigenic, preferably immunogenic, fragment of the whole protein. The alpha-2A adrenergic receptor molecule identified as SEQ ID NO: 26 or 27 can be the entire protein as it exists in nature, or an antigenic, preferably immunogenic, fragment of the whole protein. The alpha-2C adrenergic receptor molecule identified as SEQ ID NO: 44 or 46 may be the entire protein as it exists in nature, or an antigenic, preferably immunogenic, fragment of the whole protein. Antigenic and/or immunogenic fragments of antigenic and/or immunogenic proteins may be identified by methods known in the art.

Fragments containing antigenic sequences may be selected on the basis of generally accepted criteria of potential antigenicity and/or exposure. Such criteria include the hydrophilicity and relative antigenic index, as determined by surface exposure analysis of proteins. The determination of appropriate criteria is known to those skilled in the art, and has been described, for example, by Hopp, T., Methods Enzymol., 178:571–585 Academic Press, Inc., New York (1989); Becker, Y., Virus Genes 6:79–93 (1992); Regenmortel, V and Pellequer, J. L., Pept. Res. 7:224–228 (1994); Gallet, X. et al., Prot. Eng. 8:829–834 (1995); Kyte et al., J. Mol. Biol. 157:105–132 (1982); Emini, E. A. et al., J. Virol. 55:836–839 (1985); Jameson et al., CA BIOS 4:181–186 (1988); and Karplus et al., Naturwissenschaften 72:212–213 (1985). Amino acid domains predicted by these criteria to be surface exposed are selected preferentially over domains predicted to be more hydrophobic or hidden.

Methods for isolating and identifying antigenic fragments from known antigenic proteins are described by Salfeld et al. in J. Virol. 63:798–808 (1989) and by Isola et al. in J. Virol. 63:2325–2334 (1989). An alternative means for identifying antigenic sites on protein is by the use of synthetic peptide combinatorial library or phage-display peptide library as described in Combinatorial Peptide Library Protocols, Cabilly, S. (Ed.), Humana Press, New York, 1998; Pinilla, C. et al., Pept. Res. 8:250–257 (1995); Scala, G. et al., J. Immunol. 162:6155–6161 (1999); Pereboeva, L. A. et al., J. Med. Virol. 56:105–111 (1998); and Demkowicz, W. E. et al., J. Virol. 66:386–398 (1992).

The alpha-2B, alpha-2A and alpha-2C adrenergic receptor molecules are isolated from the sample by standard methods known in the art. Some suitable methods include precipitation and liquid/chromatographic protocols such as ion exchange, hydrophobic interaction and gel filtration See, for example, Guide to Protein Purification, Deutscher, M. P. (Ed.) Methods Enzymol., 182, Academic Press, Inc., New York (1990) and Scopes, R. K. and Cantor, C. R. (Eds.), Protein Purification (3d), Springer-Verlag, N.Y. (1994).

Alternatively, purified material is obtained by separating the protein on preparative SDS-PAGE gels, slicing out the band of interest and electroeluting the protein from the polyacrylamide matrix by methods known in the art. The detergent SDS is removed from the protein by known methods, such as by dialysis or the use of a suitable column, such as the Extracti-Gel column from Pierce.

Detection of Polymorphisms

The polymorphisms of the present invention may be detected directly or indirectly using any of a variety of suitable methods. Indirect methods include detecting the nucleotides on the complementary strand of DNA or detecting nucleotide shifts upstream or downstream of the polymorphic site. One method of detection of nucleotides is by fluorescent techniques. Fluorescent hybridization probes may be constructed that are quenched in the absence of hybridization to target nucleic acid sequences. Other methods capitalize on energy transfer effects between fluorophores with overlapping absorption and emission spectra, such that signals are detected when two fluorophores are in close proximity to one another, as when captured or hybridized.

Nucleotides may also be detected by, or labeled with moieties that can be detected by, a variety of spectroscopic methods relating to the behavior of electromagnetic radiation. These spectroscopic methods include, for example, electron spin resonance, optical activity or rotation spectroscopy such as circular dichroism spectroscopy, fluorescence polarization, absorption/emission spectroscopy, ultraviolet, infrared, or mass spectroscopy, Raman spectroscopy, visible spectroscopy, and nuclear magnetic resonance spectroscopy.

The term "detection" refers to identification of a detectable moiety or moieties. The term is intended to include the ability to identify a moiety by electromagnetic characteristics, such as, for example, charge, light, fluorescence, chemiluminescense, changes in electromagnetic characteristics such as, for example, fluorescence polarization, light polarization, dichroism, light scattering, changes in refractive index, reflection, infrared, ultraviolet, and visible spectra, and all manner of detection technologies dependent upon electromagnetic radiation or changes in electromagnetic radiation. The term is also intended to include identification of a moiety based on binding affinity, intrinsic mass, mass deposition, and electrostatic properties.

Single channel detection refers to instrumentation or methods limited to simultaneous or non-simultaneous detection of a single characteristic of a detectable moiety or moieties. Bi-channel detection refers to instrumentation or methods of simultaneous or non-simultaneous detection of a characteristic of a detectable moiety or moieties. Multiple-channel detection refers to instrumentation or methods limited to simultaneous or non-simultaneous detection of or more characteristic of a detectable moiety or moieties.

One single channel platforms suitable for use with the present invention is the Luminex LabMAP system which is limited to a single assay result readout channel, having only a single laser and a single photomultiplier to image assay output. In the LabMAP platform, a single biotinylated nucleotide is labeled after a reaction run with a fluorophore for detection by flow cytometry.

Another single channel detection system suitable for use with the present invention is the BioStar platform. This detection system employs a unique thin-film preparation of a silicon surface that can be reacted for highly sensitive assay readout. As currently available, a single ELISA step with a precipitating is used to generate a signal. Signal detection, however, is achieved through a change of mass on the surface rather than by color per se, although a color change is a simple method of imaging the mass change.

Another method of detecting the nucleotide present at the polymorphic site is by comparison of the concentrations of free, unincorporated nucleotides remaining in the reaction mixture at any point after the primer extension reaction. Mass spectroscopy in general and, for example, electrospray mass spectroscopy, may be employed for the detection of unincorporated nucleotides in this embodiment. This detection method is possible because only the nucleotide(s) complementary to the polymorphic base is (are) depleted in the reaction mixture during the primer extension reaction. Thus, mass spectrometry may be employed to compare the relative intensities of the mass peaks for the nucleotides, Likewise, the concentrations of unlabeled primers may be determined and the information employed to arrive at the identity of the nucleotide present at the polymorphic site.

One particularly preferred array is the GenFlex™ Tag Array, from Affymetrix, Inc., that is comprised of capture probes for 2000 tag sequences. These are 20 mers selected from all possible 20 mers to have similar hybridization characteristics and at least minimal homology to sequences in the public databases.

Another preferred array is the addressable array that has reverse complements to the unique 5' tags of the upper and lower primers. These reverse complements are bound to the array at known positions. This type of tag hybridizes with the array under suitable hybridization conditions. By locating the bound primer in conjunction with detecting one or more extended primers, the nucleotide identity at the polymorphic site can be determined.

In one preferred embodiment of the present invention, the target nucleic acid sequences are arranged in a format that allows multiple simultaneous detections (multiplexing), as well as parallel processing using oligonucleotide arrays.

In another embodiment, the present invention includes virtual arrays where extended and unextended primers are separated on an array where the array comprises a suspension of microspheres, where the microspheres bear one or more capture moieties to separate the uniquely tagged primers. The microspheres, in turn, bear unique identifying characteristics such that they are capable of being separated on the basis of that characteristic, such as for example, diameter, density, size, color, and the like.

Suitable methods comprise direct or indirect sequencing methods, restriction site analysis, hybridization methods, nucleic acid amplification methods, gel migration methods, the use of antibodies that are specific for the proteins encoded by the different alleles of the polymorphism, or by other suitable means. Alternatively, many such methods are well known in the art and are described, for example in T. Maniatis et al., *Molecular Cloning, a Laboratory Manual, 2nd Edition*, Cold Spring Harbor Press, Cold Spring Harbor, N.Y. (1989), J. W. Zyskind et al., *Recombinant DNA Laboratory Manual*, Academic Press, Inc., New York (1988), and in R. Elles, *Molecular Diagnosis of Genetic Diseases*, Humana Press, Totowa, New Jersey (1996), each herein incorporated by reference.

Exemplary antibody molecules for detecting the alpha-2BAR, alpha-2AAR, or alpha-2CAR amino acid variants are intact immunoglobulin molecules, substantially intact immunoglobulin molecules, or those portions of immunoglobulin molecules that contain the antigen binding site. Polyclonal or monoclonal antibodies may be produced by methods conventionally known in the art (e.g., Kohler and Milstein, Nature, 256:495–497 (1975); Campbell "*Monoclonal Antibody Technology, the Production and Characterization of Rodent and Human Hybridomas*", 1985, In: "*Laboratory Techniques in Biochemistry and Molecular Biology*," Eds. Burdon et al., Volume 13, Elsevier Science Publishers, Amsterdam). The antibodies or antigen binding fragments thereof may also be produced by genetic engineering. The technology for expression of both heavy and light chain genes in *E. coli* is described in Huse et al., 1989, Science 246:1275–1281. The antibodies may also be humanized (e.g., Queen, C. et al. 1989 *Proc. Natl. Acad. Sci.* 86;10029).

Identification methods may be of either a positive-type or a negative-type. Positive-type methods determine the identity of a nucleotide contained in a polymorphic site, whereas negative-type methods determine the identity of a nucleotide not present in a polymorphic site. Thus, a wild-type site may be identified either as wild-type or not mutant. For example, at a biallelic polymorphic site where the wild-type allele contains a cytosine and the mutant allele contains adenine, a site may be positively determined to be either adenine or cytosine or negatively determined to be not adenine (and thus cytosine) or not cytosine (and thus adenine).

Alternately, if the polymorphism is a deletion, or addition then the complementary sequence can be detected. As another example, in hybridization-based assay, a target polynucleotide containing a mutated site may be identified positively by hybridizing to an allele-specific oligonucleotide containing the mutated site or negatively, by failing to hybridize to a wild-type allele-specific oligonucleotide. Similarly, a restriction site may be determined to be present or lacking.

Direct Sequencing

Direct sequencing by methods such as dideoxynucleotide sequencing (Sanger), cycle sequencing, or Maxam-Gilbert sequencing are examples of suitable methods for determining the identity of a nucleotide at a polymorphic site of a target polynucleotide. Such methods are widely known in the art and are discussed at length, in the above-cited texts.

Both the dideoxy-mediated method and the Maxam-Gilbert method of DNA sequencing require the prior isolation of the DNA molecule which is to be sequenced. The sequence information is obtained by subjecting the reaction products to electrophoretic analysis (typically using polyacrylamide gels). Thus, a sample is applied to a lane of a gel, and the various species of nested fragments are separated from one another by their migration velocity through the gel. The number of nested fragments which can be separated in a single lane is approximately 200–300 regardless of whether the Sanger or the Maxam-Gilbert method is used. Thus, in order to identify a nucleotide at a particular polymorphic site in a target polynucleotide, extraneous sequence information is typically produced. The chief advantage of direct sequencing lies in its utility for locating previously unidentified polymorphic sites.

One of the problems that has encumbered the development of useful assays for genetic polymorphisms is that in many cases, it is desirable to determine the identity of multiple polymorphic loci. This frequently requires sequencing significant regions of the genome or performing multiple assays with an individual patient sample.

Restriction Site Analysis

Restriction enzymes are specific for a particular nucleotide sequence. In certain embodiments of the present invention, the identity of a nucleotide at a polymorphic site is determined by the presence or absence of a restriction enzyme site. A large number of restriction enzymes are known in the art and, taken together, they are capable of recognizing at least one allele of many polymorphisms.

This feature of restriction enzymes may be utilized in a variety of methods for identifying a polymorphic site. Restriction fragment length polymorphism (RFLP) analysis is an example of a suitable method for identifying a polymorphic site with restriction enzymes (Lentes et al., *Nucleic Acids Res.* 16:2359 (1988); and C. K. McQuitty et al., *Hum. Genet.* 93:225 (1994)). In RFLP analysis, at least one target polynucleotide is digested with at least one restriction enzyme and the resultant "restriction fragments" are separated based on mobility in a gel. Typically, smaller fragments migrate faster than larger fragments. Consequently, a target polynucleotide that contains a particular restriction enzyme recognition site will be digested into two or more smaller fragments, which will migrate faster than a larger fragment lacking the restriction enzyme site. Knowledge of the nucleotide sequence of the target polynucleotide, the nature of the polymorphic site, and knowledge of restriction enzyme recognition sequences guide the design of such assays.

Hybridization

Several suitable hybridization-based methods for identifying a nucleotide at a polymorphic site have been described. Generally, allele-specific oligonucleotides are utilized in performing such hybridization-based methods. Preferably, allele-specific oligonucleotides are chosen that are capable of specifically hybridizing to only one allele of an alpha-2B, an alpha-2A, or an alpha-2C molecule at a region comprising a polymorphic site. In those embodiments wherein more than one polymorphic site is identified, sets of allele-specific oligonucleotides are preferably chosen that have melting temperatures within 5° C. of each other when hybridizing to their complete complement. Most preferably, such sets of allele-specific oligonucleotides are chosen so as to have melting temperatures within 20° C. of each other. Examples of suitable hybridization methods are described in standard manuals such as Molecular Cloning, A Laboratory Manual (2nd Ed., Sambrook, Fritsch and Maniatis, Cold Spring Harbor); and Current Protocols in Molecular Biology (Eds. Ausubel, Brent, Kingston, More, Feidman, Smith and Stuhl, Greene Publ. Assoc., Wiley-Interscience, NY, N.Y., 1992) or that are otherwise known in the art. Examples of preferred hybridization methods include Southern, northern, and dot blot hybridizations, allele-specific oligonucleotide hybridizations (Hall et al., *The Lancet* 345:1213–1214 (1995)), reverse dot blot hybridizations (Sakai et al., *Nucl. Acids. Res.* 86:6230–6234 (1989)), DNA chip hybridizations (Drmanac et al., U.S. Pat. No. 5,202,231), and hybridizations to allele-specific oligonucleotides.

Macevicz (U.S. Pat. No. 5,002,867), for example, describes a method for deriving nucleic acid sequence information via hybridization with multiple mixtures of oligonucleotide probes. In accordance with such method, the sequence of a target polynucleotide is determined by permitting the target to sequentially hybridize with sets of probes having an invariant nucleotide at one position, and variant nucleotides at other positions. The Macevicz method determines the nucleotide sequence of the target by hybridizing the target with a set of probes, and then determining the number of sites that at least one member of the set is capable of hybridizing to the target (i.e. the number of "matches"). This procedure is repeated until each member of a sets of probes has been tested.

Polymerase-Mediated Primer Extension

The "Genetic Bit Analysis" ("GBA") method disclosed by Goelet, P. et al. (WO92/15712, and U.S. Pat. Nos. 5,888,819 and 6,004,744, all herein incorporated by reference), is a preferred method for determining the identity of a nucleotide at a predetermined polymorphic site in a target polynucleotide. The target polynucleotide can be, for example, nucleic acids encoding the alpha-2B, alpha-2C, or alpha-2A adrenergic receptor molecule or complements or fragments thereof. GBA is a method of polymorphic site interrogation in which the nucleotide sequence information surrounding a polymorphic site in a target nucleic acid sequence is used to design an oligonucleotide primer that is complementary to a region immediately adjacent to at the 3' or 5' end of the target polynucleotide, but not including, the variable nucleotide(s) in the polymorphic site of the target polynucleotide. The target polynucleotide is isolated from the biological sample and hybridized to the interrogating primer. In some embodiments of the present invention, following isolation, the target polynucleotide may amplified by any suitable means prior to hybridization to the interrogating primer. The primer is extended by a single labeled terminator nucleotide, such as a dideoxynucleotide, using a polymerase, often in the presence of one or more chain terminating nucleoside triphosphate-precursors (or suitable, analogs). A detectable signal is thereby produced.

For example, to detect the polymorphic site on target nucleic acids encoding the alpha-2BAR, a primer oligonucleotide complementary to a region of SEQ ID NO:1 can be hybridized at the primer's 3' end to a region up to and including, for example, nucleotide position number 904 of SEQ ID NO:1. If the primer is extended at its 3' end by a single labeled terminator nucleotide, such as for example the dideoxynucleotide ddTTP, using a polymerase, a detectable signal is produced indicating the complementary nucleotide A at nucleotide position 903. This indicates the wild-type alpha-2BAR and thus the polymorphic alpha-2BAR is identified.

To detect the polymorphic site on target nucleic acids encoding the alpha-2BAR, a primer oligonucleotide complementary to a region of SEQ ID NO: 2 can be hybridized at the primer's 3' end to a region up to and including, for example, nucleotide position number 904 of SEQ ID NO: 2. If the primer is extended at its 3' end by a single labeled terminator nucleotide, such as for example the dideoxynucleotide ddCTP, using a polymerase, a detectable signal is produced indicating the complementary nucleotide G at nucleotide position 903. This indicates the mutant alpha-2BAR shown and thus the polymorphic alpha-2BAR is identified.

For example, to detect the polymorphic site on target nucleic acids encoding the alpha-2AAR, a primer oligonucleotide complementary to a region of SEQ ID NO:24 can be hybridized at the primer's 3' end to a region up to and including, for example, nucleotide position number 754 of SEQ ID NO:24. If the primer is extended at its 3' end by a single labeled terminator nucleotide, such as for example the dideoxynucleotide ddGTP, using a polymerase, a detectable signal is produced indicating the complementary nucleotide C at nucleotide position 753. This indicates the wild-type alpha-2AAR shown in FIG. 5A (bolded arrow) and thus the polymorphic alpha-2AAR is identified.

For example, to detect the polymorphic site on target nucleic acids encoding the alpha-2CAR, a primer oligonucleotide complementary to a segment of SEQ ID NO:40 can be hybridized at the primer's 3' end to a region up to and including, for example, nucleotide position number 972 of SEQ ID NO:40. If the primer is extended at its 3' end by a single labeled terminator nucleotide, such as for example the dideoxynucleotide ddGTP, using a polymerase, a detectable signal is produced indicating the complementary nucleotide C at nucleotide position 971. This indicates the twelve nucleotide deletion shown in FIG. 11B (bolded arrow) and thus the polymorphic alpha-2CAR is identified.

In some embodiments of the present invention, the oligonucleotide is bound to a solid support prior to the extension reaction. In other embodiments, the extension reaction is performed in solution and the extended product is subsequently bound to a solid support.

In an alternate sub-embodiment of GBA, the primer is detectably labeled and the extended terminator nucleotide is modified so as to enable the extended primer product to be bound to a solid support. An example of this would be where the primer is fluorescently labeled and the terminator nucleotide is a biotin-labeled terminator nucleotide and the solid support is coated or derivatized with avidin or streptavidin. In such embodiments, an extended primer would thus be enabled to bind to a solid support and non-extended primers would be unable to bind to the support, thereby producing a detectable signal dependent upon a successful extension reaction.

Ligase/polymerase mediated genetic bit analysis (U.S. Pat. Nos. 5,679,524, and 5,952,174, both herein incorporated by reference) is another example of a suitable polymerase mediated primer extension method for determining the identity of a nucleotide at a polymorphic site. Ligase/polymerase GBA utilizes two primers. Generally, one primer is detectably labeled, while the other is designed to be affixed to a solid support. In alternate embodiments of ligase/polymerase GBA, extended nucleotide is detectably labeled. The primers in ligase/polymerase GBA are designed to hybridize to each side of a polymorphic site, such that there is a gap comprising the polymorphic site. Only a successful extension reaction, followed by a successful ligation reaction enables the production of the detectable signal. The method offers the advantages of producing a signal with considerably lower background than is possible by methods employing only hybridization or primer extension alone.

The present invention includes an alternate method for determining the identity of a nucleotide at a predetermined polymorphic site in a target polynucleotide. This method is described in Söderlund et al., U.S. Pat. No. 6,013,431, the entire disclosure is herein incorporated by reference. In this alternate method, the polymorphic site is interrogated where nucleotide sequence information surrounding a polymorphic site in a target nucleic acid sequence is used to design an oligonucleotide primer that is complementary to a region flanking the 3' or 5' end of the target polynucleotide, but not including, the variable nucleotide(s) in the polymorphic site of the target polynucleotide. The target polynucleotide is isolated from the biological sample and hybridized to the interrogating primer. In some embodiments of this method, following isolation, the target polynucleotide may be amplified by any suitable means prior to hybridization to the interrogating primer. The primer is extended, using a polymerase, often in the presence of a mixture of at least one labeled deoxynucleotide and one or more chain terminating nucleoside triphosphate-precursors (or suitable, analogs). A detectable signal is thereby produced upon incorporation of the labeled deoxynucleotide into the primer.

Cohen, D. et al. (PCT Application W091/02087) describes another example of a suitable method for determining the identity of a polymorphic site, wherein dideoxynucleotides are used to extend a single primer by a single nucleotide in order to determine the sequence at a desired locus. Ritterband, M., et al., (PCT Application W095/17676) describes an apparatus for the separation, concentration and detection of such target molecules in a liquid sample. Cheeseman, P. C. (U.S. Pat. No. 5,302,509) describes a related method of determining the sequence of a single stranded DNA molecule. The method of Cheeseman employs fluorescently labeled 3'-blocked nucleotide triphosphates with each base having a different fluorescent label.

Wallace et al. (PCT Application W089/10414) describes multiple PCR procedures which can be used to simultaneously amplify multiple regions of a target by using allele specific primers. By using allele specific primers, amplification can only occur if a particular allele is present in a sample.

Several other suitable primer-guided nucleotide incorporation procedures for assaying polymorphic sites in DNA have been described (Komher, J. S. et al., *Nucl. Acids. Res.* 17:7779–7784 (1989); Sokolov, B. P., *Nucl. Acids Res.* 18:3671 (1990); Syvanen, A.-C., et al., *Genomics* 8:684–692 (1990); Kuppuswamy, M. N. et al., *Proc. Natl. Acad. Sci. (U.S.A.)* 88:1143–1147 (1991); Bajaj et al. (U.S. Pat. No. 5,846,710); Prezant, T. R. et al., *Hum. Mutat.* 1:159–164 (1992); Ugozzoli, L. et al., *GATA* 9:107–112 (1992); Nyrén, P. et al., *Anal. Biochem.* 208:171–175 (1993)). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide will result in signals that are proportional to the length of the run (Syvanen, A.-C., et al., *Amer. J. Hum. Genet.* 52:46–59 (1993)). Such a range of locus-specific signals could be more complex to interpret, especially for heterozygotes, compared to the simple, ternary (2:0, 1:1, or 0:2) class of signals produced by the GBA method.

Amplification

In certain embodiments of the present invention, the detection of polymorphic sites in a target polynucleotide may be facilitated through the use of nucleic acid amplification methods. Such methods may be used to specifically increase the concentration of the target polynucleotide (i.e., sequences that span the polymorphic site, or include that site and sequences located either distal or proximal to it). Such amplified molecules can be readily detected by gel electrophoresis, or other means.

The most preferred method of achieving such amplification employs PCR (e.g., Mullis, et al., U.S. Pat. No. 4,965,188), using primer pairs that are capable of hybridizing to the proximal sequences that define or flank a polymorphic site in its double-stranded form.

In some embodiments of the present invention, the amplification method is itself a method for determining the identity of a polymorphic site, as for example, in allele-specific PCR (J. Turki et al., *J. Clin. Invest.* 95:1635–1641 (1995)). In allele-specific PCR, primer pairs are chosen such that amplification is dependent upon the input template nucleic acid containing the polymorphism of interest. In such embodiments, primer pairs are chosen such that at least one primer is an allele-specific oligonucleotide primer. In some sub-embodiments of the present invention, allele-specific primers are chosen so that amplification creates a restriction site, facilitating identification of a polymorphic site. In other embodiments of the present invention, amplification of the target polynucleotide is by multiplex PCR (Wallace et al. (PCT Application W089/10414)). Through the use of multiplex PCR, a multiplicity of regions of a target polynucleotide may be amplified simultaneously. This is particularly advantageous in those embodiments wherein greater than a single polymorphism is detected.

In lieu of PCR, alternative methods, such as the "Ligase Chain Reaction" ("LCR") may be used (Barany, F., *Proc. Natl. Acad. Sci. (U.S.A.)* 88:189–193 (1991)). LCR uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resultant product serves as a template in subsequent amplification cycles, resulting in an exponential amplification of the desired sequence.

In accordance with the present invention, LCR can be performed using oligonucleotides having sequences derived from the same strand, located proximal and distal to the polymorphic site. In one embodiment, either oligonucleotide is designed so as to include the actual polymorphic site of the polymorphism. In such an embodiment, the reaction conditions are selected such that the oligonucleotides can be ligated together only if the target molecule contains the specific nucleotide in the polymorphic site that is complementary to the polymorphic site present on the oligonucleotide. In an alternative embodiment, the oligonucleotides will not include the polymorphic site, such that when they hybridize to the target molecule, a "gap" of at least one nucleotide is created (see, Segev, D., PCT Application W090/01069 and U.S. Pat. No. 6,004,826). This gap is then "filled" with complementary dNTPs (as mediated by DNA polymerase), or by an additional pair of oligonucleotides. Thus, at the end of each cycle, each single strand has a complement capable of serving as a target during the next cycle and exponential amplification of the desired sequence is obtained.

The "Oligonucleotide Ligation Assay" ("OLA") (Landegren, U. et al., *Science* 241:1077–1080 (1988)) shares certain similarities with LCR and is also a suitable method for analysis of polymorphisms. The OLA protocol uses two oligonucleotides, which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson, D. A. et al. have described a nucleic acid detection assay that combines attributes of PCR and OLA (Nickerson, D. A. et al., *Proc. Natl. Acad Sci. (U.S.A.)* 87:8923–8927 (1990)). In this method, PCR is used to achieve the exponential amplification of target DNA, which is then detected using OLA.

Schemes based on ligation of two (or more) oligonucleotides in the presence of nucleic acid having the sequence of the resulting "dioligonucleotide", thereby amplifying the dioligonucleotide, are known (Wu, D. Y. et al., *Genomics* 4:560 (1989); Adams, C., W094/03630), and are also suitable methods for the purposes of the present invention.

One convenient method for identifying genetic polymorphisms is called random amplified polymorphic DNA ("RAPD"). It requires no probe DNA and no advance information about the genome of the organism, but uses a set of PCR primers of 8 to 10 bases whose sequence is random. The random primers are tried singly or in pairs in PCR reactions, and since the primers are short, they often anneal to the target DNA at multiple sites. Some primers anneal in the proper orientation and at a suitable distance from each other to support amplification of the unknown sequence between them. Among the set of fragments are ones that can be amplified from some genomic DNA samples but not from others, which means that the presence or absence of the fragment is polymorphic in the population of organisms. An important feature of RAPDs and other detection methods based on PCR amplification is that presence of the fragment is dominant to absence of the fragment. Thus, if one allele (+) supports amplification but the alternative allele (−) does not, then DNA from the genotypes +/+ and +/− will support amplification equally well, whereas DNA from the genotype −/− will not support amplification. The + allele is therefore dominant to the − allele in regard to the corresponding RAPD fragment.

Other known nucleic acid amplification procedures include transcription-based amplification systems (Malek, L. T. et al., U.S. Pat. No. 5,130,238; Davey, C. et al., European Patent Application 329,822; Schuster et al., U.S. Pat. No. 5,169,766; Miller, H. I. et al., PCT-Application W089/06700; Kwoh, D. et al., *Proc. Natl. Acad Sci. (U.S.A.)* 86:1173 Z1989); Gingeras, T. R. et al., PCT Application W088/10315)), or isothermal amplification methods (Walker, G. T. et al., *Proc. Natl. Acad Sci. (U.S.A.)* 89:392–396 (1992)) may also be used.

Gel Migration

Single strand conformational polymorphism (SSCP; M. Orita et al., *Genomics* 5:874–879 (1989);Humphfies et al., *In: Molecular Diagnosis of Genetic Diseases, R. Elles*, ed. pp321–340 (1996)) and temperature gradient gel electrophoresis (TGGE; R. M. Wartell et al., *Nucl. Acids Res.* 18:2699–2706 (1990)) are examples of suitable gel nmigration-based methods for determining the identity of a polymorphic site. In SSCP, a single strand of DNA will adopt a conformation that is uniquely dependent of its sequence composition. This conformation is usually different, if even a single base is changed. Thus, certain embodiments of the present invention, SSCP may be utilized to identify polymorphic sites, as wherein amplified products (or restriction fragments thereof) of the target polynucleotide are denatured, then run on a non-denaturing gel. Alterations in the mobility of the resultant products are thus indicative of a base change. Suitable controls and knowledge of the "normal" migration patterns of the wild-type alleles may be used to identify polymorphic variants.

Temperature gradient gel electrophoresis (TGGE) is a related procedure, except that the nucleic acid sample is run on a denaturing gel. In embodiments of the present invention utilizing TGGE to identify a polymorphic site, the amplified products (typically PCR products) are electrophoresed over denaturing polyacrylamide gel, wherein the temperature gradient is optimized for separation of the target polynucleotide segments (E. Reihsaus et al., *Am. J. Respir. Cell Mol. Biol.* 8:334–339 (1993), herein incorporated by reference). This method is able to detect single base changes in the target polynucleotide sequence.

Kits of the Present Invention

The present invention provides diagnostic and therapeutic kits that include at least one primer for detecting at least one polymorphism in nucleic acids encoding an alpha-2B, alpha-2A or alpha-2C adrenergic receptor molecule. Preferably, the kit includes a container having an oligonucleotide comprising a region of SEQ ID NOs: 1 or 2, SEQ ID NOs: 24 or 25, or SEQ ID NOs: 40 or 42 or complement thereof for detecting the polymorphism as described. In one embodiment, the kit includes primers for amplifying regions of nucleic acids encoding the alpha-2B, alpha-2A or alpha-2C adrenergic receptor molecule where at least one of the polymorphisms is found, such as for example SEQ ID NOs: 1 or 2, SEQ ID NOs: 24 or 25, or SEQ ID NOs: 40 or 42, respectively. In an alternate embodiment, the kit includes allele-specific oligonucleotides, specific for both mutant and wild-type alleles of at least one polymorphism. The kit may also contain sources of "control" target polynucleotides, as positive and negative controls. Such sources may be in the form of patient nucleic acid samples, cloned target polynucleotides, plasmids or bacterial strains carrying positive and negative control DNA. Kits according to the invention can include one or more containers, as well as additional reagent(s) and/or active and/or inert ingredient(s) for performing any variations on the methods of the invention. Exemplary reagents include, without limitation, one or more primers, one or more terminator nucleotides, such as dideoxynucleotides, that are labeled with a detectable marker. The kits can also include instructions for mixing or combining ingredients or use.

The invention also provides diagnostic and experimental kits which include monospecific antibodies that enable the detection, purification and/or separation of alpha-2B, alpha-2A, or alpha-2C adrenergic receptor molecules or fragments thereof in a specific and reproducible manner. In these kits, the antibodies may be provided with means for binding to detectable marker moieties or substrate surfaces. Alternatively, the kits may include the antibodies already bound to marker moieties or substrates. The kits may further include positive and/or negative control reagents as well as other reagents for adapting the use of the antibodies to particular experimental and/or diagnostic techniques as desired. The kits may be prepared for in vivo or in vitro use, and may be particularly adapted for performance of any of the methods of the invention, such as ELISA. For example, kits containing antibody bound to multi-well microtiter plates can be manufactured.

Genotyping and Haplotyping Methods

The polymorphic sites of the present invention occurring in the polynucleotide encoding alpha-2B, alpha-2A, or alpha-2C adrenergic receptor gene can be detected by any of the above methods and used to determine the genotype. As used herein, the term "genotyping" refers to determining the presence, absence or identity of a polymorphic site in a target nucleic acid (identified as SEQ ID NOs: 1 or 2; SEQ ID NOs: 24 or 25; or SEQ ID NOs: 40 or 42). Preferably, the genotyping is performed on two copies of the alpha-2B, alpha-2A, or alpha-2C adrenergic receptor gene.

In one embodiment, genotyping involves obtaining a sample containing the target nucleic acid, treating the sample to obtain single stranded nucleic acids, if such nucleic acid is double-stranded, so as to obtain unpaired nucleotide bases spanning the specific position. If the target nucleic acid is single-stranded, this step is not necessary. The sample containing the target nucleic acid is contacted with an oligonucleotide under hybridizing conditions. The oligonucleotide is capable of hybridizing with a stretch of nucleotide bases present in the target nucleic acid, adjacent to the polymorphic site to be identified (e.g., deletion, insertion, mutation, or a single nucleotide polymorphisms), so as to form a duplex between the oligonucleotide and the target nucleic acid. When the oligonucleotide is "immediately adjacent" the polymorphic site to be identified, the oligonucleotide hybridizes with the target nucleic acid in such a way that either the 3' or 5' end of the oligonucleotide is complementary to a nucleotide on the target nucleic acid that is located immediately 5' or 3', respectively, of the polymorphic site to be identified. It is also contemplated herein that the oligonucleotide can be a fragment complementary to SEQ ID NO: 1 or 2, SEQ ID NO: 24 or 25, or SEQ ID NO: 40 or 42 and not immediately adjacent to the polymorphic site to be identified, such that the 3' end of the oligonucleotide is 1 up to 50, preferably 1 up to 20, nucleotides upstream or downstream from the polymorphic site to be identified in the target nucleic acid.

As used herein, upstream includes that part of a strand of DNA or RNA molecule that is towards the 5' end of the polymorphic site or site of interest. For example, upstream of the polymorphic site of the alpha-2B target polynucleotide (nucleotide positions 901 to 909 of SEQ ID NO: 1 or 2) includes nucleotide positions 880 to 900. Also, for example, upstream of the polymorphic site of the alpha-2A target polynucleotide (nucleotide position 753 of SEQ ID NO: 24 or 25) includes nucleotide positions 752 to 732. Also, for example, upstream of the polymorphic site of the alpha-2C target polynucleotide (nucleotide positions 964 to 975 of SEQ ID NO: 40 or 42) includes nucleotide positions 951 to 963. Downstream includes that part of a strand of DNA or RNA molecule lying towards the 3' end of the polymorphic site or site of interest. For example, downstream of the polymorphic site of the alpha-2B target polynucleotide (nucleotide positions 901 to 909 of SEQ ID NO: 1 or 2) includes nucleotide positions 910 to 930. Also, for example, downstream of the polymorphic site of the alpha-2A target polynucleotide (nucleotide position 753 of SEQ ID NO: 24 or 25) includes nucleotide positions nucleotide positions 754 to 764. Also, for example downstream of the polymorphic site of the alpha-2C target polynucleotide (nucleotide positions 964 to 975 of SEQ ID NO: 40 or 42) includes nucleotide positions 976 to 988.

In one preferred embodiment of the present invention, to detect the polymorphic site on target nucleic acids encoding the alpha-2BAR, a primer oligonucleotide complementary to a region of SEQ ID NO:1 can be hybridized at the primer's 3' end to a region up to and including, for example, nucleotide position number 902 of SEQ ID NO:1. If the primer is extended at its 3' end by a single labeled terminator nucleotide, such as for example the dideoxynucleotide ddTTP, using a polymerase, a detectable signal is produced indicating the complementary nucleotide A at nucleotide position 903. This indicates the wild-type alpha-2BAR and thus the polymorphic alpha-2BAR is identified.

To detect the polymorphic site on target nucleic acids encoding the alpha-2BAR, a primer oligonucleotide complementary to a region of SEQ ID NO: 2 can be hybridized at the primer's 3' end to a region up to and including, for example, nucleotide position number 904 of SEQ ID NO: 2. If the primer is extended at its 3' end by a single labeled terminator nucleotide, such as for example the dideoxynucleotide ddCTP, using a polymerase, a detectable signal is produced indicating the complementary nucleotide G at nucleotide position 903. This indicates the mutant alpha-2BAR and thus the polymorphic alpha-2BAR is identified. The above described methods are useful in determining the alpha-2BAR genotype or haplotype. In one embodiment, the present invention provides a method of genotyping an alpha-2B adrenergic receptor gene comprising: obtaining a sample having a polynucleotide encoding an alpha-2B-adrenergic receptor molecule comprising SEQ ID NOs: 1 or 2 or fragment or complement of the polynucleotide; and detecting in the sample a polymorphic site comprising nucleotide positions 901 to 909 of SEQ ID Nos: 1 or 2 or fragment or complement thereof.

In the most preferred embodiment, the present invention includes methods of genotyping nucleic acids encoding an alpha-2B, alpha-2A, or alpha-2C adrenergic receptor molecule from a sample of an individual which includes isolating from the individual, the sample having a polynucleotide encoding the alpha-2B, alpha-2A, or alph-2C adrenergic receptor molecule identified as SEQ ID NO: 1 or 2, SEQ ID NO: 24 or 25, or SEQ ID NO: 40 or 42, respectively, or fragment or complement thereof; incubating the polynucleotide with at least one oligonucleotide, the oligonucleotide having a nucleotide sequence that is complementary to a region of the polynucleotide, and which, when hybridized to the region permits the identification of the nucleotide present at a polymorphic site of the polynucleotide, wherein the incubation is under conditions sufficient to allow specific hybridization to occur between complementary nucleic acid molecules; permitting the hybridization to occur; and identifying the polymorphic site to obtain the genotype of the individual. A genotype includes a 5' to 3' sequence of nucleotide pair(s) found at one or more polymorphic sites in a locus on a pair of homologous chromosomes in an individual.

In one embodiment of the present invention, to detect the polymorphic site on target nucleic acids encoding the alpha-2AAR, a primer oligonucleotide complementary to a region of SEQ ID NO:24 can be hybridized at the primer's 3' end to a region up to and including, for example, nucleotide position number 754 of SEQ ID NO:24. If the primer is extended at its 3' end by a single labeled terminator nucleotide, such as for example the dideoxynucleotide ddGTP, using a polymerase, a detectable signal is produced indicating the complementary nucleotide C at nucleotide position 753. This indicates the wild-type alpha-2AAR shown in FIG. 5A (bolded arrow) and thus the polymorphic alpha-2AAR is identified.

The present invention includes a method for haplotyping an alpha-2B adrenergic receptor gene comprising: obtaining a sample having a polynucleotide encoding an alpha-2B-adrenergic receptor molecule comprising SEQ ID NOs: 1 or 2 or fragment or complement of the polynucleotide; detecting in the sample a polymorphic site comprising nucleotide positions 901 to 909 of SEQ ID NOs: 1 or 2 or fragment or complement thereof on one copy of the alpha-2B-adrenergic receptor gene; and determining the identity of an additional polymorphic site on the copy of the alpha-2B-adrenergic receptor gene.

As used herein, haplotyping includes determining the identity of two or more polymorphic sites in a locus on a single chromosome from a single individual. Haplotypes include 5' to 3' sequence of nucleotides found at two or more polymorphic sites in a locus on a single chromosome from an individual. The preferred polymorphic sites are discussed above.

Once the haplotype or genotype is determined in the individual, this information can be compared to any particular alpha-2BAR, alpha-2AAR or alpha-2CAR genotype or haplotype found in a population. In a preferred embodiment, the alpha-2BAR, alpha-2AAR or alpha-2CAR genotype may also comprise the nucleotide pair(s) detected at one or more additional alpha-2BAR, alpha-2AAR or alpha-2CAR polymorphic sites. The population may be a reference population, a family population, a same sex population, a population group, a trait population (e.g., a group of individuals exhibiting a trait of interest such as a medical condition or response to a therapeutic treatment i.e. drug). Population groups include a group of individuals sharing a common ethno-geographic origin. Reference populations include a group of subjects or individuals who are predicted to be representative of the genetic variation found in the general population. Preferably, the reference population represents the genetic variation in the population at a certainty level of at least 85%, preferably at least 90%, more preferably at least 95% and even more preferably at least 99%.

Frequency data for such alpha-2BAR, alpha-2AAR or alpha-2CAR genotypes or haplotypes in reference and trait populations are useful for identifying an association between a trait and an alpha-2BAR, alpha-2AAR or alpha-2CAR polymorphism, an alpha-2BAR, alpha-2AAR or alpha-2CAR genotype or an alpha-2BAR, alpha-2AAR or alpha-2CAR haplotype. The trait may be any detectable phenotype, including but not limited to genetic predisposition to a disease or response to a treatment, such as for example, agonist or antagonist. These data can be used to determine a measurable or baseline effect of the agonist or antagonist correlated with the polymorphism, genotype or haplotype.

In one embodiment, the method of the present invention includes obtaining data on the frequency of the alpha-2BAR, alpha-2AAR, or alpha-2CAR polymorphism, alpha-2BAR, alpha-2AAR or alpha-2CAR genotype or alpha-2BAR, alpha-2AAR or alpha-2CAR haplotype of interest in a reference population as well as in a population exhibiting the trait. Frequency data for one or both of the reference and trait populations may be obtained by genotyping or haplotyping each individual in the populations using one of the methods described herein. In another embodiment, the frequency data for the reference and/or trait populations is obtained by accessing previously determined frequency data, which may be in written or electronic form. For example, the frequency data may be present in a database that is accessible by a computer. Once the frequency data is obtained, the frequencies of the alpha-2BAR, alpha-2AAR or alpha-2CAR polymorphism, alpha-2BAR, alpha-2AAR, or alpha-2CAR genotype or alpha-2BAR, alpha-2AAR or alpha-2CAR haplotype of interest are compared in the reference and trait populations. If an alpha-2BAR, alpha-2AAR or alpha-2CAR polymorphism, alpha-2BAR, alpha-2AAR, or alpha-2CAR genotype or alpha-2BAR, alpha-2AAR or alpha-2CAR haplotype is more frequent in the trait population than in the reference population to a statistically significant degree, then the trait is predicted to be associated with that alpha-2BAR, alpha-2AAR or alpha-2CAR polymorphism, alpha-2BAR, alpha-2AAR, or alpha-2CAR genotype or alpha-2BAR, alpha-2AAR or alpha-2CAR haplotype.

Transgenic Animals

The knowledge of the alpha-2A-adrenergic receptor molecule identified as amino acids SEQ ID NO: 26 or 27 of the invention, together with the cloning and sequencing of the nucleic acids encoding the alpha-2A-adrenergic receptor molecule identified as SEQ ID NO: 24 or 25, enables other applications of the invention. The knowledge of the alpha-2C-adrenergic receptor molecule identified as amino acids SEQ ID NO: 5 or 7 of the invention, together with the cloning and sequencing of the nucleic acids encoding the alpha-2C-adrenergic receptor molecule identified as SEQ ID NO: 1 or 3, enables other applications of the invention. For example, genetically altered animals can be constructed using techniques, such as transgenesis and gene ablation with substitution, to express alpha-2B, alpha-2A or alpha-2C adrenergic receptor gene products. Various such techniques are known, and certain of these techniques can yield heritability of the transgene. See, e.g., Pinkert et al. (1995) for an overview of these techniques, and the documents cited there for greater detail. Also, the production of transgenic non-human animals is disclosed U.S. Pat. Nos. 5,175,385, 5,175,384, 5,175,838 and 4,736,866 which are incorporated herein by reference.

Briefly, an animal can be transformed by integration of an expressible transgene comprising a heterologous alpha-2B, alpha-2A or alpha-2C adrenergic receptor-related nucleic acid sequence into the genome of the animal. Preferably the transgene is heritable. Such a transgenic animal can then be used as an in vivo model for production of the alpha-2b, alpha-2A, or alpha-2C adrenergic receptor molecule in the species from which the gene encoding the alpha-2B, alpha-2A, or alpha-2C adrenergic receptor molecule is derived. Of particular importance, of course, is the development of animal models for human alpha-2B, alpha-2A or alpha-2C adrenergic receptor activity. Such transgenic animal models would express, for example, the mutant alpha-2B, alpha-2A or alpha-2C adrenergic receptor molecule normally expressed in humans, and would be capable of being used as in vivo pharmacologic models to study polymorphisms and effects on receptor activity. In gene ablation with substitution (also called "hit and run" or "tag and replace") the murine alpha-2B, alpha-2A or alpha-2C gene is removed and replaced with the human wild-type or mutant alpha-2B, alpha-2A or alpha-2C gene.

Animals suited for transgenic manipulation include domesticated animals, simians and humans. Domesticated animals include those of the following species: canine; feline; bovine; equine; porcine; and murine.

In one exemplary approach a genetically altered test animal is administered a putative alpha-2B, alpha-2A or alpha-2C adrenergic receptor agonist or antagonist. Following a time sufficient to produce a measurable effect in an otherwise untreated animal, binding and activity of the agonist or antagonist is measured by methods known in the art, such as radio-ligand binding assays, adenyl cyclase, MAP kinase or inositol phosphate activity. A lower than normal rate of binding or activity indicates that the receptor is defective.

Antibodies

The present invention provides antibodies raised against the alpha-2A-adrenergic receptor protein identified as SEQ ID NO: 26 or 27 or fragment thereof. Such antibodies can bind, preferably specifically, with amino acid position 251 of SEQ ID NO: 26 or 27. These antibodies form the basis of a diagnostic test or kits. An "antibody" in accordance with the present specification is defined broadly as a protein that binds specifically to an epitope, such as for example the lysine at amino acid position 251 of SEQ ID NO: 27 or fragment thereof. The present invention provides antibodies raised against the alpha-2C-adrenergic receptor protein identified as SEQ ID NO: 28 or 30 or fragment thereof. Such antibodies can bind, preferably specifically, with an epitope on SEQ ID NO: 28 or 30 or fragment thereof. These antibodies form the basis of a diagnostic test or kits. An "antibody" in accordance with the present specification is defined broadly as a protein that binds specifically to an epitope, such as for example peptides SEQ ID NO: 29 or 31 or fragment thereof. The antibody may be polyclonal or monoclonal. Antibodies further include recombinant polyclonal or monoclonal Fab fragments prepared in accordance with the method of Huse et al., Science 246, 1275–1281 (1989) and Coligan, J. E. et al. (Eds.) Current Protocols in Immunology, Wiley Intersciences, New York, (1999).

Preparing Antibodies

Polyclonal antibodies are isolated from mammals that have been innoculated with the protein or a functional analog, such as in accordance with methods known in the art (Coligan, J. E, et al. (Eds.), Current Protocols in imunology, Wiley Intersciences, New York, (1999)). Briefly, polyclonal antibodies may be produced by injecting a host mammal, such as a rabbit, mouse, rat, or goat, with the protein or a fragment thereof capable of producing antibodies that distinguish between mutant and wild-type protein. The peptide or peptide fragment injected may contain the wild-type sequence or the mutant sequence. Sera from the mammal are extracted and screened to obtain polyclonal antibodies that are specific to the peptide or peptide fragment.

The antibodies are preferably monoclonal. Monoclonal antibodies may be produced by methods known in the art. These methods include the immunological method described by Kohler and Milstein in Nature 256:495–497 (1975) and by Campbell in "Monoclonal Antibody Technology, The Production and Characterization of Rodent and Human Hybridomas" in Burdon et al. (Eds.), Laboratory Techniques in Biochemistry and Molecular Biology, Volume 13, Elsevier Science Publishers, Amsterdam (1985); and Coligan, J. E, et al. (Eds.), Current Protocols in Immunology, Wiley Intersciences, New York, (1999); as well as the recombinant DNA method described by Huse et al., Science 246:1275–1281 (1989).

In order to produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein in Nature 256:495–497 (1975). See also Campbell, "Monoclonal Antibody Technology, The Production and Characterization of Rodent and Human Hybridomas" in Burdon et al. (Eds.), Laboratory Techniques in Biochemistry and Molecular Biology, Volume 13, Elsevier Science Publishers, Amsterdam (1985) and Coligan, J. E., et al. (Eds.), Current Protocols in Immunology,Wiley Intersciences, New York, (1999)). In order to be useful, a peptide fragment must contain sufficient amino acid residues to define the epitope of the molecule being detected.

If the fragment is too short to be immunogenic, it may be conjugated to a carrier molecule. Some suitable carrier molecules include keyhold limpet hemocyanin and bovine serum albumin. Conjugation may be carried out by methods known in the art (Coligan, J. E. et al. (Eds.) Current Protocols in Immunology, Chapter 9, Wiley Intersciences, New York, (1999)). One such method is to combine a cysteine residue of the fragment with a cysteine residue on the carrier molecule.

Methods for preparing polyclonal and monoclonal antibodies that exhibit specificity toward single amino acid differences between peptides are described by McCormick et al. in U.S. Pat. No. 4,798,787. These methods are incorporated herein by reference.

Predicting Individual's Response and Selecting Appropriate Drugs

In a preferred embodiment of the method of the present invention, the trait of interest is a response exhibited by an individual to some therapeutic treatment, for example, response to a drug targeting alpha-2BAR, alpha-2AAR or alpha-2CAR or response to a therapeutic treatment for a disease. As used herein the term "response" means any or all of the following: a quantitative measure of the response, no response, and adverse response (i.e., side effects).

In order to deduce a correlation between a response to a treatment and an alpha-2BAR, alpha-2AAR, or alpha-2CAR; alpha-2BAR, alpha-2AAR, or alpha-2CAR genotype or alpha-2BAR, alpha-2AAR, or alpha-2CAR haplotype, the clinician can obtain data on the clinical responses exhibited by a population of individuals who received the treatment, hereinafter the "clinical population". This clinical data may be obtained by analyzing the results of a clinical trial that has already been run and/or the clinical data may be obtained by designing and carrying out one or more new clinical trials. As used herein, the term "clinical trial" means any research study designed to collect clinical data on responses to a particular treatment, and includes but is not limited to phase I, phase II and phase III clinical trials. Standard methods are used to define the patient population and to enroll subjects.

It is preferred that the individuals included in the clinical population have been assessed for the clinical characteristics of the disease of interest. Such clinical characteristics may include symptoms, disease severity, response to therapy and the like. Characterization of potential patients could employ a standard physical exam or one or more lab tests.

The therapeutic treatment (i.e. drug) of interest is administered to each individual in the trial population and each individual's response to the treatment is measured using one or more predetermined criteria. It is contemplated that in many cases, the trial population will exhibit a range of responses and that the investigator will choose the number of responder groups (e.g., none, low, medium, high) made up by the various responses. In addition, the alpha-2BAR, alpha-2AAR, or alpha-2CAR gene for each individual in the trial population is genotyped at least one polymorphic site occurring in the alpha-2BAR, alpha-2AAR, alpha-2CAR, respectively, which may be done before or after administering the treatment. As used herein, treatment includes a stimulus (i.e., drug) administered internally or externally to an individual.

After both the clinical and polymorphism data have been obtained, correlations are created between individual response and the presence of the alpha-2BAR, alpha-2AAR or alpha-2CAR polymorphism; alpha-2BAR, alpha-2AAR, or alpha-2CAR genotype; or alpha-2BAR, alpha-2AAR, or alpha-2CAR haplotype. Correlations may be produced in several ways. In one embodiment, individuals are grouped by their alpha-2BAR, alpha-2AAR, or alpha-2CAR genotype; or alpha-2BAR, alpha-2AAR, or alpha-2CAR haplotype and then the averages and standard deviations of responses exhibited by the member of each group are calculated. These results are then analyzed to determine if any observed variation in clinical response between genotype or haplotype groups is statistically significant. Another method involves categorizing the response (e.g., none, low, medium, high or other such grades) and then assessing whether a particular genotype is more common in one group of responders compared to another. Statistical analysis methods which may be used are described in L. D. Fisher and G. vanBelle, "Biostatistics: A Methodology for the Health Sciences", Wiley-Interscience (New York) 1993.

It is also contemplated that the above methods for identifying associations between an alpha-2BAR, alpha-2AAR or alpha-2CAR polymorphism; alpha-2BAR, alpha-2AAR, or alpha-2CAR genotype; or alpha-2BAR, alpha-2AAR, or alpha-2CAR haplotype having the alpha-2BAR, alpha-2AAR or alpha-2CAR polymorphism, respectively, may be performed alone, or in combination with genotype(s) and haplotype(s) for one or more additional genomic regions.

In the most preferred embodiment, the polymorphisms and molecules of the present invention can be used to predict an individual's sensitivity or responsiveness to a pharmaceutical composition or drug, such as for example, an agonists or antagonists. Preferably, the individual's response to an agonist or antagonist, includes detecting a polymorphic site in the polynucleotide encoding the alpha-2B, the alpha-2A, or alpha-2C adrenergic receptor molecule comprising SEQ ID NOs: 1 or 2, SEQ ID NOs: 24 or 25, or SEQ ID NOs: 40 or 42, respectively, or fragment or complement thereof; and correlating the polymorphism to a predetermnined response for that particular polymorphism, haplotype or genotype, thereby predicting the individual's response to the agonist or antagonist. Accordingly, the present invention can be employed to guide the clinician in the selection of appropriate drug(s) or pharmaceutical composition(s). For example, individuals with a polymorphism comprising DEL301–303 of SEQ ID NO: 2 in the alpha-2BAR molecule are more sensitive to antagonists since endogenous agonist activation of the receptor by catecholamines is increased. Accordingly, with regards to agonists, the response or sensitivity can be predicted to be less for those individuals with the DEL301–303 polymorphism of the alpha-2BAR due to impaired coupling. Using this phenotype, the clinician can administer a higher dose of the agonist to the individual or a different drug altogether. Also, for example, individuals with a polymorphism comprising lysine at amino acid position 251 of (SEQ ID NO. 27) in the alpha-2AAR molecule are less sensitive to antagonists since endogenous agonist activation of the receptor by catecholamines is increased. Accordingly, with regards to agonists, the response or sensitivity can be predicted to be greater for those individuals with the polymorphism comprising lysine at amino acid position 251 of the alpha-2AAR due to impaired coupling. Finally, for example, individuals with a polymorphism comprising amino acid deletions GAGP (SEQ ID NO. 45) in the alpha-2CAR molecule are more sensitive to antagonists since agonist activation of the receptor by endogenous catecholamines is reduced. Accordingly, with regards to agonists, the response or sensitivity can be predicted to be less for those individuals with the polymorphism comprising amino acid deletions GAGP of the alpha-2CAR due to impaired coupling.

Alpha-2B, alpha-2A and alpha-2CAR adrenergic receptor molecule function or activity can be measured by methods known in the art. Some examples of such measurement include radio-ligand binding to the alpha-2B, alpha-2A or alpha-2C adrenergic receptor molecule by an agonist or antagonist, receptor-G protein binding, stimulation or inhibition of adenyly cyclase, MAP kinase, phosphorylation or inositol phosphate (IP3).

Figure 3A:
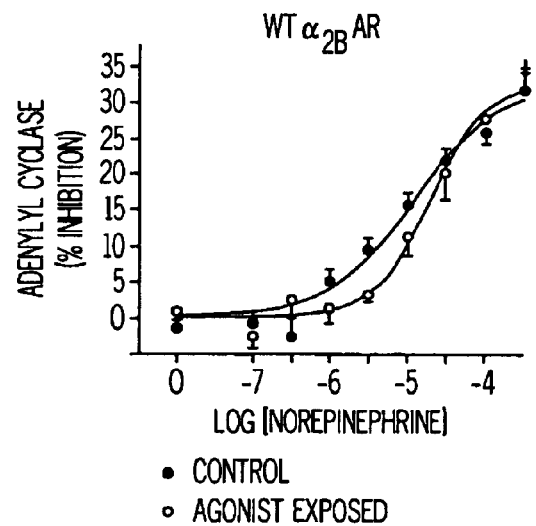
FIG. 3 graphically illustrates that the alpha-2BAR with deletion in amino acids 301 to 303 (Del301–303) of SEQ ID NO: 8, fails to undergo short-term agonist-promoted desensitization. Cells in culture expressing the two receptors were exposed to vehicle or 10 μM norepinephrine for 30 minutes at 37° C., washed extensively, membranes prepared and adenylyl cyclase activities determined as described in the examples. Panels A and B show results of full dose-response studies, which reveal that while the wild-type receptor (SEQ ID NO: 7) undergoes desensitization manifested as a rightward shift in the curve, the Del301–303 mutant does not. Panel C shows the percent inhibition of adenylyl cyclase at a submaximal concentration of norepinephrine in the assay (the $EC_{50}$ of the control membranes) for both wild-type and mutant conditions, indicating an ~54% desensitization of wild-type alpha-2BAR. The Del301–303 failed to display such desensitization. Results are from four independent experiments. See also Table 9. *=$p<0.05$ compared to control.
Figure 3B:
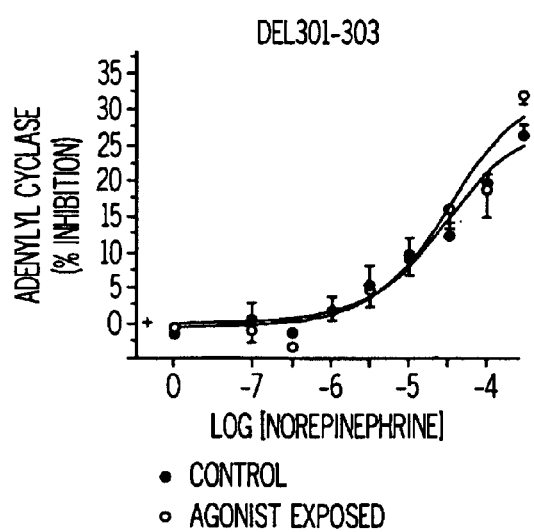
Figure 3C:
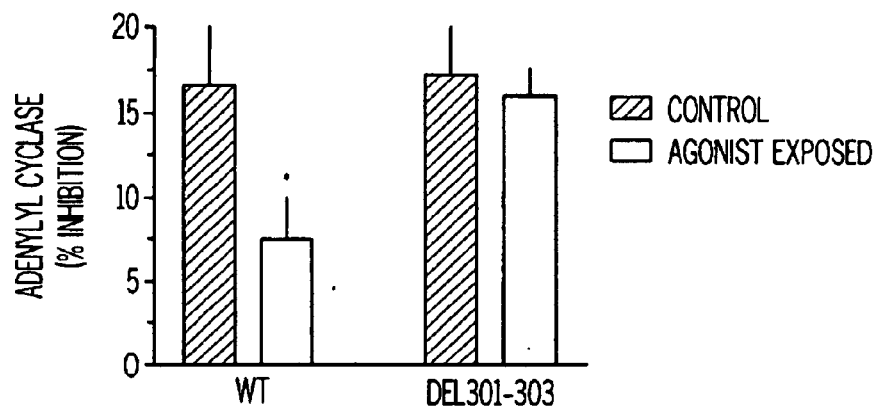
Figure 7A:
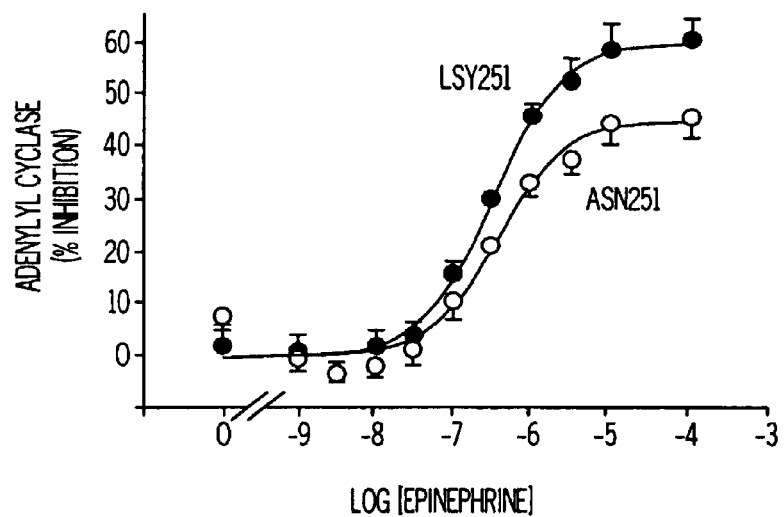
FIG. 7 is a graphic illustration of the coupling of the wild-type Asn251 and polymorphic Lys251 alpha-2AARs to the inhibition of adenylyl cyclase. Membranes from CHO cells were prepared and adenylyl cyclase activities determined as described below in the presence of 5.0 µM forskolin and the indicated concentrations of the full agonist epinephrine (Graph A) and the partial agonist oxymetazoline (Graph B). Results as shown are the percent inhibition of forskolin stimulated activities from clones at matched levels of expression (~2500 fmol/mg) from 5 individual experiments each (*indicates $p<0.05$ for the maximal inhibition compared to wild-type for both agonists).
Figure 7B:
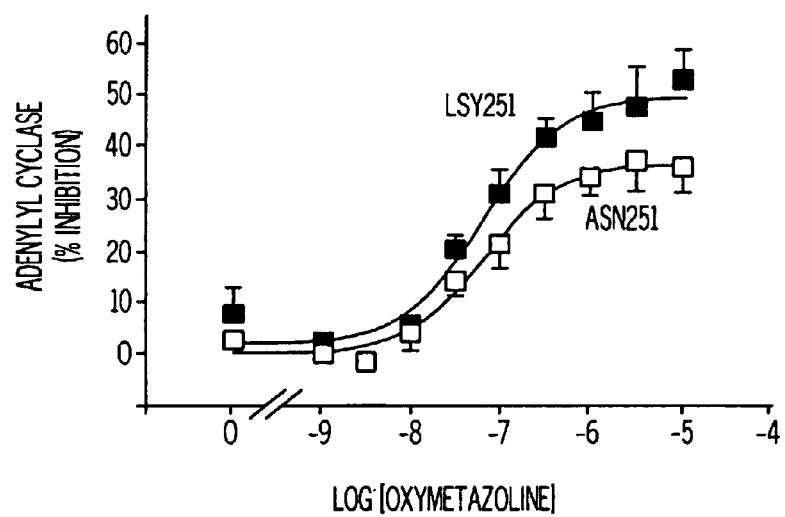

In one embodiment of the present invention, an alpha-2B adrenergic receptor agonist is administered, the agonist activates the alpha-2BAR molecule and $G_i$ coupling results in inhibiting adenylyl cyclase, and decreased phosphorylation. In this embodiment, the mutant alpha-2BAR shows decreased inhibition of adenylyl cyclase (FIG. 3A–C) as compared to the wild-type alpha-2BAR with insertion of three glutamic acids (IN301–303) at amino acid position 301 to 303 of SEQ ID NO: 7. Thus, mutant alpha-2BAR has decreased receptor activity or function.). In another embodiment of the present invention, an alpha-2A adrenergic receptor agonist is administered, the agonist activates the alpha-2AAR molecule and $G_i$ coupling results in inhibiting adenylyl cyclase, stimulation of MAP kinase, or stimulation of IP3. In this embodiment of the present invention, the polymorphic or mutant alpha-2AAR shows increased inhibition of adenylyl cyclase (FIG. 7A–B), increased stimulation of MAP kinase (FIG. 9B) and increased receptor-G protein binding (GTPγ5 binding, FIG. 8) as compared to the wild-type alpha-2AAR with asparagine at amino acid position 251 SEQ ID NO: 26. Thus, the polymorphic alpha-2AAR has enhanced receptor activity or function. In another embodiment of the present invention, the polymorphic alpha-2AAR shows increased MAP kinase as compared to the wild-type alpha-2AAR. Thus, mutant or polymorphic alpha-2AAR has enhanced receptor activity or function. In another embodiment of the present invention, an alpha-2C adrenergic receptor agonist is administered, the agonist activates the alpha-2CAR molecule and $G_i$ coupling results in inhibiting adenylyl cyclase, stimulation of MAP kinase, or stimulation of IP3. In this embodiment of the present invention, the wild-type alpha-2CAR shows increased inhibition of adenylyl cyclase stimulation of MAP kinase and stimulation of IP3 as compared to the variant alpha-2CAR with deletions in amino acids 322–325. Thus, wild-type alpha-2CAR has enhanced receptor activity or function. In another embodiment of the present invention, the wild-type alpha-2CAR shows increased inositol phosphate accumulation as compared to the variant alpha-2CAR with deletions in amino acids 322–325. Thus, wild-type alpha-2CAR has enhanced receptor activity or function. Preferably, receptor activity is measured by increased or decreased adenyly cyclase, MAP kinase, G protein receptor interaction, inositol phosphate and/or phosphorylation. Increased or decreased adenyly cyclase, MAP kinase, phosphorylation and/or inositol phosphate includes increases or decreases of preferably from about 10% to about 200%, more preferably, from about 20% to about 100%, and most preferably, from about 30% to about 60% from normal levels.

In another embodiment of the present invention, the mutant alpha-2BAR (DEL301–303) showed depressed phosphorylation resulting in loss of short-term agonist-promoted receptor desensitization. Thus, one phenotype of the alpha-2BAR Del301–303 polymorphism is decreased agonist-promoted phosphorylation that results in a complete loss of the ability for the receptor to undergo agonist-promoted desensitization. As used herein, desensitization includes a decline in response resulting from continuous application of agonist or to repeated application or doses. Clinically, desensitization is exhibited by tachyphylaxis. As used herein, tachyphylaxis includes rapidly decreasing response to a drug (i.e. agonist or antagonist) or pharmaceutical composition after administration of more than one dose.

For purposes of the present invention, an agonist is any molecule that activates a receptor. Preferably, the receptor is an alpha-2BAR, an alpha-2AAR, or an alpha-2CAR. Preferred agonists include alpha-2B, alpha-2A, or alpha-2C adrenergic receptor agonists, such as for example, epinephrine, norepinephrine, clonidine, oxymetazoline, guanabenz, UK14304, BHT933 and combinations thereof.

An antagonist is any molecule that blocks a receptor. Preferably, the receptor is an alpha-2BAR, an alpha-2AAR or an alpha-2CAR. Preferred antagonists include alpha-2B, alpha-2A or alpha-2C adrenergic receptor antagonists such as for example, yohimbine, prazosin, ARC 239, rauwolscine, idazoxan, tolazoline, phentolamine and combinations thereof.

As used herein a "predetermined response" includes a measurable or baseline effect of the agonist or antagonist correlated with the polymorphism. For example, individuals with the polymorphism wild-type insertion of amino acids 301–303 of the alpha-2B adrenergic receptor molecule display increased alpha agonist promoted coupling to $G_i$ and thus increased inhibition of adenylyl cyclase compared to the polymorphic or mutant alpha-2BAR. Also, the wild-type alpha-2BAR showed increased phosphorylation resulting in gain of short-term agonist-promoted receptor desensitization when compared to the mutant alpha-2BAR. Also, for example, individuals with the polymorphism wild-type Asn 251 of the alpha-2A adrenergic receptor molecule display depressed alpha agonist promoted coupling to $G_i$ and thus decreased inhibition of adenylyl cyclase compared to the polymorphic or mutant alpha-2AAR. Other baseline secondary messenger molecules can be used and correlated to the polymorphism, such as MAP kinase and inositol phosphate (See FIGS. 9 and 10). Finally, for example, individuals with the polymorphism deletions of amino acids 322–325 of the alpha-2C adrenergic receptor molecule display depressed alpha agonist promoted coupling to $G_i$ and thus decreased inhibition of adenylyl cyclase compared to the wild-type alpha-2CAR.

The present invention includes methods for selecting an appropriate drug or pharmaceutical composition to administer to an individual having a disease associated with alpha-2B, alpha-2C, or alpha-2A adrenergic receptor molecule. The method includes detecting a polymorphic site(s) in the polynucleotide encoding the alpha-2B, alpha-2A, or alpha-2C adrenergic receptor molecule comprising SEQ ID NOs: 1 or 2, SEQ ID NOs: 24 or 25, or SEQ ID NOs: 40 or 42, respectively, or fragment or complement thereof in the individual and selecting the appropriate drug based on the polymorphism or polymorphic site(s) present. The appropriate drug or pharmaceutical composition can be determined by those skilled in the art based on the particular polymorphism identified. For example, individuals with the DEL301–303 polymorphism showed depressed phosphorylation resulting in loss of short-term agonist-promoted receptor desensitization in the alpha-2BAR molecule. Thus, an agonist or antagonist prone to clinical tachyphylaxis can be used in patients with the DEL301–303 polymorphism. However, the response can be decreased due to the altered coupling of alpha-2BAR receptor such that if this were undesirable, another alpha-2BAR agonist can be selected, or another drug in a different class, can be employed. Accordingly, with regards to alpha agonists, the response or sensitivity can be predicted to be less for those individuals with the DEL301–303 polymorphism of the alpha-2BAR. This would lead the clinician to "customize" the choice of agonist based on this polymorphism. The skilled artisan will recognize that individuals with the DEL301–303 would be more sensitive to antagonists by virtue of their receptors being partially dysfunctional due to the polymorphism. Thus, the clinician can "customize" the choice of antagonist based on this polymorphism.

In another example, individuals with a polymorphism comprising lysine at amino acid position 251 of (SEQ ID NO. 27) in the alpha-2AAR molecule are less sensitive to antagonists since endogenous agonist activation of the receptor by endogenous catecholamines is increased. Accordingly, with regards to agonists, the response or sensitivity can be predicted to be greater for those individuals with the polymorphism comprising lysine at amino acid position 251 of the alpha-2AAR due to impaired coupling. This would lead the clinician to select an agonist or alternative drug(s) is indicated.

In a third example, individuals with a polymorphism comprising amino acid deletions GAGP (SEQ ID NO. 45) in the alpha-2CAR molecule are more sensitive to antagonists since agonist-receptor binding is reduced. Therefore, for example, identification of the polymorphism deletions of amino acids 322–325 of the alpha-2C adrenergic receptor molecule in the individual would lead the clinician to select alternative drug(s) or increase the dose of the agonist.

The present invention also contemplates adjusting or changing the dosing regimen of the drug or pharmaceutical composition based on the insertion or deletion present at amino acid positions 301 to 303. For example, individuals with DEL301–303 genotype do not undergo desensitization or tachylphylaxis with the administration of repeated doses over time. Thus, the clinician would not expect the pharmacologic effect of the drug to wane over time. An accelerated dosing regimen could be used in the individual with the DEL301–303 polymorphism without the need for slowly increasing the dose, as would be required in those with the wild-type receptor (IN301–303). Accordingly, individuals with the wild-type genotype (IN301–303) undergo desensitization or tachylphylaxis with the administration of repeated doses over time. Thus, the clinician would expect the pharmacologic effect of the drug to wane over time and the clinician would need to slowly increase the dose over time.

As used herein, "appropriate pharmaceutical composition" includes at least one drug that increases therapeutic efficacy of the drug based on a patient population with a particular disease. Each population will typically have a unique characteristic response to the drug. Knowledge of the efficacies of two or more drugs in treating individuals with different genetic variations provides the opportunity to select the drug effective in treating a large percentage of the total population of individuals while maintaining little or no toxicity.

For the purposes of the present invention, "correlating the polymorphism with a predetermine response" includes associating the predetermined response with the polymorphism that occurs at a higher allelic frequency or rate in individuals with the polymorphism than without. Correlation of the polymorphism with the response can be accomplished by bio-statistical methods known in the art, such as for example, Chi-squared tests or other methods described in L. D. Fisher and G. vanBelle, *Biostatistics: A Methodology for the Health Sciences*, Wiley-Interscience (New York) 1993.

For example, DEL301–303 polymorphism is more common in Caucasians than African-Americans, with allele frequencies of 0.31 and 0.12, respectively. The polymorphism results in depressed phosphorylation causing a loss of short-term agonist-promoted receptor desensitization in the alpha-2BAR molecule.

In another example, the lysine 251 polymorphism which results in a gain in alpha-2AAR function occur at a lower rate in Caucasians. In contrast, the allelic frequency, is ~10-fold higher in African-Americans. In a third example, polymorphisms resulting in a defective alpha-2CAR molecule occur at a lower rate in Caucasians with an allele frequency of 0.040. In contrast, the frequency is ~10-fold higher (0.381) in African-Americans (Table 5). Therefore, an appropriate drug can be selected based upon the individual's pharmaco-ethnogenetics.

For the purposes of the present specification, drugs and pharmaceutical compositions are used interchangeably. Drugs or pharmaceutical compositions contemplated by the present invention include therapeutic compounds such as an analgesic drug, an anesthetic agent, an anorectic agent, an anti-anemia agent, an anti-asthma agent, an anti-diabetic agent, an antihistamine, an anti-inflammatory drug, an antibiotic drug, an antimuscarinic drug, an anti-neoplastic drug, an antiviral drug, a cardiovascular drug, a central nervous system stimulant, a central nervous system depressant, an anti-depressant, an anti-epileptic, an anxyolitic agent, a hypnotic agent, a sedative, an anti-psychotic drug, a beta blocker, a hemostatic agent, a hormone, a vasodilator and a vasoconstrictor.

Preferred drugs include the alpha agonists and alpha antagonists. Most preferred drugs include the alpha-2B, alpha-2A, and alpha-2C agonists and alpha-2B, alpha-2A, alpha-2C antagonists. According to the invention, pharmaceutical compositions or drugs comprising one or more of the therapeutic compounds described above, and a pharmaceutically acceptable carrier or excipient, may be administered to an individual predisposed or having the disease as described, orally, rectally, parenterally, intrasystemically, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions used in the methods of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions used in the present methods may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drugs, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 µm in diameter. Suitable inert carriers include sugars such as lactose. Desirably, at least 95% by weight of the particles of the active ingredient have an effective particle size in the range of 0.01 to 10 µm.

Alternatively, the composition or drugs may be pressurized and contain a compressed gas, such as nitrogen or a liquefied gas propellant. The liquefied propellant medium and indeed the total composition is preferably such that the active ingredients do not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye. The active compounds are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the active compounds with suitable non-irritating excipients or carriers such as cocoa butter, polyethylene glycol or a suppository wax which are solid at room temperature but liquid at body temperature and therefore melt in the rectum or vaginal cavity and release the drugs.

The compositions used in the methods of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form, in addition to one or more of the active compounds described above, can contain stabilizers, preservatives, excipients and the like. The preferred lipids are the phospholipids and the phosphatidyl cholines (lecithins), both natural and synthetic.

Typical dosages and durations of treatment are as described in clinician's textbooks such as Physician's Desk Reference 2000, incorporated herein by reference, and will be familiar to physicians and other practitioners in the art.

The above methods of the present invention can be used in vivo, in vitro, and ex vivo, for example, in living mammals as well as in cultured tissue, organ or cellular systems. Mammals include, for example, humans, as well as pet animals such as dogs and cats, laboratory animals, such as rats and mice, hamsters and farm animals, such as horses and cows. Tissues, as used herein, are an aggregation of similarly specialized cells which together perform certain special functions. Cultured cellular systems include any cells that express the alpha-2BAR, alpha-2AAR or alpha-2CAR molecule, such as pre and post synaptic neurons in the brain or any cell transfected with the alpha-2B, alpha-2A, or alpha-2C gene.

Having now generally described the invention, the same may be more readily understood through the following reference to the following examples, which are provided by way of illustration and are not intended to limit the present invention unless specified.

EXAMPLES

Examples 1–6 relate to the alpha-2BAR. Examples 7–14 relate to the alpha-2AAR. Examples 15–21 relate to the alpha-2CAR.

Examples 1–6 below describe a polymorphic variant of the human alpha-2BAR which includes a deletion of three glutamic acids (residues 301–303) in the third intracellular loop. This polymorphism was found to be common in Caucasians (31%) and to a lesser extent in African-Americans (12%). The consequences of this deletion were assessed by expressing wild-type and the Del301–303 receptors in CHO and COS cells. Ligand binding was not affected while a small decrease in coupling to the inhibition of adenylyl cyclase was observed with the mutant. The deletion occurs within a stretch of residues which is thought to establish the milieu for agonist-promoted phosphorylation and desensitization of the receptor by G-protein coupled receptor kinases (GRKs). Agonist-promoted phosphorylation studies carried out in cells co-expressing the alpha-2BARs and GRK2 revealed that the Del301–303 receptor displayed -56% of wild-type phosphorylation. Furthermore, the depressed phosphorylation imposed by the deletion was found to result in a complete loss of short-term agonist-promoted receptor desensitization. Thus the major phenotype of the Del301–303 alpha-2BAR is one of impaired phosphorylation and desensitization by GRKs, and thus the polymorphisms renders the receptor incapable of modulation by a key mechanism of dynamic regulation.

Example 1

Polymorphism Detection

The nucleic acid sequence encoding the third intracellular loop of the human alpha-2BAR (GenBank assession #AF009500, SEQ ID No: 1) was examined for polymorphic variation by performing polymerase chain reactions (PCR) to amplify this portion of the cDNA from genomic DNA derived from blood samples. In this application the adenine of the initiator ATG codon of the open reading frame of the receptor is designated as nucleotide 1 and amino acid 1 is the encoded methionine. The human receptor consists of 450 amino acids. For initial examination, DNA from 39 normal individuals was utilized. Two overlapping fragments encompassing the third intracellular loop region were generated using the following primers pairs: fragment 1 (534 bp), 5'-GCTCATCATCCCTTTCTCGCT-3' (sense) SEQ ID NO: 13 and 5'-AAAGCCCCACCATGGTCGGGT-3' (antisense)

SEQ ID NO: 14 and fragment 2 (588 bp), 5'-CTGATCGCCAAACGAGCAAC-3' (sense) SEQ ID NO: 15 and 5'-AAAAACGCCAATGACCACAG-3' SEQ ID NO: 16 (antisense). The 5' end of each sense and antisense primer also contained sequences corresponding to the M13 forward (5'-TGTAAAACGACGGCCAGT-3') SEQ ID NO: 17 and M13 reverse (5'-CAGGAAACAGCTATGACC-3') SEQ ID NO: 18 universal sequencing primers, respectively. The PCR reactions consisted of ~100 ng genomic DNA, 5 pmol of each primer, 0.8 mM dNTPs, 10% DMSO, 2.5 units PLATINUM TAQ™ DNA polymerase (Gibco/BRL), 20 uL 5× buffer J (Invitrogen) in a 100 μl reaction volume. Reactions were started by an initial incubation at 94° C. for four minutes, followed by 35 cycles of 94° C. for 30 seconds, 58° C. (fragment 1) or 60° C. (fragment 2) for 30 seconds, and 72° C. for one minute, followed by a final extension at 72° C. for seven minutes. PCR reactions were purified using the QIAQUICK™ PCR purification system (Qiagen), and automated sequencing of both strands of each PCR product was performed using Applied Biosytmes 370 sequencer using dye primer methods. As discussed, a 9 bp in frame deletion at nucleotide positions 901 to 909 occurring in SEQ ID NO: 2 was detected which resulted in a loss of three glutamic acid residues at amino acid positions 301–303. Thus, this polymorphism was denoted Del301–303. Of note, previous reports have identified this polymorphism (21, 22). Heinonen et al. refer to the polymorphism as DEl 297–299 or DEL 298–300 (which may be a numbering error) while Baldwin et al. refer to it as a 9-base in-frame deletion corresponding loss of 3 glutamic acid residues. No other nonsynonymous or synonymous polymorphisms were identified. PCR amplification of 209 and 200 bp fragments encompassing this polymorphic region allowed screening of additional DNA samples whose genotypes were distinguished by size when run on 4% Nuseive agarose gels. PCR conditions were the same as described above except that buffer F was used with the following primers: 5-AGAAGGAGGGTGTTTGTGGGG-3' (sense) SEQ ID NO: 19 and 5'-ACCTATAGCACCCACGCCCCT-3' (antisense) SEQ ID NO: 20.

Example 2

Constructs and Cell Transfection

To create the polymorphic alpha-2BAR construct, a 1585 bp PCR product encompassing the alpha-2BAR gene was amplified from a homozygous deletion individual using the following primers: 5'-GGCCGACGCTCTTGTCTAGCC-3' (SEQ ID NO: 21) and 5'-CAAGGGGTTCCTAAGATGAG-3' (SEQ ID NO: 22). This fragment was digested and subcloned into the Xcm I and BamH I sites of the wild-type alpha-2BAR sequence in the expression vector pBC12BI (17). The integrity of the construct was verified by sequencing. Chinese hamster ovary cells (CHO-K1) were stably transfected by a calcium phosphate precipitation technique as previously described using 30 μg of each receptor construct and 0.5 μg of pSV$_2$neo to provide for G418 resistance (23). Selection of positive clones was carried out in 1.0 mg/ml G418 and expression of the alpha-2BAR from individual clonal lines was determined by radioligand binding as described below. Several clonal lines with matched expression levels between 500–1000 fmol/mg were utilized as indicated. Cells were grown in monolayers in Ham's F-12 medium supplemented with 10% fetal calf serum, 100 units/ml penicillin, 100 μg/ml streptomycin and 80 μg/ml G418 (to maintain selection pressure) at 37° C. in a 5% $CO_2$ atmosphere. For phosphorylation experiments, receptors were epitope tagged with the influenza hemagglutinin nonopeptide YPYDVPDYA (SEQ ID NO: 23) at the amino terminus. This was accomplished by constructing vectors using the above constructs with insertions of in-frame sequence encoding the peptide using PCRs essentially as previously described (24). Tagged receptors were expressed at ~15 pmol/mg, along with GRK2 (βARK1), in COS-7 cells using a DEAE Dextran technique as described (16).

Example 3

Adenylyl Cyclase Activities

Alpha-2BAR inhibition of adenylyl cyclase was determined in membrane preparations from CHO cells stably expressing the two receptors using methods similar to those previously described (25). Briefly, cell membranes (~20 μg) were incubated with 27 μM phosphoenolpyruvate, 0.6 μM GTP, 0.1 mM cAMP, 0.12 mM ATP, 50 μg/ml myokinase, 0.05 mM ascorbic acid and 2 μCi of [α-32P]ATP in a buffer containing 40 mM HEPES, pH 7.4, 1.6 mM MgCl2 and 0.8 mM EDTA for 30 minutes at 37° C. Activities were measured in the presence of water (basal), 5 μM forskolin, and 5 μM forskolin with the indicated concentrations of agonists. Reactions were terminated by the addition of a stop solution containing excess ATP and cAMP and ~100,000 dpm of [3H]cAMP. Labeled cAMP was isolated by gravity chromatography over alumina columns with [3H]cAMP used to quantitate column recovery. Results are expressed as percent inhibition of forskolin stimulated activity. For desensitization experiments, cells were pretreated for 30 min at 37° with media alone or with media containing 10 μM norepinephrine, placed on ice, and washed five times with cold PBS prior to membrane preparation. Desensitization of alpha-2BAR is manifested by a shift to the right in the dose-response curve for the inhibition of adenylyl cyclase (i.e., increase in EC50) without a significant change in the maximal response (17–19). To quantitate the magnitude of this desensitization, the inhibitory response under control conditions at a submaximal concentration of agonist (the EC50) in the assay was determined from the curve and compared to the response to this same concentration from membranes derived from cells exposed to norepinephrine. This method has been previously validated (26) in several G protein coupled receptor systems.

Example 4

Radioligand Binding

Expression of mutant and wild-type alpha-2BAR was determined using saturation binding assays as described (25, 27) with [$^3$H]yohimbine or [$^{125}$I]aminoclonidine with 10 μM phentolamine or 10 μM yohimbine, respectively, used to define nonspecific binding. For competition studies, membranes were incubated in 50 mM Tris-HCL, pH 7.4, 10 mM MgSO$_4$, 0.5 mM EDTA with 2.0 nM [$^3$H]yohimbine and 16 concentrations of the indicated competitor in the absence or presence of guanine nucleotide for 30 minutes at 25° C. Reactions for the above radioligand binding studies were terminated by dilution with 4 volumes of ice cold 10 mM Tris-HCL, pH 7.4 buffer and vacuum filtration over Whatmann GF/C glass fiber filters.

Example 5

Intact Cell Receptor Phosphorylation

Transiently transfected COS-7 cells expressing equivalent levels for each receptor were grown to confluence and incubated with [$^{32}$P] orthophosphate (~4 mCi/100 mm plate) for 2 h at 37° C. in 5% $CO_2$ atmosphere. Cells were then incubated in the presence or absence of 100 μM norepinephrine for 15 mm, washed 5 times with ice-cold PBS, solubilized in 1 ml of a buffer contaiting 1% Triton-X 100, 0.05%

SDS, 1 mM EDTA, and 1 mM EGTA in PBS, by rotation in a microcentrifuge tube for 1 h at 40C. This and all subsequent steps included the protease inhibitors benzamidine (10 µg/ml), soybean trypsin inhibitor (10 µg/ml), aprotinin (10 mg/ml), and leupeptin (5 µg/ml) and the phosphatase inhibitors sodium fluoride (10 mM) and sodium pyrophosphate (10 mM)>(A separate flask was scraped in 5 mM Tris/2 mM EDTA and membranes prepared for radioligand binding as described above.) Unsolubilized material was removed by centrifugation at 40000 g at 4° C. for 10 min. The HA epitope tagged alpha-2BARs were immunoprecipitated using an anti-HA high affinity monoclonal antibody (Roche) as previously described (24). Briefly, solubilized material was preincubated for 2 h at 4° C. with protein G Sepharose beads to remove nonspecific binding. The supernatant was then incubated with protein G Sepharose beads and a 1:200 dilution of antibody for 18 h at 4° C. Following immunoprecipitation, the beads were washed 3 times by centrifugation and resuspension, and then incubated at 37° C. for 1 hour in SDS sample buffer. Proteins in the supematant were then fractionated on a 10% SDS-polyacrylamide gel with equal amounts of receptor (based on radioligand binding) loaded in each lane. Signals were visualized and quantitated using a Molecular Dynamics PhosphorImager with IMAGEQUANT™ Software.

Example 6
Protein Determination, Adenylyl Cyclase and Radioligand Binding Assay and Genotype Protein determinations were by the copper bicinchoninic acid method (28). Data from adenylyl cyclase and redioligand binding assays were analyzed by iterative least-square techniques using PRIZM™ software (GraphPad, San Diego, Calif.). Agreement between genotypes observed and those predicted by the Hardy-Weinberg equilibrium was assessed by a Chi-squared test with on degree of freedom. Genotype comparisons were by Fisher's exact test. Comparisons of results from biochemical studies were by t-tests and significance was considered when $p<0.05$. Data are provided as means ± standard errors.

Results and Discussion of Examples 1–6

Sequence analysis of the third intracellular loop of the alpha-2BAR gene from 78 chromosomes revealed a single sequence variant. This consisted of an in-frame 9 bp deletion (GAAGAGGAG, SEQ ID NO: 3) beginning at nucleotide 901 of SEQ ID NO: 1 (FIG. 1a) that results in loss of three glutamic acid residues at amino acid positions 301–303 (SEQ ID NO:11) of the third intracellular loop of the receptor (FIG. 2). Using the rapid detection method (FIG. 1b), allele frequencies were determined in a larger population of apparently normal Caucasians and African-Americans. The frequencies of the wild-type and the Del301–303 (mutant) polymorphic alpha-2BAR are shown in Table 1.

The deletion polymorphism is more common in Caucasians than African-Americans, with allele frequencies of 0.31 and 0.12, respectively. The distribution of homozygous and heterozygous alleles in either population was not different than that predicted from the Hardy-Weinberg equilibrium ($p>0.8$).

The consequences of this polymorphism on ligand binding and receptor function were evaluated by stably expressing the human wild-type alpha-2BAR and the Del301–303 receptor in CHO cells (shown in Table 8)

Saturation radioligand binding studies revealed a small but statistically significant lower affinity for the alpha-2BAR antagonist [$^3$H]yohimbine for Del301–303 compared to the wild-type receptor ($K_d$=5.1±0.2 vs 3.8±0.3 nM, respectively, n=5, $p<0.05$). Agonist (epinephrine) competition binding experiments carried out in the presence of GppNHp revealed a small increase in the $K_i$ for the polymorphic receptor (285±8.7 vs 376±66 nM, n=5, $p<0.05$). In similar studies carried out in the absence of guanine nucleotide, two-site fits were obtained for both receptors with no differences in the $K_L$ or the percentage of receptors in the high affinity state (% $R_H$, Table 8). However, a trend towards an increased $K_H$ was observed with the Del301–303 mutant. These results prompted additional studies with the partial agonist radioligand [$^{125}$I]-aminoclonidine. Saturation binding studies (in the absence of GppNHp) with concentrations of the ligand from 0.2–4 nM revealed a single site with a $K_d$~1 nM as reported by others (27). Comparison of the wild-type alpha-2BAR and the Del301–303 receptor revealed essentially identical $K_d$s for [$^{125}$I]-aminoclonidine (1.33±0.12 vs 1.22±0.07 nM, respectively). Taken together, the data suggest that there is little, if any, effect of the deletion in the third intracellular loop on the conformation of the ligand binding pocket within the transmembrane spanning domains.

To address the functional consequences of the mutation, studies examining agonist-promoted inhibition of forskolin stimulated adenylyl cyclase activities were carried out in lines expressing the wild-type alpha-2BAR and the Del301–303 receptor at densities of 626±54 and 520±82 fmol/mg (n=7, $p>0.05$). The results of these studies are shown in Table 9.

As can be seen, the Del301–303 receptor displayed less inhibition of adenylyl cyclase (23.4±2.2%) compared to wild-type alph-2BAR (28.5±1.6%, $p<0.05$). Furthermore, the polymorphic receptor had a greater $EC_{50}$ (19.6±5.5 vs 7.9±2.1 nM, $p<0.01$). Thus, the loss of the three glutamic acids in the third intracellular loop, which is known to contain regions important for G-protein coupling, results in a modest decrease in agonist-mediated receptor function.

The deletion polymorphism occurs in a highly acidic stretch of amino acids (EDEAEEEEEEEEEEEE, SEQ ID NO: 9) within the third intracellular loop of alpha-2BAR (FIG. 2). The structural importance of this region has been previously assessed and shown to be critical for short-term agonist-promoted receptor phosphorylation leading to desensitization (18). These data and reports by others (29) suggest that this acidic environment is necessary for receptor phosphorylation by GRKs. Therefore, to investigate the consequences of this deletion polymorphism on receptor desensitization, agonist-promoted inhibition of adenylyl cyclase activity was determined in membranes from CHO cells expressing the wild-type and Del301–303 receptor after pretreatment with norepinephrine. In these experiments, cells were incubated with media alone or media containing agonist (10 µM norepinephrine) for 30 min and extensively washed, membranes prepared, and agonist-mediated inhibition of forskolin stimulated adenylyl cyclase activity was determined. As described previously (17) and shown in FIG. 3 and Table 9, desensitization of wild-type alpha-2BAR expressed in CHO cells is manifested by an increase in the $EC_{50}$ for agonist-mediated inhibition of adenylyl cyclase. Analysis of composite curves derived from four independent experiments shows an increase from 7.4 µM to 29.4 µM for the wild-type alpha-2BAR. In contrast, there was no change in the $EC_{50}$ for the deletion receptor following agonist pretreatment (29.5 µM versus 31.2 µM). Desensitization was quantitated by examining adenylyl cyclase activities at a submaximal concentration of agonist (the EC$_{50}$ for the control condition). At this concentration, wild-type alpha-2BAR inhibited adenylyl cyclase activity by 16.5±3.9%; with agonist preexposure, inhibition at this same concentration of agonist was 7.6±2.3%, (n=4, p<0.05, FIG. 3c), amounting to ~54% desensitization of receptor function. Submaximal inhibition of adenylyl cyclase for the Del301–303 receptor, however, was not different between control and agonist-treated cells (17.1±3.0% vs 15.9±1.7%, n=4, p=ns). In another two cell lines with matched expression of ~600 fmol/mg, the same desensitization phenotypes for wild-type and the Del301–303 polymorphic receptor were observed (data not shown).

Figure 4:
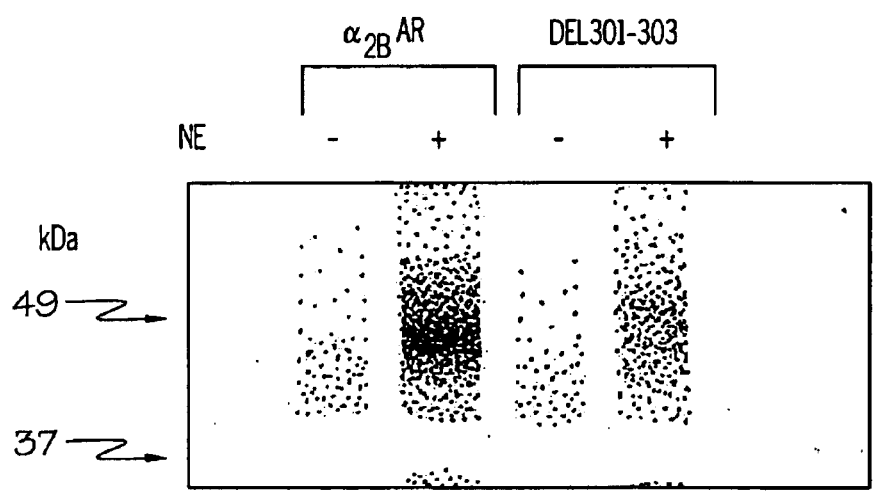
FIG. 4 illustrates that alpha-2BAR with deletion in amino acids 301 to 303 (Del301–303) has impaired agonist-promoted phosphorylation. Cells co-expressing each receptor and GRK2 were incubated with $^{32}$P-orthophosphate, exposed to 10 µM norepinephrine for 15 minutes, and receptor purified by immunoprecipitation as described in the examples. Shown is an autoradiogram from a single experiment representative of four performed.

We next performed whole cell phosphorylation studies of the wild-type and polymorphic alpha-2BAR under the same conditions as those used for desensitization. We hypothesized that agonist-promoted phosphorylation would be decreased in the polymorphic receptor. However, given that this receptor displays rightward-shifted dose response curves for inhibition of adenylyl cyclase at baseline, we also considered the possibility that the receptor is significantly phosphorylated in the basal state. Studies were carried out in cells co-transfected with the receptor and GRK2 (βARK1), a strategy that we have previously shown to be useful in identifying receptor-GRK interactions (30). The results of a representative study are shown in FIG. 4a and mean results from four experiments in FIG. 4b. The wild-type alpha-2BAR underwent a 5.84±0.49 fold increase in phosphorylation with agonist exposure. In contrast, while the Del301–303 receptor displayed some degree of agonist-promoted phosphorylation, the extent was clearly less (3.28±0.24 fold, p<0.05 compared to wild-type). Basal phosphorylation was equivalent between the two receptors.

It is interesting to note that this partial loss of phosphorylation results in a receptor that fails to undergo any degree of functional desensitization. While it might seem reasonable to assume that such phosphorylation would be associated with some degree of desensitization, several previous studies with the $\alpha_{2A}$- and alpha-2BAR subtypes indicate that full (i.e., wild-type) phosphorylation is necessary for the desensitization process (16, 18, 24). For the $\alpha_{2A}$AR, we have shown that four serines in the third intracellular loop are phosphorylated after agonist exposure (16). Removal of serines by alanine substitution mutagenesis results in a proportional decrease in phosphorylation. Such partial phosphorylation (compared to wild-type), however, was found to be insufficient to cause any detectable desensitization. In a previous study of the alpha-2BAR, we deleted the entire aforementioned acidic region (18). Agonist-promoted phosphorylation was reduced by ~50% in this mutant, and desensitization was ablated. These results are entirely consistent with the current work, where a restricted substitution resulted in a decrease in phosphorylation and a complete loss of desensitization. Finally, we have also recently shown that a chimeric alpha-2A/alpha-2CAR which undergoes agonist-promoted phosphorylation, fails to exhibit desensitization (24). Taken together with our current work, these results indicate that the conformation of the third loop evoked by GRK mediated phosphorylation which provides for the binding of arrestins (which is the ultimate step that imparts uncoupling) is highly specific. Thus a precise phosphorylation-dependent conformation is apparently required for arrestin binding to alpha-2AR and subsequent functional desensitization. Perturbations of the milieu can thus have significant functional consequences, as occurs with the Del301–303 polymorphic alpha-2BAR.

Thus the major signaling phenotypes of the alpha-2BAR Del301–303 polymorphism is one of decreased agonist-promoted phosphorylation which results in a complete loss of the ability for the receptor to undergo agonist-promoted desensitization and a decrease in receptor coupling. The potential physiologic consequences of the polymorphism could be related to either or both of the above phenotypes. A receptor that fails to undergo desensitization would be manifested as static signaling despite continued activation of the receptor by endogenous or exogenous agonist. Such a lack of regulation by agonist may perturb the dynamic relationship between incoming signals and receptor responsiveness that maintains homeostasis under normal or pathologic conditions. Recently, Gavras and colleagues (14) have shown that alpha-2B–/+ mice fail to display a hypertensive response to salt loading after subtotal nephrectomy. Thus a polymorphic alpha-2BAR that fails to desensitize (i.e., does not display regulatable function) may predispose to salt-sensitive hypertension. Regarding the therapeutic response to alpha-2AR agonists, the phenotype of the Del301–303 receptor indicates that individuals with this polymorphism would display little tachyphylaxis to continued administration of agonists. In addition, the initial response to agonist would also be reduced based on the somewhat depressed coupling of the Del301–303 receptor.

Until recently, it has been difficult to differentiate alpha-2BAR function from the other two subtypes in physiologic studies. With the development of knock-out mice lacking each $\alpha_2$AR subtype (5, 6, 13, 31), certain functions can now be definitively attributed to specific subtypes. Characterization of the alpha-2BAR knock-out mouse has indicated that the alpha-2BAR subtype is expressed on vascular smooth muscle and is responsible for the hypertensive response to $\alpha_2$AR agonists (13). This indicates that vascular alpha-2BAR contribute to overall vascular tone and thus participate in systemic blood pressure regulation. This role may be more important, though, during adaptive conditions, such as salt loading, since resting blood pressure is normal in the heterozygous alpha-2B –/+ mice (14). Whether the alpha-2B –/– mice have altered resting blood pressures has not been studied in detail due to high perinatal lethality of the homozygous knockout (13). However, neither the region of chromosome 2 near the alpha-2BAR coding sequence, nor the deletion polymorphism, have been linked or associated with hypertension (21, 22, 32). No studies, though, have assessed whether the polymorphism is associated with salt-sensitive hypertension or other phenotypes, or the response to alpha-2BAR agonist.

In summary, we have delineated the signalling phenotype of a polymorphism of the alpha-2BAR that results in a deletion of three glutamic acids in the third intracellular loop of the receptor. The polymorphism is prevalent in the human population, with a frequency that is ~2 fold greater in Caucasians as compared to African-Americans. The polymorphic receptor displays wild-type agonist binding affinity but a small decrease in function in the resting state. The major phenotype, though, is a significant decrease in agonist-promoted phosphorylation by GRKs, which results in a receptor that fails to display agonist-promoted desensitization. To our knowledge this is the first polymorphism of any G-protein coupled receptor to affect GRK-mediated phosphorylation.

Examples 7–14 below describe a single nucleotide polymorphism occuring in nucleic acids encoding the alpha-2AAR molecule. This polymorphism results in an Asn to Lys substitution at amino acid 251 of the third intracellular loop of the alpha-2AAR molecule. The frequency of Lys251 was 10-fold greater in African-Americans compared to Caucasians, but was not associated with essential hypertension. To determine the consequences of this substitution, wild-type and Lys251 receptors were expressed in CHO and COS-7 cells. Expression, ligand binding, and basal receptor function were unaffected by the substitution. However, agonist-promoted [$^{35}$S]GTPγS binding was ~40% greater with the Lys251 receptor. In studies of agonist-promoted functional coupling to $G_i$, the polymorphic receptor displayed enhanced inhibition of adenylyl cyclase (60±4.4 vs 46±4.1% inhibition) and markedly enhanced stimulation of MAP kinase (57±9 vs 15±2 fold increase over basal) compared to wild-type alpha-2AAR. This enhanced agonist function was observed with catecholamines, azepines and imadazolines. In contrast, agonist stimulation of phospholipase C was not different between the two receptors. Unlike previously described variants of G protein coupled receptors where the minor species causes either a loss of function or increased non-agonist function, Lys251 alpha-2AAR can represent another class of polymorphism whose phenotype is a gain of agonist-promoted function.

Example 7
Polymorphism Detection

The intronless wild-type human alpha-2AAR gene identified as SEQ ID NO: 24 (GenBank Accession #AF281308 which includes the sequenic corrections illuminated by Guyer et al, 1990) was amplified by overlapping PCR reactions from genomic DNA derived from blood samples. The 1350 bp coding sequence as well as 341 bp 5'UTR and 174 bp 3'UTR were examined. For convenience, the adenine of the initiator ATG codon is designated as nucleotide 1 and amino acid 1 is the encoded methionine. The human receptor consists of 450 amino acids. For initial examination, DNA from 27 hypertensive individuals was utilized. Overlapping PCR products encompassing the $\alpha_{2A}$ gene were designated fragments 1–5 and were generated using the following primers: Fragment 1 (600 bp), 5'-TTTACCCATCGGCTCTCCCTAC-3' (sense) SEQ ID NO: 28 and 5'-GAGACACCAGGAAGAGGTTTTGG-3' (antisense) SEQ ID NO: 29; Fragment 2 (467 bp) 5'-TCGTCATCATCGCCGTGTTC-3' (sense) SEQ ID NO: 30 and 5'-CGTACCACTTCTGGTCGTTGATC-3' (antisense) SEQ ID NO: 31; Fragment 3 (556 bp), 5'-GCCATCATCATCACCGTGTGGGTC-3' (sense) SEQ ID NO: 32 and 5'-GGCTCGCTCGGGGCCTTGCCTTTG-3' (antisense) SEQ ID NO: 33; Fragment 4 (436 bp), 5'-GACCTGGAGGAGAGCTCGTCTT-3' (sense) SEQ ID NO: 34 and 5'-TGACCGGGTTCAACGAGCTGTTG-3' (antisense) SEQ ID NO: 35; and Fragment 5 (353 bp), 5'-GCCACGCACGCTCTTCAAATTCT-3' (sense) SEQ ID NO: 36 and 5'-TTCCCTTGTAGGAGCAGCAGAC-3' (antisense) SEQ ID NO: 37. The 5' end of each sense and antisense primer also contained sequence corresponding to the M13 Forward (5'-TGTAAAACGACGGCCAGT) SEQ ID NO: 38 and M13 Reverse (5'-CAGGAAACAGCTATGACC) SEQ ID NO: 39 universal sequencing primers, respectively. The PCR consisted of ~100 ng genomic DNA, 5 pmol of each M13 primer, 0.8 mM dNTPs, 10% DMSO, 2.5 units Platinum taq DNA polymerase (Gibco/BRL), 20 uL 5× buffer A (Invitrogen) in a 100 μl reaction volume. Reactions were started by an initial incubation at 94° C. for four minutes, followed by 35 cycles of 94° C. for 30 seconds, denaturation for 30 seconds, and 72° C. for one minute, followed by a final extension at 72° C. for seven minutes. The denaturation temperature was 56° C. for fragments 1 and 5, 58° C. for fragments 2 and 4, and 60° C. for fragment 3. PCR reactions were purified using QIAquick PCR purification system (Qiagen), and automated sequencing of both strands of each PCR product was performed using an Applied Biosystems sequencer using dye primer methods. As discussed, a C to G transversion at nucleotide 753 was identified that resulted in an asparagine to lysine change at amino acid 251 (shown in FIG. 5). This nucleotide change results in gain of a unique Sty I restriction endonuclease site in PCR fragment 3, and the presence or absence of this polymorphism in additional samples was studied by Sty I digestion of fragment 3 PCR products (shown in FIG. 5, Panel D). This rapid detection technique was applied to additional DNA samples providing genotypes at this locus from a total of 376 individuals (normotensive: 125 Caucasian and 99 African-American; hypertensive: 75 and 77 respectively). Normotensive and hypertensive patients were selected as described previously by(14).

Example 8
Constructs and Cell Transfection

To create the polymorphic alpha-2AAR Lys251 construct, a portion of the coding region of alpha-2AAR gene containing a G at nucleotide position 753 was amplified from a homozygous individual using fragment 2 sense and fragment 4 antisense primers (see PCR conditions described in Example 7). This fragment was digested with and subcloned into the Bgl II and Sac II sites of the wild type $\alpha_{2A}$AR sequence in the expression vector pBC12B1. Chinese hamster ovary cells (CHO-K1) were permanently transfected by a calcium phosphate precipitation technique as previously described using 30 μg of each receptor construct and 3.0 μg of pSV$_2$neo to provide for G418 resistance by the methods of (15). Selection of positive clones was carried out in 1.0 mg/ml G418 and expression of the alpha-2AAR from individual clonal lines was determined by radioligand binding as described below. Cells were grown in monolayers in Ham's F-12 medium supplemented with 10% fetal calf serum, 100 units/ml penicillin, 100 μg/ml streptomycin and 80 μg/ml G418 (to maintain selection pressure) at 37° C. in a 5% CO$_2$ atmosphere. COS-7 cells were co-transfected with 1–10 μg of each alpha-2AAR construct and ~5 μg $G_{i\alpha}$ using a DEAE-dextran method essentially as described previously by (16). These transfections also included 5 μg of the large T antigen containing plasmid, pRSVT (17), to maximize expression of the $\alpha_{2A}$AR gene from the SV40 promoter of pBC12B1.

Example 9
Adenylyl Cyclase Activities

Alpha-2AAR inhibition of adenylyl cyclase was determined in membrane preparations from CHO cells stably expressing the two receptors using methods similar to those previously described (18). Reactions consisted of 20 μg cell membranes, 2.7 mM phosphoenolpyruvate, 50 μM GTP, 0.1 mM cAMP, 0.12 mM ATP, 50 μg/ml myokinase, 0.05 mM ascorbic acid and 2 μCi of [α-$^{32}$P]ATP in a buffer containing 40 mM HEPES, pH 7.4, 1.6 mM MgCl$_2$ and 0.8 mM EDTA for 30 minutes at 37° C. Reactions were terminated by the addition of a stop solution containing excess ATP and cAMP and ~100,000 dpm of [$^3$H]cAMP. Labeled cAMP was isolated by gravity chromatography over alumina columns with [$^3$H]cAMP used to quantitate column recovery. Activities were measured in the presence of water (basal), 5 μM forskolin, and 5 μM forskolin with the indicated concentrations of agonists. Results are expressed as percent inhibition of forskolin stimulated activity.

Example 10
[$^{35}$S]GTPγS Binding

Receptor-G protein interaction was quantitated by [$^{35}$S] radiolabeled guanosine-5'-O-(3-thiotriphosphate) ([$^{35}$S]

GTPγS) binding in COS-7 cells transiently transfected with each alpha-2AAR construct and $G_{i\alpha2}$. Briefly, cell membranes (~20 µg) were incubated in buffer containing 25 mM Tris-HCl, pH 7.4, 5 mM $MgCl_2$, 1 mM EDTA, 1 mM dithiotheritol, 100 mM NaCl, 1 µM GDP, and 2 nM [$^{35}$S] GTPγS in a 100 µl reaction volume for 15 min at room temperature. Incubations were terminated by dilution with 4 volumes of ice cold 10 mM Tris-HCL, pH 7.4 buffer and vacuum filtration over Whatmann GF/C glass fiber filters. Nonspecific binding was measured in the presence of 10 µM GTPγS.

Example 11
MAP Kinase Activation

Activation of p44/42 MAP kinase was determined by quantitative immunoblotting using specific antibodies to identify phosphorylated and total MAP kinase expression. Briefly, confluent cells were incubated overnight in serum-free media prior to treatment with media alone (basal), epinephrine (10 µM), or thrombin (1 unit/ml) for 5 min. Cells were washed three times with phosphate-buffered saline (PBS) then lysed in RIPA buffer (20 mM Tris, pH 7.5, 150 mM NaCl, 1 mM EDTA, 1% NP-40, 0.5% deoxycholate, 0.1% SDS, and 5 mM NaF) containing protease inhibitors (10 µg/ml benzamidine, 10 µg/ml soybean trypsin inhibitor, 10 µg/ml aprotinin, and 5 µg/ml leupeptin). Western blots of these whole cell lysates were performed essentially as previously described (19). Membranes were incubated with phospho-p44/42 MAP kinase E10 antibody (New England Biolabs, Beverly, Mass.) at a dilution of 1:2000 for 1 hr at room temperature. Washed membranes were subsequently incubated with anti-mouse fluorescein-linked immunoglobulin followed by incubation with fluorescein alkaline phosphatase (ECF, Amersham). Fluorescent signals were quantitated by real-time acquisition using a Molecular Dynamics STORM imager. After stripping, membranes were incubated under the same conditions as described in Example 4 with a p44/42 MAP kinase monoclonal antibody to quantitate total MAP kinase expression.

Example 12
Inositol Phosphate Accumulation

Total inositol phosphate levels in intact cells were determined essentially as described previously (20). Briefly, confluent CHO cells stably expressing each of the alpha-2ARRs were incubated with [$^3$H]myoinositol (5 µCi/ml) in media lacking fetal calf serum for 16 hrs at 37° C. in 5% $CO_2$ atmosphere. Subsequently, cells were washed and incubated with PBS for 30 min followed by a 30 min incubation with 20 mM LiCl in PBS. Cells were then treated with PBS alone (basal), varying concentrations of epinephrine, or 5 units/ml thrombin for 5 min, and inositol phosphates were extracted as described by Martin (21). Following separation on Agl-X8 columns, total inositol phosphates were eluted with a solution containing 0.1 M formic acid and 1 M formate.

Example 13
Radioligand Binding

Expression of mutant and wild-type alpha-2AAR was determined using saturation binding assays as described (22) with 12 concentrations (0.5–30 nM) of [$^3$H]yohimbine and 10 µM phentolamine used to define nonspecific binding. For competition studies, membranes were incubated in 50 mM Tris-HCL, pH 7.4, 10 mM $MgSO_4$, 0.5 mM EDTA with 2.0 nM [$^3$H]yohimbine and 16 concentrations of the indicated competitor in the presence of 100 µM GppNHp for 30 minutes at 37° C. Reactions for the above radioligand binding studies were terminated by dilution with 4 volumes of ice cold 10 mM Tris-HCL, pH 7.4 buffer and vacuum filtration over Whatmann GF/C glass fiber filters.

Example 14
Protein Determination and Data Correlation

Protein determinations were by the copper bicinchoninic acid method (23). Data from adenylyl cyclase and radioligand binding assays were analyzed by iterative least-square techniques using Prizm software (GraphPad, San Diego, Calif.). Agreement between genotypes observed and those predicted by the Hardy-Weinberg equilibrium was assessed by a Chi-squared test with one degree of freedom. Genotype comparisons were by Fisher's exact test. Comparisons of results from biochemical studies were paired by t-tests and significance was considered when p<0.05. Data are provided as means±standard errors.

Results and Discussion of Examples 7–14

Sequence analysis of the entire coding region of the alpha-2AAR gene from 54 chromosomes revealed one non-synonymous sequence variant located within the third intracellular loop of the receptor (FIG. 5). This consisted of a C to G transversion at nucleotide 753 that changed amino acid 251 from Asn to Lys (FIG. 6). While the Lys251 receptor is relatively rare, it is ~10 fold more common in African-Americans than in Caucasians, with an allele frequency of 0.05 as compared to 0.004 (p=0.01). The distribution of homozygous and heterozygous alleles was not different than that predicted from Hardy-Weinberg equilibrium (p>0.9). Two previously unreported synonymous single nucleotide polymorphisms were also identified at nucleic acids 849 (C to G) and 1093 (C to A). Considering the role of the alpha-2AAR in regulating blood pressure, we also determined the frequency of this polymorphism in patients with essential hypertension. Our analysis of 99 normotensive and 77 hypertensive African-Americans as well as 125 normotensive and 75 hypertensive Caucasians showed no differences in the frequency of this polymorphism in patients with essential hypertension in either group.

The consequences of this polymorphism on ligand binding and receptor function were evaluated by permanently expressing the human wild-type alpha-2AAR and the Lys251 polymorphic receptor in CHO cells. Saturation radioligand binding studies revealed essentially identical dissociation binding constants for the alpha-2AAR antagonist [$^3$H]yohimbine ($K_d$=3.4±0.21 vs 3.6±0.25 nM respectively, n=4), and competition binding assays showed no differences in binding of the agonist (−) epinephrine ($K_i$=593±65 vs 734±31 nM respectively, n=3, Table 4). These data show that the ligand binding pocket composed of the transmembrane spanning domains is not perturbed by the presence of Lys at amino acid 251 in the third intracellular loop. The Lys251 polymorphism occurs in a highly conserved portion of the third intracellular loop of the $\alpha_{2A}AR$ (FIG. 6), in a region thought to be important for G-protein interaction (24). Indeed, as shown in FIG. 6, Asn is present in the position analogous to human 251 in all mammalian alpha-2AARs reported to date.

To assess whether this polymorphism affects G-protein coupling, functional studies examining agonist-promoted inhibition of forskolin-stimulated adenylyl cyclase activities were carried out in cell lines expressing the wild type Asn251 receptor and the polymorphic Lys251 receptor at levels of 2360±263 and 2590±140 fmol/mg (n=5, p>0.05), respectively.

TABLE 4

Pharmacological Properties of the Asn251 and Lys251 $\alpha_{2A}$ARs expressed in CHO cells.

| Receptor | Radioligand Binding | | | Adenylyl cyclase activity (pmol/min/mg) | |
|---|---|---|---|---|---|
| | $\beta_{max}$ (fmol/mg) | $^3$H-Yohimbine $K_D$ (nM) | Epinephrine $K_1$ (nM) | Basal | Forskolin |
| Asn251 | 2360 ± 263 | 3.4 ± 0.21 | 593 ± 65 | 11.9 ± 2.3 | 32.7 ± 4.0 |
| Lys251 | 2590 ± 140 | 3.6 ± 0.25 | 734 ± 31 | 13.9 ± 1.6 | 31.6 ± 6.5 |

As shown in Table 4, basal and 5.0 μM forskolin-stimulated adenylyl cyclase activities were not different between Asn251 and Lys251 expressing cell lines, indicating that non-agonist dependent function is equivalent with the two receptors. However, activation of the polymorphic Lys251 receptor with the full agonist epinephrine resulted in enhanced inhibition of adenylyl cyclase activity compared to wild-type alpha-2AARs. Maximal inhibition of adenylyl cyclase was 60±4.4% with the variant receptor compared to 46±4.1% with wild-type (n=5, p<0.005, FIG. 7a). Similar results were also found when receptors were activated by the partial agonist oxymetazoline, with the Lys251 having an ~40% augmented function compared to the Asn251 receptor (50±6.6% vs 35±4.7% inhibition, n=5, p<0.05, FIG. 7b). No significant differences in the $EC_{50}$ values for epinephrine (583±196 nM vs 462±145 nM) or for oxymetazoline (54.0±7.3 nM vs 67.3±15.7 nM) were observed.

Figure 8:
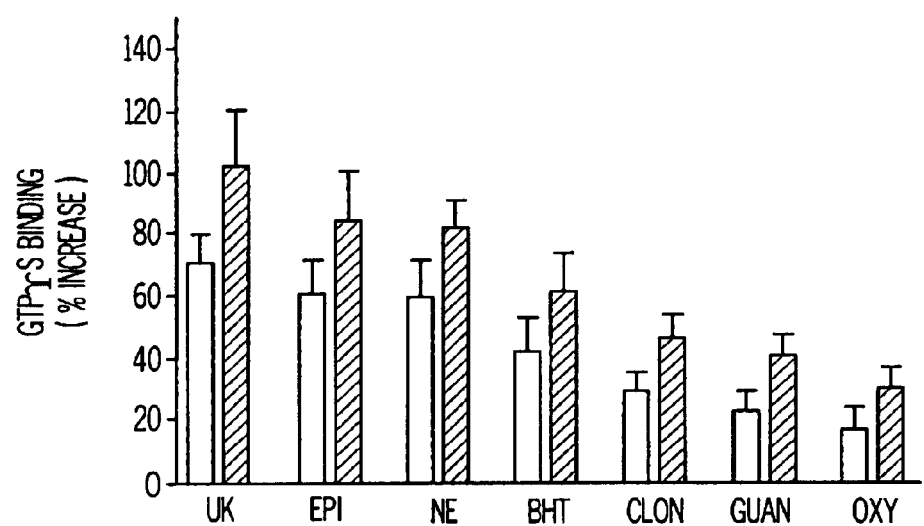
FIG. 8 is a bar graph illustration of wild-type Asn251 and polymorphic Lys251 alpha-2AAR promoted [$^{35}$S]GTPγS binding in response to full and partial agonists. Binding of [$^{35}$S]GTPγS was measured in membranes from COS-7 cells transiently coexpressing the wild-type and Lys251 alpha-2AAR and $G_{i\alpha2}$ as described below. Assays were carried out using 10 µM of the agonists UK 14304, epinephrine, norepinephrine, BHT-933, clonidine, guanabenz, and oxymetazoline. Results are shown as % increase over basal levels from three or more experiments.

This enhanced function was also found by quantitating agonist-promoted receptor-$G_i$ interaction with [$^{35}$S]GTPγS binding. In these experiments, Asn251 and Lys251 receptors were transiently coexpressed in COS-7 cells (2.3±0.3 vs 2.2±1.4 pmol/mg) along with $G_{i\alpha 2}$, and binding of [$^{35}$S]GTPγS was measured in membranes exposed to vehicle (basal) or saturating concentrations of various agonists. Here, full and partial agonists with diverse structures were utilized. As is shown in FIG. 8, the Lys251 receptor had increased [$^{35}$S]GTPγS binding in response to all agonists tested, albeit to varying degrees. Basal [$^{35}$S]GTPγS binding was equivalent. Stimulation with the full agonists UK 14304, epinephrine, and norepinephrine resulted in ~40% enhanced GTPγS binding for the Lys251 receptor as compared to the Asn251 receptor. On the other hand, partial agonists displayed from 45% (BHT-933) up to 72% (guanabenz) enhancement of [$^{35}$S]GTPγS binding with the Lys251 receptor. These results are consistent with the adenylyl cyclase activity studies which also showed enhanced function of the polymorphic receptor. In addition, they indicate that the gain-of-function phenotype is more pronounced with some, but not all, partial agonists compared to full agonists.

We next investigated agonist-mediated modulation of MAP kinase by wild-type and the Lys251 receptor. Alpha-2AAR act to stimulate MAP kinase activity and thus can potentially regulate cell growth and differentiation (2). While noting that regulation of MAP kinase activity is both receptor and cell-type specific, MAP kinase activation by alpha-2A receptors appears to be initiated by βγ released from $G_i$ (2).

Figure 9A:
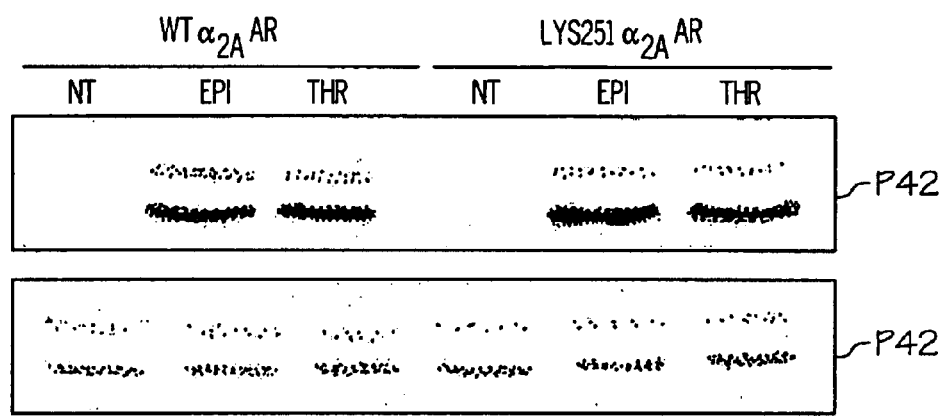
FIG. 9 illustrates stimulation of MAP kinase by wild-type and Lys251 alpha-2AARs. Phosphorylation of MAP kinase was determined in CHO cells by quantitative immunoblotting with enhanced chemifluorescence using antibodies specific for phosphorylated Erk 1/2. The same blots were stripped and reprobed for total MAP kinase expression, which was not significantly different between the two cell lines (Panel A). Cells were studied after incubation with carrier (basal), 10 µM epinephrine, or 1 unit/ml thrombin. Results are shown as the fold-stimulation over basal levels (Panel B). The * indicates $p<0.05$ compared to the wild-type response (n=3 experiments).
Figure 9B:
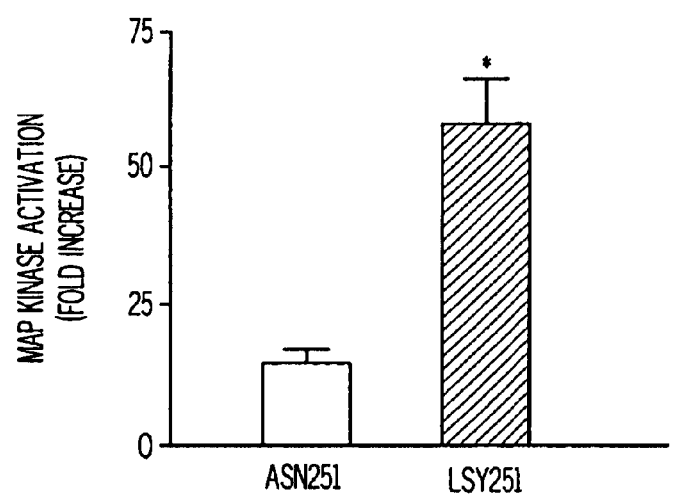
Figure 10:
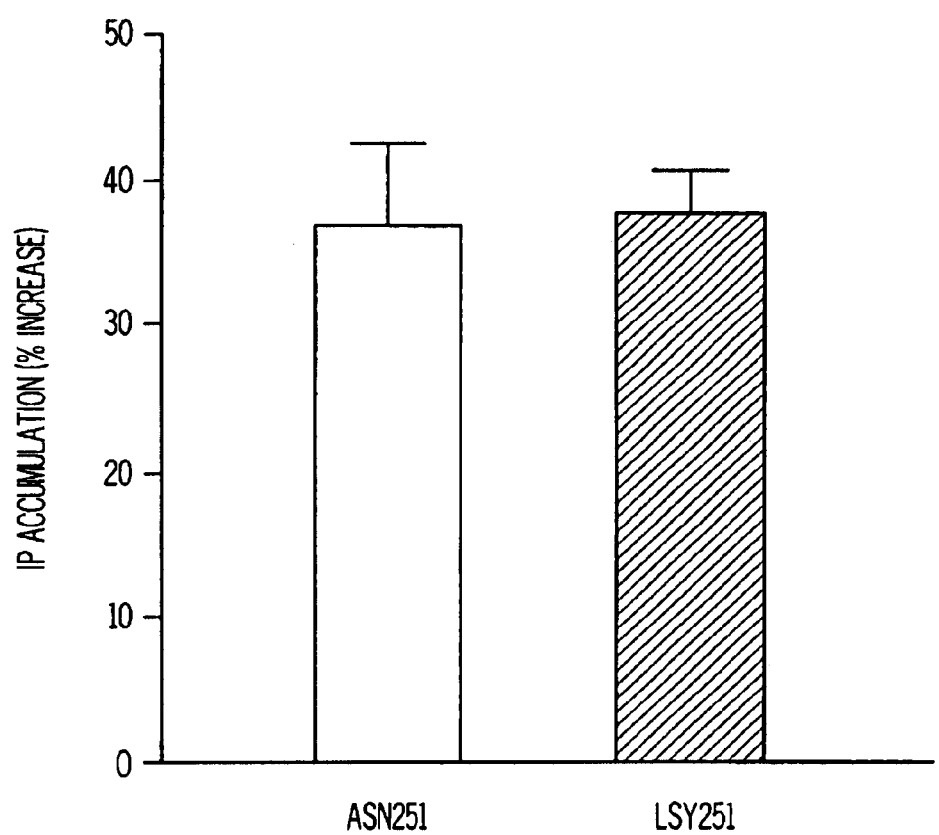
FIG. 10 is a bar graph illustration of stimulation of inositol phosphate accumulation by wild-type Asn251 and polymorphic Lys251 alpha-2AARs. Total inositol phosphate production in intact CHO cells was measured as described below in response to a 5 minute exposure to 10 µM epinephrine. Results are from five experiments.

To investigate the extent of MAP kinase activation in CHO cell lines expressing both the Asn251 and Lys251 receptors, quantitative immunoblots using an antibody specific to the activated (phosphorylated) form of ERK 1/2 were performed. While the total amount of MAP kinase was not different (FIG. 9A), agonist-promoted stimulation of MAP kinase activity was markedly different between the two cell lines (FIG. 9A, B). Activation of the Lys251 receptor with 10 μM epinephrine resulted in a 57±9 fold increase in MAP kinase activity over basal as compared to 15±2.1 fold increase with the Asn251 receptor (n=3, p=<0.05).

Finally, coupling of these two receptors to the stimulation of inositol phosphate production was examined. Such $\alpha_2$AR signaling is a complex response due to activation of phospholipase C by βγ released from activated $G_o$ and $G_i$ (25). In contrast to the [$^{35}$S]GTPγS binding, adenylyl cyclase, and MAP kinase results, the maximal extent of epinephrine-stimulated accumulation of inositol phosphates was not found to be different between Lys251 and Asn251 expressing cells (FIG. 6). However, the signal transduction of the LYS251 receptor was nevertheless enhanced, as evidenced by a decrease in the $EC_{50}$ (wildtype=493 mm, Lys251=119 mm, P<0.05).

Alpha-2AARs are widely expressed throughout the nervous system and peripheral tissues. Recent work with relatively selective agonists and antagonists, radiolabels, and specific molecular probes in several species, including genetically engineered mice, have begun to elucidate specific functions for the various alpha-2AAR subtypes (26). The latter studies have been particularly useful in identifying subtype-specific functions. Mice lacking alpha-2AARs have higher resting systolic blood pressures and more rapidly develop hypertension with sodium loading after subtotal nephrectomy than wild-type mice (27). Furthermore, these alpha-2AAR knock-out mice fail to display a hypotensive response to the agonist dexmedetomidine (5). Heart rates in these mice were increased at rest, which correlated with increased [$^3$H]norepinephrine release from cardiac sympathetic nerves. These data thus indicate that the presynaptic inhibition of neurotransmitter release in cortical and cardiac nerves serves important homeostatic functions in blood pressure and cardiac function. And, that the physiologic effects of therapeutic agonists such as clonidine reduce blood pressure by specifically acting at the alpha-2AAR subtype. The lack of a hypotensive effect of alpha-2AAR agonists has also been shown in genetically altered (hit-and-run) mice expressing a dysfunctional alpha-2AAR (D79N) (28). These mice also responded poorly to alpha-2AAR agonists for several other physiologic functions (6). Dexmedetomidine failed to reduce rotarod latency or induce prolongation of sleep time, to enhance the efficacy of halothone, or to attenuate thermally induced pain in these mice. Thus the sedative, anesthetic-sparing, and analgesic effects of alpha-2AAR agonists are due to activation of the alpha-2AAR subtype. Indeed, these physiologic defects correlated with absent $\alpha_{2A}$AR regulation of inwardly rectifying $K^+$ channels of locus ceruleus neurons and voltage gated $Ca^{2+}$ channels of these same neurons, as well as those of the superior cervical ganglion (6).

Examples 7–14 indicate that a polymorphism resulting in a markedly depressed alpha-2AAR function in humans would likely be of physiologic importance. Indeed, such a polymorphism can be a significant risk factor for hypertension. However, the one coding block polymorphism that we found in Caucasians and African-Americans is not associated with essential hypertension and in fact its phenotype is a gain of function. It should be noted that with our sample size we have the power to detect a polymorphism with an allele frequency of 0.04 with a statistical certainty of 90%, thus it is unlikely that we have failed to detect another polymorphism that is common in any of the cohorts. Based on the phenotype of the Lys251 receptor, and the known physiologic function of the alpha-2AAR, one can predict that the polymorphism would predispose to autonomic dysfunction characterized by hypotension and bradycardia. Similarly, patients with essential hypertension who have the polymorphism can have milder disease or display enhanced efficacy of antihypertensive agents such as clonidine or guanabenz. Interestingly, these individuals may display more pronounced central nervous system side-effects from these agents, such as sedation, which could ultimately limit their therapeutic utility. Finally, the hyperfunctioning polymorphism would be predicted to result in less norepinephrine release from cardiac sympathetic nerves, thereby potentially providing protection against the deleterious effects of catecholamines in patients with heart failure.

Mutations of G-protein coupled receptors are the basis of a number of rare diseases (29). In contrast, polymorphisms (allele frequencies >1%) of these receptors have been identified which can be minor risk factors for complex diseases (30), but more importantly act as disease modifiers (31) or alter response to therapeutic agents targeting the receptor (32). Interestingly, when such mutations or polymorphisms have been found to alter function, the minor allelic variant (i.e., the least common form of the receptor) results in either decreased agonist-promoted function or increased non-agonist dependent function (i.e., constitutive activation). An example of the former is the Ile164 polymorphisms of the $\beta_2$AR, which imparts defective agonist-promoted coupling to $G_s$ (33). Constitutive activation results in receptors adopting a mutation induced agonist-bound like state and thus signaling becomes independent of agonist. Such persistent activation is the pathologic basis for diseases such as male precocious puberty, which is due to a mutation in the leutinizing hormone receptor (34). In the current report we show that the Lys251 receptor does not exhibit constitutive activation, based on wild-type [$^3$S]GTPγS binding, adenylyl cyclase, and MAP kinase activities in the absence of agonist. Instead, the phenotype that we observed was one of increased agonist-promoted function. To our knowledge this is the first delineation of a polymorphism of a pharmacogenetic locus of any G-protein coupled receptor where the minor allele displays this property, and thus this represents a new class of polymorphism for the superfamily.

Examples 15–21 below demonstrate that a polymorphism of the alpha-2AR subtype localized to human chromosome 4 (the pharmacologic alpha-2CAR subtype) within an intracellular domain has been identified in normal individuals. The polymorphism with amino acid deletions in positions 322–325 of the alpha-2CAR (denoted Del322–325) is due to an in-frame 12 nucleic acid deletion encoding a receptor lacking Gly-Ala-Gly-Pro in the third intracellular loop. Agonist binding studies showed decreased high affinity binding to the polymorphic receptor. To delineate the functional consequences of this structural alteration, Chinese hamster ovary cells were permanently transfected with constructs encoding wild-type human alpha-2CAR and the polymorphic receptor. The Del322–325 variant displayed markedly depressed epinephrine-promoted coupling to $G_i$, inhibiting adenylyl cyclase by 10±4.3% compared to 73±2.4% for wild-type alpha-2CAR. This also was so for the endogenous ligand norepinephrine and full and partial synthetic agonists. Depressed agonist-promoted coupling to the stimulation of MAP kinase (~71% impaired) and inositol phosphate production (~60% impaired) was also found with the polymorphic receptor. The Del322–325 receptor was ~10 times more frequent in African-Americans compared to Caucasians (allele frequencies 0.381 vs 0.040). Given this significant loss-of-function phenotype in several signal transduction cascades and the skewed ethnic prevalence, Del322–325 represents a pharmacoethnogenetic locus and can be the basis for interindividual variation in diseases, such as cardiovascular or CNS pathophysiology.

Example 15
Polymorphism Detection

The nucleotide sequence encoding the third intracellular loop of the human alpha-2C adrenergic receptor (SEQ ID NO: 40) was examined for polymorphic variation by performing polymerase chain reactions (PCR) to amplify this portion of the cDNA from genomic DNA derived from blood samples. For convenience, the adenine of the initiator ATG codon is designated as nucleotide 1 and amino acid 1 is the encoded methionine. The human receptor consists of 462 amino acids. For initial examination, DNA from 20 normal individuals was utilized. Primers for PCR were:

```
                                           SEQ ID NO:48
5'-CCACCATCGTCGCCGTGTGGCTCATCT-3' (sense)
and SEQ ID NO:49
5'-AGGCCTCGCGGCAGATGCCGTACA-3' (antisense).
```

The PCR consisted of ~100 ng genomic DNA, 5 pmol of each M13 primer, 0.8 mM dNTPs, 10% DMSO, 2.5 units Platinum taq DNA polymerase High Fidelity (Gibco/BRL), 20 uL 5× buffer E (Invitrogen) in a 100 µl reaction volume. Reactions were started by an initial incubation at 94° C. for four minutes, followed by 35 cycles of 94° C. for 30 seconds, 65° C. for 30 seconds, and 72° C. for one minute, followed by a final extension at 72° C. for seven minutes. Attempts to directly sequence this product resulted in ambiguous reads, so the product was ligated into the vector PCR2.1-TOPO (Invitrogen) and TOP 10 cells were transformed. Multiple colonies from each transformation were expanded and the subsequently isolated DNA was sequenced using an ABI 373A automated sequencer in the forward and reverse directions using dye terminator chemistry, such as dideoxy nucleotides, with vector T7 and M13 primers. As is discussed, a 12 bp deletion was found in some individuals beginning at nucleotide 964 of FIG. 11. This results in the loss of amino acids 322–325 and thus this polymorphic receptor is denoted Del 322–325. This deletion results in the loss of a Nci I restriction site at nucleotide 974 (forward strand), and thus a rapid detection method was devised. Smaller (384 and 372 base-pair) PCR products were produced using 5'-AGCCCGACGAGAGCAGCGCA-3' SEQ ID NO: 50 as the sense primer and the aforementioned antisense primer (same reaction conditions as above) and genomic DNA derived from blood samples as the template. Within this fragment there are either five or six Nci restriction sites depending on the presence or absence of the deletion, providing for the pattern shown in FIG. 11C. This rapid detection technique was applied to additional DNA samples providing genotypes at this locus from a total of 146 individuals. No other nonsynonymous polymorphisms were found in the third intracellular loop sequence. However, five synonymous single nucleotide polymorphisms were found at nucleic acids 868, 871, 933, 996 and 1167.

Example 16
Constructs and Cell Transfection

To create the polymorphic alpha-2CAR construct the larger (723 bp) PCR product described above amplified from a homozygous individual was digested and subcloned into the Bpu1102 I and Eco47 III sites of the wild-type alpha- 2CAR sequence in the expression vector pBC12BI (Eason et al. *J. Biol. Chem.* 267, 25473–25479 (1992)). The integrity of the construct was verified by sequencing. Chinese hamster ovary cells (CHO-K1) were permanently transfected by a calcium phosphate precipitation technique as previously described using 30 μg of each receptor construct and 0.5 μg of pSV$_2$neo to provide for G418 resistance (Eason et al. *J. Biol. Chem.* 267, 25473–25479 (1992)). Selection of positive clones was carried out in 1.0 mg/ml G418 and expression of the alpha-2C receptors from individual clonal lines was determined by radioligand binding as described below. Cells were grown in monolayers in Ham's F-12 medium supplemented with 10% fetal calf serum, 100 units/ml penicillin, 100 μg/ml streptomycin and 80 μg/ml G418 (to maintain selection pressure) at 37° C. in a 5% CO$_2$ atmosphere.

Example 17
Adenylyl Cyclase Activity

Alpha-2AR inhibition of adenylyl cyclase was determined in membrane preparation from CHO cells stably expressing the two receptors using methods similar to those previously described (Eason et al. *J. Biol. Chem.* 267, 25473–25479 (1992)). Briefly, membranes (~20 μg) were incubated with 27 μM phosphoenolpyruvate, 0.5 μM GTP, 0.1 mM cAMP, 0.12 mM ATP, 50 μg/ml myokinase, 0.05 mM ascorbic acid and 2 μCi of [alpha-$^{32}$P]ATP in a buffer containing 40 mM HEPES, pH 7.4, 1.6 mM MgCl$_2$ and 0.8 mM EDTA for 30 minutes at 37° C. These conditions minimize the stimulation of adenylyl cyclase which is observed at high agonist concentrations (Fraser et al. *J. Biol. Chem.* 264, 11754–11761 (1989); Eason et al. *J. Biol. Chem.* 267, 15795–15801 (1992)). Reactions were terminated by the addition of a stop solution containing excess ATP and cAMP and ~100,000 dpm of [$^3$H]cAMP. Labeled cAMP was isolated by gravity chromatography over alumina columns with [$^3$H]cAMP used to quantitate column recovery. Activities were measured in the presence of water (basal), 5 μM forskolin, and 5 μM forskolin with the indicated concentrations of agonists. Results are expressed as percent inhibition of forskolin stimulated activity.

Example 18
MAP Kinase Activation

Activation of p44/42 MAP kinase was determined by quantitative immunoblotting using a phospho-specific antibody. Briefly, confluent cells were incubated overnight at 37° C. and 5% CO$_2$ in serum-free media prior to treatment with media alone (basal), epinephrine (10 μM), or thrombin (1 unit/ml) for 5 min. Cells were washed three times with phosphate-buffered saline (PBS) then lysed in RIPA buffer (20 mM Tris, pH 7.5, 150 mM NaCl, 1 mM EDTA, 1% NP-40, 0.5% deoxycholate, 0.1% SDS, and 5 mM NaF) containing protease inhibitors (10 μg/ml benzamidine, 10 μg/ml soybean trypsin inhibitor, 10 μg/ml aprotinin, and 5 μg/ml leupeptin). Western blots of these whole cell lysates were performed essentially as previously described (18) except that PVDF membranes (Amersham) were used and incubated with phospho-p44/42 MAP kinase E10 antibody, and (after stripping) with the p44/42 MAP kinase monoclonal antibody (both from New England Biolabs, Beverly, Mass.) at dilutions of 1:2000 for 1 hr at room temperature. Washed membranes were subsequently incubated with anti-mouse fluorescein-linked immunoglobulin followed by incubation with fluorescein alkaline phosphatase (ECF, Amersham). Fluorescent signals were quantitated by real-time acquisition using a Molecular Dynamics STORM imager.

Example 19
Inositol Phosphate Accumulation

Total inositol phosphate levels in intact cells were determined essentially as described previously (Schwinn et al. *Mol. Pharmacol.* 40, 619–626 (1991)). Briefly, confluent CHO cells stably expressing each of the $\alpha_{2C}$ARs were incubated with [$^3$H]myoinositol (5 μCi/ml) in media lacking fetal calf serum for 16 hrs at 37° C. in 5% CO$_2$ atmosphere. Subsequently, cells were washed and incubated with PBS for 30 min followed by a 30 min incubation with 20 mM LiCl in PBS. Cells were then treated with PBS alone (basal), 10 μM epinephrine, or 5 units/ml thrombin for 5 min, and inositol phosphates were extracted as described by Martin (Martin, T. F. J. *J Biol Chem* 258, 14816–14822 (1983)). Following separation on Agl-X8 columns, total inositol phosphates were eluted with a solution containing 0.1 M formic acid and 1 M formate.

Example 20
Radioligand Binding

Expression of mutant and wild-type alpha-2CAR was determined using saturation binding assays as described (Eason et al. *Proc. Natl. Acad. Sci., USA* 91, 11178–11182 (1994)) with 12 concentrations (0.5–30 nM) of [$^3$H] yohimbine and 10 μM phentolamine used to define nonspecific binding. For competition studies, membranes were incubated in 50 mM Tris-HCL, pH 7.4, 10 mM MgSO$_4$, 0.5 mM EDTA with 2.0 nM [$^3$H]yohimbine and 16 concentrations of the indicated competitor for 30 minutes at 37° C. Reactions for the above radioligand binding studies were terminated by dilution with 4 volumes of ice cold 10 mM Tris-HCL, pH 7.4 buffer and vacuum filtration over Whatmann GF/C glass fiber filters.

Example 21
Protein Determination and Data Correlation

Protein determinations were by the copper bicinchoninic acid method (Smith et al. *Anal. Biochem.* 150, 76–85 (1985)). Data from adenylyl cyclase and radioligand binding assays were analyzed by iterative least-square techniques using Prizm software (GraphPad, San Diego, Calif.). Agreement between genotypes observed and those predicted by the Hardy-Weinberg equilibrium was assessed by a Chi-squared test with one degree of freedom. Comparisons of results from biochemical studies were paired by t-tests and significance was considered when p<0.05. Data are provided as means standard errors.

Results and Discussion of Examples 15–21

From the initial sequencing of alpha-2CAR third intracellular loop PCR products from 40 chromosomes, one nonsynonymous sequence variant was identified (FIG. 11). This consisted of an in-frame 12 nucleotide (SEQ ID NO: 41 ggggcggggccg, sense strand) deletion beginning at nucleotide 964 of FIG. 11. This results in a loss of Gly-Ala-Gly-Pro at amino acid positions 322–325 within the third intracellular loop of the receptor (FIG. 12) SEQ ID NO: 45. The frequencies of the wild-type and the Del322–325 polymorphic alpha-2CARs are shown in Table 5. The polymorphism is rare in Caucasians with an allelic frequency of 0.040. In contrast, the frequency is ~10-fold higher (0.381) in African-Americans. The distribution of homozygous and heterozygous alleles was not different than that predicted from the Hardy-Weinberg equilibrium (p>0.8).

TABLE 5

Frequencies of the Del322–325 alpha-2CAR polymorphism

| | N | WT Homozygous | Heterozygous | Del 322–325 Homozygous | Allele Frequency Del 322–325 |
|---|---|---|---|---|---|
| Caucasian | 87 | 82 | 3 | 2 | 0.040 |
| African-American | 59 | 23 | 27 | 9 | 0.381 |

Shown are the number of individuals with each genotype out of a total of N individuals.

The consequences of this polymorphism on receptor function were evaluated by permanently expressing the human wild-type alpha-2CAR and the Del322–325 receptor in CHO cells and examining multiple signaling pathways. As indicated, multiple clones with similar expression levels were utilized for these studies. Saturation radioligand binding studies using the alpha-2AR antagonist [$^3$H]yohimbine revealed that Del322–325 had a slightly, but statistically significant, lower affinity for the radioligand compared to wild-type alpha-2CAR ($K_d$=3.8 0.55 vs 2.0 0.14 nM, n=5, p=0.03). In competition studies with the agonist epinephrine, carried out in the absence of GTP, high- and low-affinity binding was detected with both receptors. However the high affinity dissociation constant $K_H$ for the Del322–325 mutant was greater (i.e., lower affinity) compared to the wild-type receptor (7.3 0.95 vs 3.7 0.43 nM, n=4, p=0.01. And, the percentage of receptors in the high-affinity state was less with the mutant receptor (% $R_H$ 32 31 4 vs 49 4, p=0.01). The $K_L$ values were not different (584 71 vs 416 75 nM). Taken together, this indicates impaired formation of the high affinity agonist-receptor-$G_i/G_o$ complex.

TABLE 6

Adenylyl cyclase activities of the wild-type and Del322–325 alpha-2CAR for full and partial agonists.

| | Max Inhibition (%)* | | $EC_{50}$ (nM) | |
|---|---|---|---|---|
| Agonist | WTα$_{2C}$AR | Del322–325 | WTα$_{2C}$AR | Del322–325 |
| Norepinephrine | 76.6 ± 1.60 | 34.9 ± 0.887 | 219 ± 13.7 | 224 ± 70.7 |
| UK 14304 | 67.6 ± 2.09 | 30.8 ± 4.68 | 131 ± 31.0 | 109 ± 24.1 |
| BHT-933 | 56.8 ± 1.41 | 26.7 ± 2.40 | 5500 ± 2110 | 4080 ± 2005 |
| guanabenz | 53.8 ± 1.99 | 30.0 ± 1.98 | | |
| clonidine | 38.5 ± 2.44 | 20.9 ± 1.28 | 262 ± 26.1 | 178 ± 43.8 |
| oxymetazoline | 27.0 ± 2.70 | 12.8 ± 1.40 | 32.2 ± 1.66 | 29.1 ± 0.565 |

α: Adenylyl cyclase assays were performed on membranes prepared from CHO cell lines expressing wild-type and Del322–325 alpha-2CAR at 1570 ± 79.9 and 1520 ± 27.6 fmol/mg, respectively, as described above.
*p < 0.05 compared to the wild-type alpha-2CAR (n = 3 or 4 experiments).

Figure 13A:
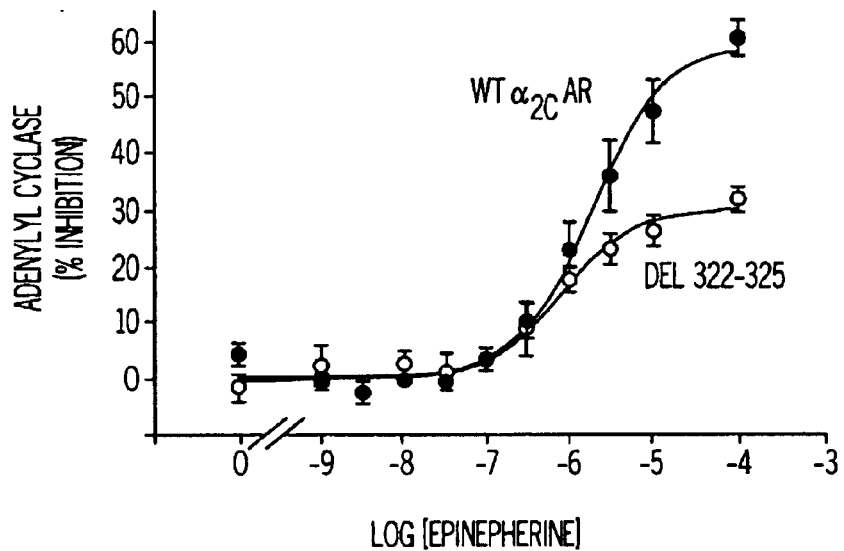
FIG. 13 is a graphic illustration of the coupling of wild-type and mutant with deletions in amino acids 322–325 (Del322–325) alpha-2CARs to the inhibition of adenylyl cyclase. Membranes from CHO cells were prepared and adenylyl cyclase activities determined in the presence of 5.0 µM forskolin and the indicated concentrations of epinephrine. Results are shown as the percent inhibition of forskolin stimulated activities. (For all cell lines the fold stimulation by forskolin was ~10 fold over basal levels). Panel A shows results from two cell lines expressing the wild-type and Del322–325 receptors at ~1380±140 and ~1080±160 fmol/mg. Panel B shows results from lower levels of expression in two other cell lines with densities of 565±69 and 520±51 fmol/mg, respectively. Results are from 5 experiments. *, $p<0.001$ for the maximal inhibition compared to wild-type.

The location of the deletion in the third intracellular loop of the receptor is within 15 residues of the sequence RRG-GRR SEQ ID NO: 51. This is a motif that has been identified in a number of receptors as a $G_i$ coupling domain (Okamoto et al. *J. Biol. Chem.* 267, 8342–8346 (1992); Ikezu et al. *FEBS* 311, 29–32 (1992)). The deletion of the two glycines or the proline in the Del322–325 receptor induces conformational changes affecting this region or other G-protein coupling domains. Functional studies examining agonist-promoted inhibition of forskolin stimulated adenylyl cyclase activities were carried out in lines with the wild-type alpha-2CAR and the Del322–325 receptor at expression levels of 1375±141 vs 1081±157 fmol/mg (n=5, p>0.05) and a second set of lines with lower expressions of 565±69 vs 519±51 fmol/mg (n=5, p>0.05), respectively. The results of these studies are shown in FIG. 13. As can be seen, there is a marked functional difference between the two receptors. In the higher expressing lines (FIG. 13A), wild-type alpha-2CAR exhibited a maximal inhibitory response of 60±3%. In contrast, the Del322–325 polymorphic receptor achieved a maximal inhibition of 31±2% (n=5, p<0.001), which represents an ~50% impairment of function. Of note, the $EC_{50}$s for these responses (2.6±0.74 vs 1.2±0.37 nM, respectively) were not different.

Figure 13B:
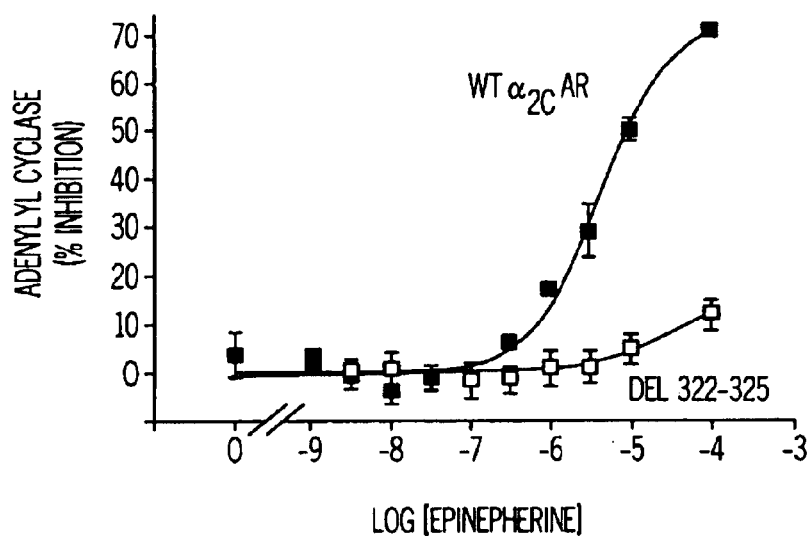

Results from studies with the lower expressing lines revealed an even more striking phenotypic difference between the two receptors. As is shown in FIG. 13B, at these more physiologic levels of expression, agonist-promoted inhibition of adenylyl cyclase with wild-type alpha-2CAR was 73±2.4%. In marked contrast, the Del322–325 receptor exhibited very little inhibition (10±4.3%, n=5, p<0.001). With the low expressing Del322–325 line the $EC_{50}$ in some experiments could not be calculated due to the minimal response. Analysis of the composite curve of the mean data from the above examples with this line revealed an $EC_{50}$ of 29.6 nM. This is in contrast to 4.3 nM calculated in a like manner for the low expressing wild-type line. A similar degree of impairment was also observed with the endogenous agonist norepinephrine (Table 6). Agonist-promoted functional activities of the two higher expressing receptors were also explored with full and partial synthetic alpha-2AR agonists with diverse structures. As is shown in Table 6, the Del322–325 receptor has depressed agonist-promoted coupling to inhibition of adenylyl cyclase with all the agonists tested.

Figure 14:
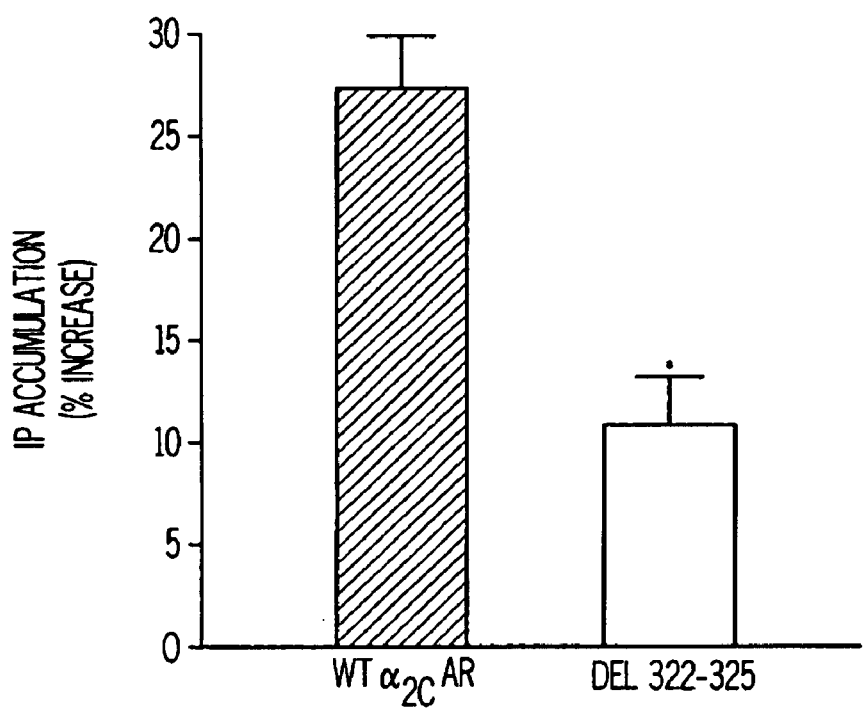
FIG. 14 is a bar graph illustration of stimulation of inositol phosphate accumulation by wild-type and Del322–325 alpha-2CARs. Total inositol phosphate production in intact CHO cells was measured in response to 5 minute exposure to 10 µM epinephrine. Receptor expression was 806±140 and 733±113 fmol/mg, respectively, for these experiments. *, $p<0.005$ compared to wild-type response (n=4 experiments).

We next explored coupling of these two receptors (mutant and wild-type) to the stimulation of inositol phosphate production. In CHO cells this response is ablated by pertussis toxin, indicating coupling via $G_i$ and/or $G_o$ (Dorn et al. *Biochem* 36, 6415–6423 (1997)). The activation of phopholipase C is likely due to both $G_o$-alpha mediated stimulation and $G_i$ associated G beta gamma stimulation of the enzyme (Dom et al. *Biochem* 36, 6415–6423 (1997)). As shown in FIG. 14, the loss-of-function phenotype of the Del322–325 receptor as delineated in adenylyl cyclase experiments was also observed in these inositol phosphate accumulation studies. Epinephrine-stimulated accumulation of inositol phosphates was 30±3% over basal with the wild-type alpha-2CAR, compared to 11±2% for the Del322–325 receptor (n=4, p<0.005) which amounts to an ~60% impairment of function for the polymorphic receptor. Expression levels for the two receptors for these experiments were 806±140 and 733±113 respectively.

Agonist mediated stimulation of MAP kinase was examined. The mechanism of G protein coupled receptor mediated stimulation of this pathway is multifactorial and is both receptor and cell-type dependent (Luttrell et al. *Adv Second Messenger Phosphoprotein Res* 31, 263–277 (1997)). For the beta2AR, coupling to $G_i$, internalization of the receptor, and interaction with beta-arrestin is required for this receptor to activate the MAP kinase cascade. Alpha-2AR coupling to this pathway is pertussis toxin sensitive and receptor internalization is not necessary (Schramm et al. *J Biol Chem* 274, 24935–24940 (1999)). For present studies, MAP kinase activation was assessed using quantitative immunoblots with an antibody specific for the activated (phosphorylated) form of Erk1/2. The total amount of MAP kinase was not different between the two cell lines utilized (FIG. 15A). Agonist promoted activation of MAP kinase was significantly different between the two receptors (FIG. 15), with results expressed both as the agonist-promoted fold increase over basal levels of activated MAP kinase and as the percent of the thrombin response. In five such experiments, MAPK activity in Del322–325 expressing cells in response to 10 µM epinephrine was 57.8±7.0% of the WT alpha-2CAR response (p<0.005), and the stimulation as a percent of the thrombin response was 128±10.0 vs 37.2±5.7 (p<0.005), respectively.

Recent studies have begun to elucidate specific functions for the alpha-2CAR subtype. In situ mRNA and immunohistochemical analysis of alpha-2CAR expression has revealed a distinct pattern of expression in rat brain and spinal cord (Rosin et al. *J Comp Neurol* 372, 135–165 (1996); Shi et al. *Neuroreport* 10, 2835–2839 (1999)). Alpha-2CARs have been localized primarily in the neuronal perikarya and to a lesser extent in the proximal dendrites, with high levels of receptor expression detected in the basal ganglia, olfactory tubercle, hippocampus, and cerebral cortex (Rosin et al. *J Comp Neurol* 372, 135–165 (1996)). These data along with studies of genetically engineered mice indicate that the alpha-2CAR subtype plays explicit roles in cognitive and behavioral functions. Studies of mice that overexpress, or that have targeted inactivation of, the alpha-2CAR gene have shown that this receptor is involved in the regulation of spontaneous motor activity as well as agonist-induced regulation of body temperature and dopamine metabolism (Sallinen et al. *Mol. Pharmacol.* 51, 36–46 (1997)).

In addition, results indicating that activation of alpha-2CAR reduces hyperreactivity and impulsivity have also been reported (Sallinen et al. *The Journal of Neuroscience* 18, 3035–3042 (1998)). These studies show that lack of alpha-2CAR expression is associated with increased startle reactivity, reduced prepulse inhibition of the startle reflex, and isolation induced attack latency, while overexpression of alpha-2CAR produces the opposite effects. Consistent with these data, in humans, the alpha-2AR agonist clonidine and the alpha-2AR antagonist idazoxan reduce and facilitate the acoustic startle response, respectively (Morgan et al. *Psychopharmacology* 110, 342–346 (1993); Kumari et al. *Psychopharmacology* 123, 353–360 (1996)). The role of alpha-2CAR in modulating working memory has also been characterized (Tanila et al. *European Journal of Neuroscience* 11, 599–603 (1999)). In these studies, alpha-2CAR knockout mice performed less accurately in a delayed alternation task and displayed slowed motor initiation in the return phase of the task, supporting a role for the alpha-2CAR in the cognitive aspect of response preparation. Alpha-2CAR knockout mice were also impaired in spatial and non-spatial water maze tests, thus supporting a role for this receptor in modulating cognitive functions (Bjorklund et al. *Mol Pharmacol* 54, 569–576 (1998)), and alteration of alpha-2CAR expression in transgenic mice has also been linked with behavioral despair development and changes in plasma corticosterone levels (Sallinen et al. *Mol Psychiatry* 4, 443–452 (1999)).

Recent studies measuring [$^3$H]norepinephrine release from central neurons and cardiac sympathetic nerves have shown that the frequency-release curves for alpha-2CAR deficient mice are rightward shifted compared to wild-type mice (Hein et al. *Nature* 402, 181–184 (1999)). Furthermore, the residual agonist-stimulated inhibition of [$^3$H] norepinephrine release observed in alpha-2AAR deficient mice was not present in mice deficient in both alpha-2A and alpha-2CAR. Thus both subtypes are important in inhibiting neurotransmitter release at these sites. Alpha-2CAR mRNA or receptor protein has also been identified in other peripheral sites (Gavin et al. *Naunyn Schmiedebergs Arch Pharmacol* 355, 406–411 (1997); Eason et al. *Mol. Pharmacol.* 44, 70–75 (1993); Adolfsson et al. *Gynecol Obstet Invest* 45, 145–150 (1998)) with evidence in some cases indicative of postsynaptic functions (Gavin et al. *Naunyn Schmiedebergs Arch Pharmacol* 355, 406–411 (1997)).

The presence of functionally distinct polymorphic alpha-2CARs accounts for interindividual variability in physiological responses, and is the basis of differences in clinical characteristics of diseases where alpha-2CAR function is important. In addition, the Del322–325 polymorphism can predispose individuals to the development of disease. The results show that response to agonist or antagonist therapeutic agents may also vary depending on receptor genotype. In this regard individuals with Del322–325 are more sensitive to antagonists since they have receptors which are less responsive to endogenous catecholamines. For agonists, the response or sensitivity would be predicted to be less for those with the polymorphic alpha-2CAR due to its impaired coupling. The results discussed in Table 5 show relatively high frequency of the polymorphism in healthy African-Americans, and modification of a disease or drug-response. We and others have recently shown that functional polymorphisms of the $\alpha_2$AR indeed appear to have one or more of the above effects in asthma, congestive heart failure, and obesity (Tan et al. *Lancet* 350, 995–999 (1997); Tan et al. *Lancet* 350, 995–999 (1997); Large et al. *J Clin Invest* 100, 3005–3013 (1997)). Interestingly, Comings et al (Comings et al. *Clin Genet* 55, 160–172 (1999)) have found that increased levels of plasma norepinephrine levels in children with attention-deficit hyperactivity disorder (ADHD) with learning disabilities were associated with polymorphisms near the coding regions of the alpha-2A, alpha-2C, and dopamine β-hydroxylase (DBH) genes.

In summary, examples 15–21 demonstrate that a polymorphic alpha-2CAR has been identified that includes a deletion of four amino acids in the third intracellular loop of the receptor. Such a deletion has a significant effect on agonist-promoted inhibition of adenylyl cyclase, stimulation of inositol phosphate accumulation and activation of MAP kinase. For all three effector pathways, the Del322–325 receptor displays markedly impaired coupling. The polymorphism is rare in Caucasians, but is ~10 fold more prevalent in African-Americans with an allele frequency of 0.381. To our knowledge, this is the greatest racial difference in a polymorphism of any G-protein coupled receptor reported to date. Given the extreme phenotype, this locus is considered a basis for interindividual variation in physiologic responses, disease predisposition, or modification, and drug responsiveness.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice thin the art to which the invention pertains and as may be applied to the essential features hereinbefore set forth and as follows in the scope of the appended claims.

TABLE 7

Frequency of the Alpha-2BAR Del301–303 polymorphism.

| | n | Wt Homozygous | Heterozygous | Del301–303 Homozygous | Del301–303 Allele Frequency |
|---|---|---|---|---|---|
| Caucasian | 94 | 41 | 47 | 6 | 0.31 |
| African-American | 79 | 61 | 17 | 1 | 0.12 |

TABLE 8

Ligand binding properties of wild-type and Del301–303 alpha-2BAR expressed in CHO cells

| | [$^3$H]-yohimbine | | | | | | [$^{125}$I]-aminoclonidine | |
|---|---|---|---|---|---|---|---|---|
| | saturation binding | | epinephrine competition | | | | saturation binding | |
| Receptor | $B_{max}$ (fmol/mg) | $K_D$ (nM) | $K_i$ | $K_H$ (nM) | $K_L$ (nM) | % $R_H$ | $B_{max}$ (fmol/mg) | $K_D$ (nM) |
| Wild-Type | 671 ± 56 | 3.8 ± 0.3 | 285 ± 8.7 | 2.9 ± 0.8 | 346 ± 111 | 41 ± 4 | 118 ± 27 | 1.33 ± 0.12 |
| Del301–303 | 538 ± 79 | 5.1 ± 0.2* | 376 ± 66* | 4.1 ± 1.2 | 357 ± 135 | 42 ± 5 | 106 ± 20 | 1.22 ± .07 |

Saturation binding isotherms and competition studies were carried out with membranes from CHO cells expressing equivalent levels of receptor.
* = p < 0.05 compared to wild-type alpha-2BAR.

TABLE 9

Adenylyl cyclase activities of the wild-type and Del301–303 alpha-2BAR expressed in CHO cells

| | Basal | Forskolin | Max Inhibition | | Submax inhibition (%) | | Desensitization |
|---|---|---|---|---|---|---|---|
| | pmol/min/mg | | (%) | $EC_{50}$ (nM) | Ctrl | NE | (%) |
| Wild Type | 2.0 ± 0.2 | 15.1 ± 0.9 | 28.5 ± 1.6 | 7.9 ± 2.1 | 16.5 ± 3.9 | 7.6 ± 2.3† | 54 |
| Del301–303 | 1.2 ± 0.1* | 11.9 ± 0.9* | 23.4 ± 2.2* | 19.6 ± 5.5* | 17.1 ± 3.0 | 15.9 ± 1.7* | 7 |

Adenylyl cyclase activities were determined in membranes in response to forskolin (5 μM) and forskolin plus various concentrations of norepinephrine. See also FIG. 3.
* = p < 0.05 compared to wild-type alpha-2BAR.
† = p < 0.05 compared to control.

---

What is claimed is:

1. An isolated polynucleotide encoding an alpha-2C adrenergic receptor molecule or fragment or complement of the polynucleotide, having a polymorphic site comprising ggggcggctgag; SEQ ID NO: 43 at nucleotide positions 964 to 975.

2. An isolated polynucleotide according to claim 1, wherein the polynucleotide comprises ggggcggctgag; SEQ ID NO: 43 at nucleotide positions 964 to 975 with up to 20 additional nucleotides on either the 5" or 3" end or both.

3. An isolated oligonucleotide that specifically hybridizes to a region of a polynucleotide encoding an alpha-2C adrenergic receptor molecule or fragment of the polynucleotide, wherein the region comprises at least one polymorphic site comprising ggggcggctgag; SEQ ID NO: 43 at nucleotide positions 964 to 975 wherein the oligonucleotide permits identification of one polymorphic site comprising ggggcggctgag; SEQ ID NO: 43 at nucleotide positions 964 to 975.

4. An isolated oligonucleotide according to claim 3, wherein the oligonucleotide is a primer that specifically hybridizes to a region immediately adjacent to nucleotide positions 964 to 975.

* * * * *

UNITED STATES PATENT AND TRADEMARK OFFICE
CERTIFICATE OF CORRECTION

| | | |
|---|---|---|
| PATENT NO. | : 7,041,810 B2 | |
| APPLICATION NO. | : 10/001073 | |
| DATED | : May 9, 2006 | |
| INVENTOR(S) | : Kersten M. Small and Stephen B. Liggett | |

It is certified that error appears in the above-identified patent and that said Letters Patent is hereby corrected as shown below:

In the Specification

At Column 1, line 16-19, paragraph [0002], please replace the entire paragraph with the following paragraph:

This invention was made with government support under ES06096 and HL53436 awarded by National Institutes of Health. The government has certain rights in the invention.

Signed and Sealed this
Twelfth Day of May, 2015

Michelle K. Lee
*Director of the United States Patent and Trademark Office*

SEQUENCE LISTING

<160> NUMBER OF SEQ ID NOS: 69

<210> SEQ ID NO 1
<211> LENGTH: 1353
<212> TYPE: DNA
<213> ORGANISM: Homo sapiens

<400> SEQUENCE: 1

```
atggaccacc aggacccta ctccgtgcag gccacagcgg ccatagcggc ggccatcacc      60
ttcctcattc tctttaccat cttcggcaac gctctggtca tcctggctgt gttgaccagc       120
cgctcgctgc gcgcccctca gaacctgttc ctggtgtcgc tggccgccgc cgacatcctg      180
gtggccacgc tcatcatccc tttctcgctg gccaacgagc tgctgggcta ctggtacttc      240
cggcgcacgt ggtgcgaggt gtacctggcg ctcgacgtgc tcttctgcac ctcgtccatc      300
gtgcacctgt gcgccatcag cctggaccgc tactgggccg tgagccgcgc gctggagtac      360
```

```
aactccaagc gcaccccgcg ccgcatcaag tgcatcatcc tcactgtgtg gctcatcgcc      420
gccgtcatct cgctgccgcc cctcatctac aagggcgacc agggccccca gccgcgcggg      480
cgcccccagt gcaagctcaa ccaggaggcc tggtacatcc tggcctccag catcggatct      540
ttctttgctc cttgcctcat catgatcctt gtctacctgc gcatctacct gatcgccaaa      600
cgcagcaacc gcagaggtcc cagggccaag ggggggcctg gcagggtga gtccaagcag       660 ccccgacccg accatggtgg ggctttggcc tcagccaaac tgccagccct ggcctctgtg      720
gcttctgcca gagaggtcaa cggacactcg aagtccactg gggagaagga ggaggggggag    780 accccctgaag atactgggac ccgggccttg ccacccagtt gggctgccct tcccaactca    840
ggccagggcc agaaggaggg tgtttgtggg gcatctccag aggatgaagc tgaagaggag      900
gaagaggagg aggaggagga ggaagagtgt gaaccccagg cagtgccagt gtctccggcc     960
tcagcttgca gcccccgct gcagcagcca cagggctccc gggtgctggc caccctacgt     1020
ggccaggtgc tcctgggcag gggcgtgggt gctataggtg ggcagtggtg gcgtcgaagg    1080
gcgcagctga cccgggagaa gcgcttcacc ttcgtgctgg ctgtggtcat tggcgttttt    1140
gtgctctgct ggttcccctt cttcttcagc tacagcctgg gcgccatctg cccgaagcac    1200
tgcaaggtgc cccatggcct cttccagttc ttcttctgga tcggctactg caacagctca    1260
ctgaaccctg ttatctacac catcttcaac caggacttcc gccgtgcctt ccggaggatc    1320
ctgtgccgcc cgtggaccca gacggcctgg tga                                  1353
```

<210> SEQ ID NO 2
<211> LENGTH: 1344
<212> TYPE: DNA
<213> ORGANISM: Homo sapiens

<400> SEQUENCE: 2

```
atggaccacc aggaccccta ctccgtgcag gccacagcgg ccatagcggc ggccatcacc       60
ttcctcattc tctttaccat cttcggcaac gctctggtca tcctggctgt gttgaccagc      120
cgctcgctgc gcgcccctca gaacctgttc ctggtgtcgc tggccgccgc cgacatcctg      180
gtggccacgc tcatcatccc tttctcgctg ccaacgagc tgctgggcta ctggtacttc      240
cggcgcacgt ggtgcgaggt gtacctggcg ctcgacgtgc tcttctgcac ctcgtccatc      300
gtgcacctgt gcgccatcag cctggaccgc tactgggccg tgagccgcgc gctggagtac     360
aactccaagc gcaccccgcg ccgcatcaag tgcatcatcc tcactgtgtg gctcatcgcc     420
gccgtcatct cgctgccgcc cctcatctac aagggcgacc agggccccca gccgcgcggg     480
cgcccccagt gcaagctcaa ccaggaggcc tggtacatcc tggcctccag catcggatct     540
ttctttgctc cttgcctcat catgatcctt gtctacctgc gcatctacct gatcgccaaa     600
cgcagcaacc gcagaggtcc cagggccaag ggggggcctg gcagggtga gtccaagcag      660 ccccgacccg accatggtgg ggctttggcc tcagccaaac tgccagccct ggcctctgtg     720
gcttctgcca gagaggtcaa cggacactcg aagtccactg gggagaagga ggaggggggag   780 accccctgaag atactgggac ccgggccttg ccacccagtt gggctgccct tcccaactca   840
ggccagggcc agaaggaggg tgtttgtggg gcatctccag aggatgaagc tgaagaggag     900
gaggaggagg aagagtg tgaaccccag gcagtgccag tgtctccggc tcagcttgc         960 agccccccgc tgcagcagcc acagggctcc cgggtgctgg ccacctacg tggccaggtg    1020 ctcctgggca ggggcgtggg tgctataggt gggcagtggt ggcgtcgaag ggcgcagctg    1080
acccgggaga agcgcttcac cttcgtgctg gctgtggtca ttggcgtttt tgtgctctgc    1140
```

-continued

```
tggttcccct tcttcttcag ctacagcctg ggcgccatct gcccgaagca ctgcaaggtg      1200
ccccatggcc tcttccagtt cttcttctgg atcggctact gcaacagctc actgaaccct      1260
gttatctaca ccatcttcaa ccaggacttc cgccgtgcct tccggaggat cctgtgccgc      1320
ccgtggaccc agacggcctg gtga                                             1344
```

<210> SEQ ID NO 3
<211> LENGTH: 9
<212> TYPE: DNA
<213> ORGANISM: Homo sapiens

<400> SEQUENCE: 3 gaagaggag                                                                      9

<210> SEQ ID NO 4
<211> LENGTH: 9
<212> TYPE: DNA
<213> ORGANISM: Homo sapiens

<400> SEQUENCE: 4 gaggaggag                                                                      9

<210> SEQ ID NO 5
<211> LENGTH: 9
<212> TYPE: DNA
<213> ORGANISM: Homo sapiens

<400> SEQUENCE: 5 cttctcctc                                                                      9

<210> SEQ ID NO 6
<211> LENGTH: 9
<212> TYPE: DNA
<213> ORGANISM: Homo sapiens

<400> SEQUENCE: 6 ctcctcctc                                                                      9

<210> SEQ ID NO 7
<211> LENGTH: 450
<212> TYPE: PRT
<213> ORGANISM: Homo sapiens

<400> SEQUENCE: 7

```
Met Asp His Gln Asp Pro Tyr Ser Val Gln Ala Thr Ala Ala Ile Ala
1               5                   10                  15

Ala Ala Ile Thr Phe Leu Ile Leu Phe Thr Ile Phe Gly Asn Ala Leu
            20                  25                  30

Val Ile Leu Ala Val Leu Thr Ser Arg Ser Leu Arg Ala Pro Gln Asn
        35                  40                  45

Leu Phe Leu Val Ser Leu Ala Ala Asp Ile Leu Val Ala Thr Leu
    50                  55                  60

Ile Ile Pro Phe Ser Leu Ala Asn Glu Leu Leu Gly Tyr Trp Tyr Phe
65                  70                  75                  80

Arg Arg Thr Trp Cys Glu Val Tyr Leu Ala Leu Asp Val Leu Phe Cys
                85                  90                  95

Thr Ser Ser Ile Val His Leu Cys Ala Ile Ser Leu Asp Arg Tyr Trp
            100                 105                 110

Ala Val Ser Arg Ala Leu Glu Tyr Asn Ser Lys Arg Thr Pro Arg Arg
```

-continued

```
                 115                 120                 125
Ile Lys Cys Ile Ile Leu Thr Val Trp Leu Ile Ala Ala Val Ile Ser
        130                 135                 140

Leu Pro Pro Leu Ile Tyr Lys Gly Asp Gln Gly Pro Gln Pro Arg Gly
145                 150                 155                 160

Arg Pro Gln Cys Lys Leu Asn Gln Glu Ala Trp Tyr Ile Leu Ala Ser
                165                 170                 175

Ser Ile Gly Ser Phe Phe Ala Pro Cys Leu Ile Met Ile Leu Val Tyr
                180                 185                 190

Leu Arg Ile Tyr Leu Ile Ala Lys Arg Ser Asn Arg Arg Gly Pro Arg
            195                 200                 205

Ala Lys Gly Gly Pro Gly Gln Gly Glu Ser Lys Gln Pro Arg Pro Asp
    210                 215                 220

His Gly Gly Ala Leu Ala Ser Ala Lys Leu Pro Ala Leu Ala Ser Val
225                 230                 235                 240

Ala Ser Ala Arg Glu Val Asn Gly His Ser Lys Ser Thr Gly Glu Lys
                245                 250                 255

Glu Glu Gly Glu Thr Pro Glu Asp Thr Gly Thr Arg Ala Leu Pro Pro
            260                 265                 270

Ser Trp Ala Ala Leu Pro Asn Ser Gly Gln Gly Gln Lys Glu Gly Val
    275                 280                 285

Cys Gly Ala Ser Pro Glu Asp Glu Ala Glu Glu Glu Glu Glu Glu Glu
    290                 295                 300

Glu Glu Glu Glu Glu Cys Glu Pro Gln Ala Val Pro Val Ser Pro Ala
305                 310                 315                 320

Ser Ala Cys Ser Pro Pro Leu Gln Gln Pro Gln Gly Ser Arg Val Leu
                325                 330                 335

Ala Thr Leu Arg Gly Gln Val Leu Leu Gly Arg Gly Val Gly Ala Ile
            340                 345                 350

Gly Gly Gln Trp Trp Arg Arg Arg Ala Gln Leu Thr Arg Glu Lys Arg
        355                 360                 365

Phe Thr Phe Val Leu Ala Val Val Ile Gly Val Phe Val Leu Cys Trp
370                 375                 380

Phe Pro Phe Phe Phe Ser Tyr Ser Leu Gly Ala Ile Cys Pro Lys His
385                 390                 395                 400

Cys Lys Val Pro His Gly Leu Phe Gln Phe Phe Phe Trp Ile Gly Tyr
                405                 410                 415

Cys Asn Ser Ser Leu Asn Pro Val Ile Tyr Thr Ile Phe Asn Gln Asp
            420                 425                 430

Phe Arg Arg Ala Phe Arg Arg Ile Leu Cys Arg Pro Trp Thr Gln Thr
        435                 440                 445
Ala Trp
    450
```

<210> SEQ ID NO 8
<211> LENGTH: 447
<212> TYPE: PRT
<213> ORGANISM: Homo sapiens

<400> SEQUENCE: 8

```
Met Asp His Gln Asp Pro Tyr Ser Val Gln Ala Thr Ala Ala Ile Ala
1               5                   10                  15

Ala Ala Ile Thr Phe Leu Ile Leu Phe Thr Ile Phe Gly Asn Ala Leu
            20                  25                  30

Val Ile Leu Ala Val Leu Thr Ser Arg Ser Leu Arg Ala Pro Gln Asn
```

```
                35                  40                  45
Leu Phe Leu Val Ser Leu Ala Ala Asp Ile Leu Val Ala Thr Leu
 50                  55                  60
Ile Ile Pro Phe Ser Leu Ala Asn Glu Leu Leu Gly Tyr Trp Tyr Phe
 65                      70                  75                  80
Arg Arg Thr Trp Cys Glu Val Tyr Leu Ala Leu Asp Val Leu Phe Cys
                 85                  90                  95
Thr Ser Ser Ile Val His Leu Cys Ala Ile Ser Leu Asp Arg Tyr Trp
                100                 105                 110
Ala Val Ser Arg Ala Leu Glu Tyr Asn Ser Lys Arg Thr Pro Arg Arg
                115                 120                 125
Ile Lys Cys Ile Ile Leu Thr Val Trp Leu Ile Ala Ala Val Ile Ser
130                 135                 140
Leu Pro Pro Leu Ile Tyr Lys Gly Asp Gln Gly Pro Gln Pro Arg Gly
145                 150                 155                 160
Arg Pro Gln Cys Lys Leu Asn Gln Glu Ala Trp Tyr Ile Leu Ala Ser
                165                 170                 175
Ser Ile Gly Ser Phe Phe Ala Pro Cys Leu Ile Met Ile Leu Val Tyr
                180                 185                 190
Leu Arg Ile Tyr Leu Ile Ala Lys Arg Ser Asn Arg Arg Gly Pro Arg
                195                 200                 205
Ala Lys Gly Gly Pro Gly Gln Gly Glu Ser Lys Gln Pro Arg Pro Asp
210                 215                 220
His Gly Gly Ala Leu Ala Ser Ala Lys Leu Pro Ala Leu Ala Ser Val
225                 230                 235                 240
Ala Ser Ala Arg Glu Val Asn Gly His Ser Lys Ser Thr Gly Glu Lys
                245                 250                 255
Glu Glu Gly Glu Thr Pro Glu Asp Thr Gly Thr Arg Ala Leu Pro Pro
                260                 265                 270
Ser Trp Ala Ala Leu Pro Asn Ser Gly Gln Gly Gln Lys Glu Gly Val
                275                 280                 285
Cys Gly Ala Ser Pro Glu Asp Glu Ala Glu Glu Glu Glu Glu Glu Glu
290                 295                 300
Glu Glu Cys Glu Pro Gln Ala Val Pro Val Ser Pro Ala Ser Ala Cys
305                 310                 315                 320
Ser Pro Pro Leu Gln Gln Pro Gln Gly Ser Arg Val Leu Ala Thr Leu
                325                 330                 335
Arg Gly Gln Val Leu Leu Gly Arg Gly Val Gly Ala Ile Gly Gly Gln
                340                 345                 350
Trp Trp Arg Arg Arg Ala Gln Leu Thr Arg Glu Lys Arg Phe Thr Phe
                355                 360                 365
Val Leu Ala Val Val Ile Gly Val Phe Val Leu Cys Trp Phe Pro Phe
370                 375                 380
Phe Phe Ser Tyr Ser Leu Gly Ala Ile Cys Pro Lys His Cys Lys Val
385                 390                 395                 400
Pro His Gly Leu Phe Gln Phe Phe Phe Trp Ile Gly Tyr Cys Asn Ser
                405                 410                 415
Ser Leu Asn Pro Val Ile Tyr Thr Ile Phe Asn Gln Asp Phe Arg Arg
                420                 425                 430
Ala Phe Arg Arg Ile Leu Cys Arg Pro Trp Thr Gln Thr Ala Trp
                435                 440                 445

<210> SEQ ID NO 9
```

-continued

```
<211> LENGTH: 16
<212> TYPE: PRT
<213> ORGANISM: Homo sapiens

<400> SEQUENCE: 9

Glu Asp Glu Ala Glu Glu Glu Glu Glu Glu Glu Glu Glu Glu Glu Glu
1               5                   10                  15

<210> SEQ ID NO 10
<211> LENGTH: 13
<212> TYPE: PRT
<213> ORGANISM: Homo sapiens

<400> SEQUENCE: 10

Glu Asp Glu Ala Glu Glu Glu Glu Glu Glu Glu Glu Glu
1               5                   10

<210> SEQ ID NO 11
<211> LENGTH: 3
<212> TYPE: PRT
<213> ORGANISM: Homo sapiens

<400> SEQUENCE: 11

Glu Glu Glu
1

<210> SEQ ID NO 12
<211> LENGTH: 3
<212> TYPE: PRT
<213> ORGANISM: Homo sapiens

<400> SEQUENCE: 12

Cys Glu Pro
1

<210> SEQ ID NO 13
<211> LENGTH: 21
<212> TYPE: DNA
<213> ORGANISM: Homo sapiens

<400> SEQUENCE: 13
gctcatcatc cctttctcgc t                                         21

<210> SEQ ID NO 14
<211> LENGTH: 21
<212> TYPE: DNA
<213> ORGANISM: Homo sapiens

<400> SEQUENCE: 14
aaagccccac catggtcggg t                                         21

<210> SEQ ID NO 15
<211> LENGTH: 20
<212> TYPE: DNA
<213> ORGANISM: Homo sapiens

<400> SEQUENCE: 15
ctgatcgcca aacgagcaac                                           20

<210> SEQ ID NO 16
<211> LENGTH: 20
<212> TYPE: DNA
<213> ORGANISM: Homo sapiens

<400> SEQUENCE: 16
```
aaaaacgcca atgaccacag                                                     20

<210> SEQ ID NO 17
<211> LENGTH: 18
<212> TYPE: DNA
<213> ORGANISM: Homo sapiens

<400> SEQUENCE: 17
tgtaaaacga cggccagt                                                       18

<210> SEQ ID NO 18
<211> LENGTH: 18
<212> TYPE: DNA
<213> ORGANISM: Homo sapiens

<400> SEQUENCE: 18
caggaaacag ctatgacc                                                       18

<210> SEQ ID NO 19
<211> LENGTH: 21
<212> TYPE: DNA
<213> ORGANISM: Homo sapiens

<400> SEQUENCE: 19
agaaggaggg tgtttgtggg g                                                   21

<210> SEQ ID NO 20
<211> LENGTH: 21
<212> TYPE: DNA
<213> ORGANISM: Homo sapiens

<400> SEQUENCE: 20
acctatagca cccacgcccc t                                                   21

<210> SEQ ID NO 21
<211> LENGTH: 21
<212> TYPE: DNA
<213> ORGANISM: Homo sapiens

<400> SEQUENCE: 21
ggccgacgct cttgtctagc c                                                   21

<210> SEQ ID NO 22
<211> LENGTH: 20
<212> TYPE: DNA
<213> ORGANISM: Homo sapiens

<400> SEQUENCE: 22 caagggttc ctaagatgag                                                      20

<210> SEQ ID NO 23
<211> LENGTH: 9
<212> TYPE: PRT
<213> ORGANISM: Homo sapiens

<400> SEQUENCE: 23

Tyr Pro Tyr Asp Val Pro Asp Tyr Ala
1               5

<210> SEQ ID NO 24
<211> LENGTH: 1350
<212> TYPE: DNA
<213> ORGANISM: Homo sapiens

<400> SEQUENCE: 24

| | |
|---|---|
| atgggctccc tgcagccgga cgcgggcaac gcgagctgga acgggaccga ggcgccgggg | 60 |
| ggcggcgccc gggccacccc ttactccctg caggtgacgc tgacgctggt gtgcctggcc | 120 |
| ggcctgctca tgctgctcac cgtgttcggc aacgtgctcg tcatcatcgc cgtgttcacg | 180 |
| agccgcgcgc tcaaggcgcc ccaaaacctc ttcctggtgt ctctggcctc ggccgacatc | 240 |
| ctggtggcca cgctcgtcat cccttctcg ctggccaacg aggtcatggg ctactggtac | 300 |
| ttcggcaagg cttggtgcga gatctacctg gcgctcgacg tgctcttctg cacgtcgtcc | 360 |
| atcgtgcacc tgtgcgccat cagcctggac cgctactggt ccatcacaca ggccatcgag | 420 |
| tacaacctga gcgcacgcc gcgccgcatc aaggccatca tcatcaccgt gtgggtcatc | 480 |
| tcggccgtca tctccttccc gccgctcatc tccatcgaga agaagggcgg cggcggcggc | 540 |
| ccgcagccgg ccgagccgcg ctgcgagatc aacgaccaga agtggtacgt catctcgtcg | 600 |
| tgcatcggct ccttcttcgc tccctgcctc atcatgatcc tggtctacgt gcgcatctac | 660 |
| cagatcgcca agcgtcgcac ccgcgtgcca cccagccgcc gggtccgga cgccgtcgcc | 720 |
| gcgccgccgg ggggcaccga gcgcaggccc aacggtctgg gccccgagcg cagcgcgggc | 780 |
| ccggggggcg cagaggccga accgctgccc acccagctca acggcgcccc tggcgagccc | 840 |
| gcgccggccg ggccgcgcga caccgacgcg ctggacctgg aggagagctc gtcttccgac | 900 |
| cacgccgagc ggcctccagg gccccgcaga cccgagcgcg gtccccgggg caaaggcaag | 960 |
| gcccgagcga gccaggtgaa gccgggcgac agcctgccgc ggcgcgggcc gggggcgacg | 1020 |
| gggatcggga cgccggctgc agggccgggg gaggagcgcg tcggggctgc caaggcgtcg | 1080 |
| cgctggcgcg ggcggcagaa ccgcgagaag cgcttcacgt tcgtgctggc cgtggtcatc | 1140 |
| ggagtgttcg tggtgtgctg gttcccttc ttcttcacct acacgctcac ggccgtcggg | 1200 |
| tgctccgtgc cacgcacgct cttcaaattc ttcttctggt tcggctactg caacagctcg | 1260 |
| ttgaacccgg tcatctacac catcttcaac cacgatttcc gccgcgcctt caagaagatc | 1320 |
| ctctgtcggg gggacaggaa gcggatcgtg | 1350 |

<210> SEQ ID NO 25
<211> LENGTH: 1350
<212> TYPE: DNA
<213> ORGANISM: Homo sapiens

<400> SEQUENCE: 25

| | |
|---|---|
| atgggctccc tgcagccgga cgcgggcaac gcgagctgga acgggaccga ggcgccgggg | 60 |
| ggcggcgccc gggccacccc ttactccctg caggtgacgc tgacgctggt gtgcctggcc | 120 |
| ggcctgctca tgctgctcac cgtgttcggc aacgtgctcg tcatcatcgc cgtgttcacg | 180 |
| agccgcgcgc tcaaggcgcc ccaaaacctc ttcctggtgt ctctggcctc ggccgacatc | 240 |
| ctggtggcca cgctcgtcat cccttctcg ctggccaacg aggtcatggg ctactggtac | 300 |
| ttcggcaagg cttggtgcga gatctacctg gcgctcgacg tgctcttctg cacgtcgtcc | 360 |
| atcgtgcacc tgtgcgccat cagcctggac cgctactggt ccatcacaca ggccatcgag | 420 |
| tacaacctga gcgcacgcc gcgccgcatc aaggccatca tcatcaccgt gtgggtcatc | 480 |
| tcggccgtca tctccttccc gccgctcatc tccatcgaga agaagggcgg cggcggcggc | 540 |
| ccgcagccgg ccgagccgcg ctgcgagatc aacgaccaga agtggtacgt catctcgtcg | 600 |
| tgcatcggct ccttcttcgc tccctgcctc atcatgatcc tggtctacgt gcgcatctac | 660 |

```
cagatcgcca agcgtcgcac ccgcgtgcca cccagccgcc ggggtccgga cgccgtcgcc    720
gcgccgccgg ggggcaccga gcgcaggccc aagggtctgg gccccgagcg cagcgcgggc    780
ccggggggcg cagaggccga accgctgccc acccagctca acggcgcccc tgcgagccc     840 gcgccggccg ggccgcgcga caccgacgcg ctggacctgg aggagagctc gtcttccgac    900
cacgccgagc ggcctccagg gccccgcaga cccgagcgcg gtccccgggg caaaggcaag    960
gcccgagcga gccaggtgaa gccgggcgac agcctgccgc ggcgcgggcc ggggcgacg    1020 gggatcggga cgccggctgc agggccgggg gaggagcgcg tcgggctgc caaggcgtcg    1080 cgctggcgcg ggcggcagaa ccgcgagaag cgcttcacgt tcgtgctggc cgtggtcatc    1140
ggagtgttcg tggtgtgctg gttccccttc ttcttcacct acacgctcac ggccgtcggg    1200
tgctccgtgc cacgcacgct cttcaaattc ttcttctggt tcggctactg caacagctcg    1260
ttgaacccgg tcatctacac catcttcaac cacgatttcc gccgcgcctt caagaagatc    1320
ctctgtcggg gggacaggaa gcggatcgtg                                     1350
```

<210> SEQ ID NO 26
<211> LENGTH: 450
<212> TYPE: PRT
<213> ORGANISM: Homo sapiens

<400> SEQUENCE: 26

```
Met Gly Ser Leu Gln Pro Asp Ala Gly Asn Ala Ser Trp Asn Gly Thr
 1               5                  10                  15

Glu Ala Pro Gly Gly Gly Ala Arg Ala Thr Pro Tyr Ser Leu Gln Val
             20                  25                  30

Thr Leu Thr Leu Val Cys Leu Ala Gly Leu Leu Met Leu Leu Thr Val
         35                  40                  45

Phe Gly Asn Val Leu Val Ile Ile Ala Val Phe Thr Ser Arg Ala Leu
     50                  55                  60

Lys Ala Pro Gln Asn Leu Phe Leu Val Ser Leu Ala Ser Ala Asp Ile
 65                  70                  75                  80

Leu Val Ala Thr Leu Val Ile Pro Phe Ser Leu Ala Asn Glu Val Met
                 85                  90                  95

Gly Tyr Trp Tyr Phe Gly Lys Ala Trp Cys Glu Ile Tyr Leu Ala Leu
            100                 105                 110

Asp Val Leu Phe Cys Thr Ser Ser Ile Val His Leu Cys Ala Ile Ser
        115                 120                 125

Leu Asp Arg Tyr Trp Ser Ile Thr Gln Ala Ile Glu Tyr Asn Leu Lys
    130                 135                 140

Arg Thr Pro Arg Arg Ile Lys Ala Ile Ile Thr Val Trp Val Ile
145                 150                 155                 160

Ser Ala Val Ile Ser Phe Pro Pro Leu Ile Ser Ile Glu Lys Lys Gly
                165                 170                 175

Gly Gly Gly Gly Pro Gln Pro Ala Glu Pro Arg Cys Glu Ile Asn Asp
            180                 185                 190

Gln Lys Trp Tyr Val Ile Ser Ser Cys Ile Gly Ser Phe Phe Ala Pro
        195                 200                 205

Cys Leu Ile Met Ile Leu Val Tyr Val Arg Ile Tyr Gln Ile Ala Lys
    210                 215                 220

Arg Arg Thr Arg Val Pro Pro Ser Arg Arg Gly Pro Asp Ala Val Ala
225                 230                 235                 240

Ala Pro Pro Gly Gly Thr Glu Arg Arg Pro Asn Gly Leu Gly Pro Glu
                245                 250                 255
```

-continued

```
Arg Ser Ala Gly Pro Gly Gly Ala Glu Ala Glu Pro Leu Pro Thr Gln
            260                 265                 270

Leu Asn Gly Ala Pro Gly Glu Pro Ala Pro Ala Gly Pro Arg Asp Thr
            275                 280                 285

Asp Ala Leu Asp Leu Glu Glu Ser Ser Ser Asp His Ala Glu Arg
290                 295                 300

Pro Pro Gly Pro Arg Arg Pro Glu Arg Gly Pro Arg Gly Lys Gly Lys
305                 310                 315                 320

Ala Arg Ala Ser Gln Val Lys Pro Gly Asp Ser Leu Pro Arg Arg Gly
            325                 330                 335

Pro Gly Ala Thr Gly Ile Gly Thr Pro Ala Ala Gly Pro Gly Glu Glu
            340                 345                 350

Arg Val Gly Ala Ala Lys Ala Ser Arg Trp Arg Gly Arg Gln Asn Arg
            355                 360                 365

Glu Lys Arg Phe Thr Phe Val Leu Ala Val Val Ile Gly Val Phe Val
            370                 375                 380

Val Cys Trp Phe Pro Phe Phe Thr Tyr Thr Leu Thr Ala Val Gly
385                 390                 395                 400

Cys Ser Val Pro Arg Thr Leu Phe Lys Phe Phe Trp Phe Gly Tyr
            405                 410                 415

Cys Asn Ser Ser Leu Asn Pro Val Ile Tyr Thr Ile Phe Asn His Asp
            420                 425                 430

Phe Arg Arg Ala Phe Lys Lys Ile Leu Cys Arg Gly Asp Arg Lys Arg
            435                 440                 445

Ile Val
450

<210> SEQ ID NO 27
<211> LENGTH: 450
<212> TYPE: PRT
<213> ORGANISM: Homo sapiens

<400> SEQUENCE: 27

Met Gly Ser Leu Gln Pro Asp Ala Gly Asn Ala Ser Trp Asn Gly Thr
1               5                   10                  15

Glu Ala Pro Gly Gly Gly Ala Arg Ala Thr Pro Tyr Ser Leu Gln Val
            20                  25                  30

Thr Leu Thr Leu Val Cys Leu Ala Gly Leu Leu Met Leu Leu Thr Val
            35                  40                  45

Phe Gly Asn Val Leu Val Ile Ile Ala Val Phe Thr Ser Arg Ala Leu
50                  55                  60

Lys Ala Pro Gln Asn Leu Phe Leu Val Ser Leu Ala Ser Ala Asp Ile
65                  70                  75                  80

Leu Val Ala Thr Leu Val Ile Pro Phe Ser Leu Ala Asn Glu Val Met
            85                  90                  95

Gly Tyr Trp Tyr Phe Gly Lys Ala Trp Cys Glu Ile Tyr Leu Ala Leu
            100                 105                 110

Asp Val Leu Phe Cys Thr Ser Ser Ile Val His Leu Cys Ala Ile Ser
            115                 120                 125

Leu Asp Arg Tyr Trp Ser Ile Thr Gln Ala Ile Glu Tyr Asn Leu Lys
            130                 135                 140

Arg Thr Pro Arg Arg Ile Lys Ala Ile Ile Thr Val Trp Val Ile
145                 150                 155                 160

Ser Ala Val Ile Ser Phe Pro Pro Leu Ile Ser Ile Glu Lys Lys Gly
```

```
              165                 170                 175
Gly Gly Gly Gly Pro Gln Pro Ala Glu Pro Arg Cys Glu Ile Asn Asp
            180                 185                 190
Gln Lys Trp Tyr Val Ile Ser Ser Cys Ile Gly Ser Phe Phe Ala Pro
        195                 200                 205
Cys Leu Ile Met Ile Leu Val Tyr Val Arg Ile Tyr Gln Ile Ala Lys
    210                 215                 220
Arg Arg Thr Arg Val Pro Ser Arg Arg Gly Pro Asp Ala Val Ala
225                 230                 235                 240
Ala Pro Pro Gly Gly Thr Glu Arg Arg Pro Lys Gly Leu Gly Pro Glu
                245                 250                 255
Arg Ser Ala Gly Pro Gly Gly Ala Glu Ala Glu Pro Leu Pro Thr Gln
            260                 265                 270
Leu Asn Gly Ala Pro Gly Glu Pro Ala Pro Ala Gly Pro Arg Asp Thr
        275                 280                 285
Asp Ala Leu Asp Leu Glu Ser Ser Ser Asp His Ala Glu Arg
    290                 295                 300
Pro Pro Gly Pro Arg Arg Pro Glu Arg Gly Pro Arg Gly Lys Gly Lys
305                 310                 315                 320
Ala Arg Ala Ser Gln Val Lys Pro Gly Asp Ser Leu Pro Arg Arg Gly
                325                 330                 335
Pro Gly Ala Thr Gly Ile Gly Thr Pro Ala Ala Gly Pro Gly Glu Glu
            340                 345                 350
Arg Val Gly Ala Ala Lys Ala Ser Arg Trp Arg Gly Arg Gln Asn Arg
        355                 360                 365
Glu Lys Arg Phe Thr Phe Val Leu Ala Val Val Ile Gly Val Phe Val
    370                 375                 380
Val Cys Trp Phe Pro Phe Phe Phe Thr Tyr Thr Leu Thr Ala Val Gly
385                 390                 395                 400
Cys Ser Val Pro Arg Thr Leu Phe Lys Phe Phe Phe Trp Phe Gly Tyr
                405                 410                 415
Cys Asn Ser Ser Leu Asn Pro Val Ile Tyr Thr Ile Phe Asn His Asp
            420                 425                 430
Phe Arg Arg Ala Phe Lys Lys Ile Leu Cys Arg Gly Asp Arg Lys Arg
        435                 440                 445
Ile Val
    450

<210> SEQ ID NO 28
<211> LENGTH: 22
<212> TYPE: DNA
<213> ORGANISM: Homo sapiens

<400> SEQUENCE: 28
tttacccatc ggctctccct ac                                          22

<210> SEQ ID NO 29
<211> LENGTH: 23
<212> TYPE: DNA
<213> ORGANISM: Homo sapiens

<400> SEQUENCE: 29
gagacaccag gaagaggttt tgg                                         23

<210> SEQ ID NO 30
<211> LENGTH: 20
```

```
<212> TYPE: DNA
<213> ORGANISM: Homo sapiens

<400> SEQUENCE: 30
tcgtcatcat cgccgtgttc                                             20

<210> SEQ ID NO 31
<211> LENGTH: 23
<212> TYPE: DNA
<213> ORGANISM: Homo sapiens

<400> SEQUENCE: 31
cgtaccactt ctggtcgttg atc                                         23

<210> SEQ ID NO 32
<211> LENGTH: 24
<212> TYPE: DNA
<213> ORGANISM: Homo sapiens

<400> SEQUENCE: 32
gccatcatca tcaccgtgtg ggtc                                        24

<210> SEQ ID NO 33
<211> LENGTH: 23
<212> TYPE: DNA
<213> ORGANISM: Homo sapiens

<400> SEQUENCE: 33
ggctcgctcg ggccttgcct ttg                                         23

<210> SEQ ID NO 34
<211> LENGTH: 22
<212> TYPE: DNA
<213> ORGANISM: Homo sapiens

<400> SEQUENCE: 34
gacctggagg agagctcgtc tt                                          22

<210> SEQ ID NO 35
<211> LENGTH: 23
<212> TYPE: DNA
<213> ORGANISM: Homo sapiens

<400> SEQUENCE: 35
tgaccgggtt caacgagctg ttg                                         23

<210> SEQ ID NO 36
<211> LENGTH: 23
<212> TYPE: DNA
<213> ORGANISM: Homo sapiens

<400> SEQUENCE: 36
gccacgcacg ctcttcaaat tct                                         23

<210> SEQ ID NO 37
<211> LENGTH: 22
<212> TYPE: DNA
<213> ORGANISM: Homo sapiens

<400> SEQUENCE: 37
ttcccttgta ggagcagcag ac                                          22

<210> SEQ ID NO 38
```

<211> LENGTH: 18
<212> TYPE: DNA
<213> ORGANISM: Homo sapiens

<400> SEQUENCE: 38
tgtaaaacga cggccagt                                                 18

<210> SEQ ID NO 39
<211> LENGTH: 18
<212> TYPE: DNA
<213> ORGANISM: Homo sapiens

<400> SEQUENCE: 39
caggaaacag ctatgacc                                                 18

<210> SEQ ID NO 40
<211> LENGTH: 1386
<212> TYPE: DNA
<213> ORGANISM: Homo sapiens

<400> SEQUENCE: 40

```
atggcgtccc cggcgctggc ggcggcgctg gcggtggcgg cagcggcggg ccccaatgcg     60
agcggcgcgg gcgagagggg cagcggcggg gttgccaatg cctcgggggc ttcctggggg    120
ccgccgcgcg gccagtactc ggcgggcgcg gtggcagggc tggctgccgt ggtgggcttc    180
ctcatcgtct tcaccgtggt gggcaacgtg ctggtggtga tcgccgtgct gaccagccgg    240
gcgctgcgcg cgccacagaa cctcttcctg gtgtcgctgg cctcggccga catcctggtg    300
gccacgctgg tcatgccctt ctcgttggcc aacgagctca tggcctactg gtacttcggg    360
caggtgtggt gcggcgtgta cctggcgctc gatgtgctgt tttgcacctc gtcgatcgtg    420
catctgtgtg ccatcagcct ggaccgctac tggtcggtga cgcaggccgt cgagtacaac    480
ctgaagcgca caccacgccg cgtcaaggcc accatcgtcg ccgtgtggct catctcggcc    540
gtcatctcct tcccgccgct ggtctcgctc taccgccagc ccgacggcgc cgcctacccg    600
cagtgcggcc tcaacgacga gacctggtac atcctgtcct cctgcatcgg ctccttcttc    660
gcgccctgcc tcatcatggg cctggtctac gcgcgcatct accgagtggc caagcgtcgc    720
acgcgcacgc tcagcgagaa gcgcgccccc gtgggcccca cggtgcgtc cccgactacc    780
gaaaacgggc tgggcgcggc ggcaggcgca ggcgagaacg ggcactgcgc gccccgccc    840
gccgacgtgg agccgacga gagcagcgca gcggccgaga ggcggcgcg ccggggcgcg    900
ttgcggcggg gcgggcggcg gcgagcgggc gcggagggg gcgcgggcgg tgcggacggg    960
caggggcgg ggccggggc ggctgagtcg ggggcgctga ccgcctccag gtccccgggg   1020
cccggtggcc gcctctcgcg cgccagctcg cgctccgtcg agttcttcct gtcgcgccgg   1080
cgccgggcgc gcagcagcgt gtgccgccgc aaggtggccc aggcgcgcga gaagcgcttc   1140
acctttgtgc tggctgtggt catgggcgtg ttcgtgctct gctggttccc cttcttcttc   1200
atctacagcc tgtacggcat ctgccgcgag gcctgccagg tgcccggccc gctcttcaag   1260
ttcttcttct ggatcggcta ctgcaacagc tcgctcaacc cggtcatcta cacggtcttc   1320
aaccaggatt tccggccatc cttcaagcac atcctcttcc gacggaggag aaggggcttc   1380
aggcag                                                             1386
```

<210> SEQ ID NO 41
<211> LENGTH: 12
<212> TYPE: DNA
<213> ORGANISM: Homo sapiens

<400> SEQUENCE: 41
ggggcggggc cg                                                    12

<210> SEQ ID NO 42
<211> LENGTH: 1374
<212> TYPE: DNA
<213> ORGANISM: Homo sapiens

<400> SEQUENCE: 42
atggcgtccc cggcgctggc ggcggcgctg gcggtggcgg cagcggcggg ccccaatgcg      60
agcggcgcgg gcgagagggg cagcggcggg gttgccaatg cctcggggc ttcctggggg     120
ccgccgcgcg gccagtactc ggcgggcgcg gtggcagggc tggctgccgt ggtgggcttc     180
ctcatcgtct tcaccgtggt gggcaacgtg ctggtggtga tcgccgtgct gaccagccgg     240
gcgctgcgcg cgccacagaa cctcttcctg gtgtcgctgg cctcggccga catcctggtg     300
gccacgctgg tcatgcccct ttcgttggcc aacgagctca tggcctactg gtacttcggg     360
caggtgtggt gcggcgtgta cctggcgctc gatgtgctgt tttgcacctc gtcgatcgtg     420
catctgtgtg ccatcagcct ggaccgctac tggtcggtga cgcaggccgt cgagtacaac     480
ctgaagcgca caccacgccg cgtcaaggcc accatcgtcg ccgtgtggct catctcggcc     540
gtcatctcct tcccgccgct ggtctcgctc taccgccagc cgacggcgc cgcctacccg     600
cagtgcggcc tcaacgacga gacctggtac atcctgtcct cctgcatcgg ctccttcttc     660
gcgccctgcc tcatcatggg cctggtctac gcgcgcatct accagtggc caagcgtcgc     720
acgcgcacgc tcagcgagaa gcgcgccccc gtgggccccg acggtgcgtc cccgactacc     780
gaaaacgggc tggcgcggc ggcaggcgca ggcgagaacg gcactgcgc gcccccgccc     840
gccgacgtgg agccggacga gagcagcgca gcggccgaga ggcggcggcg ccggggcgcg     900
ttgcggcggg cgggcggcg gcgagcgggc cggaggggg gcgcgggcgg tgcggacggg     960
caggggggcgg ctgagtcggg ggcgctgacc ggcctccaggt ccccggggcc cggtggccgc    1020
ctctcgcgcg ccagctcgcg ctccgtcgag ttcttcctgt cgcgccggcg ccgggcgcgc    1080
agcagcgtgt gccgccgcaa ggtggcccag gcgcgcgaga agcgcttcac ctttgtgctg    1140
gctgtggtca tggcgtgtt cgtgctctgc tggttcccct tcttcttcat ctacagcctg    1200
tacggcatct gccgcgaggc ctgccaggtg cccggcccgc tcttcaagtt cttcttctgg    1260
atcggctact gcaacagctc gctcaacccg gtcatctaca cggtcttcaa ccaggatttc    1320
cggccatcct tcaagcacat cctcttccga cggaggagaa ggggcttcag gcag          1374

<210> SEQ ID NO 43
<211> LENGTH: 12
<212> TYPE: DNA
<213> ORGANISM: Homo sapiens

<400> SEQUENCE: 43
ggggcggctg ag                                                    12

<210> SEQ ID NO 44
<211> LENGTH: 462
<212> TYPE: PRT
<213> ORGANISM: Homo sapiens

<400> SEQUENCE: 44

Met Ala Ser Pro Ala Leu Ala Ala Ala Leu Ala Val Ala Ala Ala Ala
1               5                   10                  15

-continued

```
Gly Pro Asn Ala Ser Gly Ala Gly Glu Arg Gly Ser Gly Gly Val Ala
            20                  25                  30

Asn Ala Ser Gly Ala Ser Trp Gly Pro Pro Arg Gly Gln Tyr Ser Ala
            35                  40                  45

Gly Ala Val Ala Gly Leu Ala Ala Val Val Gly Phe Leu Ile Val Phe
 50                  55                  60

Thr Val Val Gly Asn Val Leu Val Val Ile Ala Val Leu Thr Ser Arg
 65                  70                  75                  80

Ala Leu Arg Ala Pro Gln Asn Leu Phe Leu Val Ser Leu Ala Ser Ala
                85                  90                  95

Asp Ile Leu Val Ala Thr Leu Val Met Pro Phe Ser Leu Ala Asn Glu
            100                 105                 110

Leu Met Ala Tyr Trp Tyr Phe Gly Gln Val Trp Cys Gly Val Tyr Leu
            115                 120                 125

Ala Leu Asp Val Leu Phe Cys Thr Ser Ser Ile Val His Leu Cys Ala
130                 135                 140

Ile Ser Leu Asp Arg Tyr Trp Ser Val Thr Gln Ala Val Glu Tyr Asn
145                 150                 155                 160

Leu Lys Arg Thr Pro Arg Arg Val Lys Ala Thr Ile Val Ala Val Trp
                165                 170                 175

Leu Ile Ser Ala Val Ile Ser Phe Pro Pro Leu Val Ser Leu Tyr Arg
            180                 185                 190

Gln Pro Asp Gly Ala Ala Tyr Pro Gln Cys Gly Leu Asn Asp Glu Thr
            195                 200                 205

Trp Tyr Ile Leu Ser Ser Cys Ile Gly Ser Phe Phe Ala Pro Cys Leu
210                 215                 220

Ile Met Gly Leu Val Tyr Ala Arg Ile Tyr Arg Val Ala Lys Arg Arg
225                 230                 235                 240

Thr Arg Thr Leu Ser Glu Lys Arg Ala Pro Val Gly Pro Asp Gly Ala
                245                 250                 255

Ser Pro Thr Thr Glu Asn Gly Leu Gly Ala Ala Ala Gly Ala Gly Glu
            260                 265                 270

Asn Gly His Cys Ala Pro Pro Ala Asp Val Glu Pro Asp Glu Ser
            275                 280                 285

Ser Ala Ala Ala Glu Arg Arg Arg Arg Gly Ala Leu Arg Arg Gly
    290                 295                 300

Gly Arg Arg Arg Ala Gly Ala Glu Gly Gly Ala Gly Gly Ala Asp Gly
305                 310                 315                 320

Gln Gly Ala Gly Pro Gly Ala Ala Glu Ser Gly Ala Leu Thr Ala Ser
                325                 330                 335

Arg Ser Pro Gly Pro Gly Gly Arg Leu Ser Arg Ala Ser Ser Arg Ser
            340                 345                 350

Val Glu Phe Phe Leu Ser Arg Arg Arg Arg Ala Arg Ser Ser Val Cys
            355                 360                 365

Arg Arg Lys Val Ala Gln Ala Arg Glu Lys Arg Phe Thr Phe Val Leu
370                 375                 380

Ala Val Val Met Gly Val Phe Val Leu Cys Trp Phe Pro Phe Phe Phe
385                 390                 395                 400

Ile Tyr Ser Leu Tyr Gly Ile Cys Arg Glu Ala Cys Gln Val Pro Gly
                405                 410                 415

Pro Leu Phe Lys Phe Phe Phe Trp Ile Gly Tyr Cys Asn Ser Ser Leu
            420                 425                 430
```

```
Asn Pro Val Ile Tyr Thr Val Phe Asn Gln Asp Phe Arg Pro Ser Phe
            435                 440                 445

Lys His Ile Leu Phe Arg Arg Arg Arg Gly Phe Arg Gln
    450                 455                 460

<210> SEQ ID NO 45
<211> LENGTH: 4
<212> TYPE: PRT
<213> ORGANISM: Homo sapiens

<400> SEQUENCE: 45

Gly Ala Gly Pro
1

<210> SEQ ID NO 46
<211> LENGTH: 458
<212> TYPE: PRT
<213> ORGANISM: Homo sapiens

<400> SEQUENCE: 46

Met Ala Ser Pro Ala Leu Ala Ala Leu Ala Val Ala Ala Ala
1               5                   10                  15

Gly Pro Asn Ala Ser Gly Ala Gly Glu Arg Gly Ser Gly Gly Val Ala
                20                  25                  30

Asn Ala Ser Gly Ala Ser Trp Gly Pro Pro Arg Gly Gln Tyr Ser Ala
            35                  40                  45

Gly Ala Val Ala Gly Leu Ala Ala Val Val Gly Phe Leu Ile Val Phe
        50                  55                  60

Thr Val Val Gly Asn Val Leu Val Val Ile Ala Val Leu Thr Ser Arg
65                  70                  75                  80

Ala Leu Arg Ala Pro Gln Asn Leu Phe Leu Val Ser Leu Ala Ser Ala
                85                  90                  95

Asp Ile Leu Val Ala Thr Leu Val Met Pro Phe Ser Leu Ala Asn Glu
            100                 105                 110

Leu Met Ala Tyr Trp Tyr Phe Gly Gln Val Trp Cys Gly Val Tyr Leu
        115                 120                 125

Ala Leu Asp Val Leu Phe Cys Thr Ser Ser Ile Val His Leu Cys Ala
    130                 135                 140

Ile Ser Leu Asp Arg Tyr Trp Ser Val Thr Gln Ala Val Glu Tyr Asn
145                 150                 155                 160

Leu Lys Arg Thr Pro Arg Arg Val Lys Ala Thr Ile Val Ala Val Trp
                165                 170                 175

Leu Ile Ser Ala Val Ile Ser Phe Pro Pro Leu Val Ser Leu Tyr Arg
            180                 185                 190

Gln Pro Asp Gly Ala Ala Tyr Pro Gln Cys Gly Leu Asn Asp Glu Thr
        195                 200                 205

Trp Tyr Ile Leu Ser Ser Cys Ile Gly Ser Phe Phe Ala Pro Cys Leu
    210                 215                 220

Ile Met Gly Leu Val Tyr Ala Arg Ile Tyr Arg Val Ala Lys Arg Arg
225                 230                 235                 240

Thr Arg Thr Leu Ser Glu Lys Arg Ala Pro Val Gly Pro Asp Gly Ala
                245                 250                 255

Ser Pro Thr Thr Glu Asn Gly Leu Gly Ala Ala Gly Ala Gly Glu
            260                 265                 270

Asn Gly His Cys Ala Pro Pro Ala Asp Val Glu Pro Asp Glu Ser
        275                 280                 285
```

```
Ser Ala Ala Glu Arg Arg Arg Arg Gly Ala Leu Arg Arg Gly
    290                 295                 300
Gly Arg Arg Arg Ala Gly Ala Glu Gly Gly Ala Gly Gly Ala Asp Gly
305                 310                 315                 320
Gln Gly Ala Ala Glu Ser Gly Ala Leu Thr Ala Ser Arg Ser Pro Gly
                325                 330                 335
Pro Gly Gly Arg Leu Ser Arg Ala Ser Ser Arg Ser Val Glu Phe Phe
            340                 345                 350
Leu Ser Arg Arg Arg Ala Arg Ser Ser Val Cys Arg Arg Lys Val
        355                 360                 365
Ala Gln Ala Arg Glu Lys Arg Phe Thr Phe Val Leu Ala Val Val Met
    370                 375                 380
Gly Val Phe Val Leu Cys Trp Phe Pro Phe Phe Phe Ile Tyr Ser Leu
385                 390                 395                 400
Tyr Gly Ile Cys Arg Glu Ala Cys Gln Val Pro Gly Pro Leu Phe Lys
                405                 410                 415
Phe Phe Phe Trp Ile Gly Tyr Cys Asn Ser Ser Leu Asn Pro Val Ile
            420                 425                 430
Tyr Thr Val Phe Asn Gln Asp Phe Arg Pro Ser Phe Lys His Ile Leu
        435                 440                 445
Phe Arg Arg Arg Arg Gly Phe Arg Gln
    450                 455

<210> SEQ ID NO 47
<211> LENGTH: 4
<212> TYPE: PRT
<213> ORGANISM: Homo sapiens

<400> SEQUENCE: 47

Gly Ala Ala Glu
1

<210> SEQ ID NO 48
<211> LENGTH: 27
<212> TYPE: DNA
<213> ORGANISM: Homo sapiens

<400> SEQUENCE: 48
ccaccatcgt cgccgtgtgg ctcatct                                          27

<210> SEQ ID NO 49
<211> LENGTH: 24
<212> TYPE: DNA
<213> ORGANISM: Homo sapiens

<400> SEQUENCE: 49
aggcctcgcg gcagatgccg taca                                             24

<210> SEQ ID NO 50
<211> LENGTH: 20
<212> TYPE: DNA
<213> ORGANISM: Homo sapiens

<400> SEQUENCE: 50
agccggacga gagcagcgca                                                  20

<210> SEQ ID NO 51
<211> LENGTH: 6
<212> TYPE: PRT
<213> ORGANISM: Homo sapiens
```

-continued

<400> SEQUENCE: 51

Arg Arg Gly Gly Arg Arg
1               5

<210> SEQ ID NO 52
<211> LENGTH: 12
<212> TYPE: DNA
<213> ORGANISM: Homo sapiens

<400> SEQUENCE: 52
ccccgccccg gc                                                           12

<210> SEQ ID NO 53
<211> LENGTH: 12
<212> TYPE: DNA
<213> ORGANISM: Homo sapiens

<400> SEQUENCE: 53
ccccgccgac tc                                                           12

<210> SEQ ID NO 54
<211> LENGTH: 69
<212> TYPE: DNA
<213> ORGANISM: Homo sapiens

<400> SEQUENCE: 54
gggcatctcc agaggatgaa gctgaagagg aggaagagga ggaggaggag gaggaagagt       60
gtgaacccc                                                               69

<210> SEQ ID NO 55
<211> LENGTH: 60
<212> TYPE: DNA
<213> ORGANISM: Homo sapiens

<400> SEQUENCE: 55
gggcatctcc agaggatgaa gctgaagagg aggaggagga ggaggaagag tgtgaacccc      60

<210> SEQ ID NO 56
<211> LENGTH: 233
<212> TYPE: PRT
<213> ORGANISM: Homo sapiens

<400> SEQUENCE: 56

Asn Gln Glu Ala Trp Tyr Ile Leu Ala Ser Ser Ile Gly Ser Phe Phe
1               5                   10                  15

Ala Pro Cys Ala Ile Met Ile Leu Val Tyr Leu Arg Ile Tyr Leu Ile
            20                  25                  30

Ala Lys Arg Ser Asn Arg Arg Gly Pro Arg Ala Lys Gly Gly Pro Gly
        35                  40                  45

Gln Gly Glu Ser Lys Gln Pro Arg Pro Asp His Gly Gly Ala Leu Ala
    50                  55                  60

Ser Ala Lys Leu Pro Ala Leu Ala Ser Val Ala Ser Ala Arg Glu Val
65                  70                  75                  80

Asn Gly His Ser Lys Ser Thr Gly Glu Lys Glu Glu Gly Glu Thr Pro
                85                  90                  95

Glu Asp Thr Gly Thr Arg Ala Leu Pro Pro Ser Trp Ala Ala Leu Pro
            100                 105                 110

Asn Ser Gly Gln Gly Gln Lys Glu Gly Val Cys Gly Ala Ser Pro Glu
        115                 120                 125

```
Asp Glu Ala Glu Glu Glu Glu Glu Glu Glu Glu Cys
    130                 135                 140

Glu Pro Gln Ala Val Pro Val Ser Pro Ala Ser Ala Cys Ser Pro Pro
145                 150                 155                 160

Leu Gln Gln Pro Gln Gly Ser Arg Val Leu Ala Thr Leu Arg Gly Gln
                165                 170                 175

Val Leu Leu Gly Arg Gly Val Gly Ala Ile Gly Gly Gln Trp Trp Arg
            180                 185                 190

Arg Arg Ala Gln Leu Thr Arg Glu Lys Arg Phe Thr Phe Val Leu Ala
        195                 200                 205

Val Val Ile Gly Val Phe Val Leu Cys Trp Phe Pro Phe Phe Ser
    210                 215                 220

Tyr Ser Leu Gly Ala Ile Cys Pro Lys
225                 230

<210> SEQ ID NO 57
<211> LENGTH: 15
<212> TYPE: DNA
<213> ORGANISM: Homo sapiens

<400> SEQUENCE: 57
gcccaacggt ctggg                                                15

<210> SEQ ID NO 58
<211> LENGTH: 15
<212> TYPE: DNA
<213> ORGANISM: Homo sapiens

<400> SEQUENCE: 58
gcccaagggt ctggg                                                15

<210> SEQ ID NO 59
<211> LENGTH: 15
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n=a, c, g or t

<400> SEQUENCE: 59
gcccaanggt ctggg                                                15

<210> SEQ ID NO 60
<211> LENGTH: 13
<212> TYPE: PRT
<213> ORGANISM: Homo sapiens

<400> SEQUENCE: 60

Arg Glu Pro Gly Leu Gly Asn Pro Arg Arg Glu Thr Gly
1               5                   10

<210> SEQ ID NO 61
<211> LENGTH: 13
<212> TYPE: PRT
<213> ORGANISM: Homo sapiens

<400> SEQUENCE: 61

Arg Glu Pro Gly Leu Gly Lys Pro Arg Arg Glu Thr Gly
1               5                   10
```

```
<210> SEQ ID NO 62
<211> LENGTH: 13
<212> TYPE: PRT
<213> ORGANISM: Mouse

<400> SEQUENCE: 62

Arg Glu Pro Gly Leu Gly Asn Pro Arg Arg Asp Ala Gly
1               5                   10

<210> SEQ ID NO 63
<211> LENGTH: 13
<212> TYPE: PRT
<213> ORGANISM: Rat

<400> SEQUENCE: 63

Arg Glu Pro Gly Val Ala Asn Pro Arg Arg Asp Ala Gly
1               5                   10

<210> SEQ ID NO 64
<211> LENGTH: 13
<212> TYPE: PRT
<213> ORGANISM: Guinea Pig

<400> SEQUENCE: 64

Arg Glu Leu Gly Leu Gly Asn Pro Arg Arg Glu Ala Gly
1               5                   10

<210> SEQ ID NO 65
<211> LENGTH: 13
<212> TYPE: PRT
<213> ORGANISM: Bos Taurus

<400> SEQUENCE: 65

Arg Glu Pro Gly Leu Gly Asn Pro Arg Arg Glu Ala Ser
1               5                   10

<210> SEQ ID NO 66
<211> LENGTH: 13
<212> TYPE: PRT
<213> ORGANISM: Pig

<400> SEQUENCE: 66

Arg Glu Pro Gly Leu Gly Asn Pro Arg Arg Glu Ala Gly
1               5                   10

<210> SEQ ID NO 67
<211> LENGTH: 29
<212> TYPE: DNA
<213> ORGANISM: Homo sapiens

<400> SEQUENCE: 67
acgggcaggg ggcggggccg ggggcggct                                    29

<210> SEQ ID NO 68
<211> LENGTH: 17
<212> TYPE: DNA
<213> ORGANISM: Homo sapiens

<400> SEQUENCE: 68
acgggcaggg ggcggct                                                 17

<210> SEQ ID NO 69
<211> LENGTH: 206
<212> TYPE: PRT
<213> ORGANISM: Homo sapiens
```

```
<400> SEQUENCE: 69

Asn Asp Glu Thr Trp Tyr Ile Leu Ser Ser Cys Ile Gly Ser Phe Phe
1               5                   10                  15

Ala Pro Cys Leu Ile Met Gly Leu Val Tyr Ala Arg Ile Tyr Arg Val
            20                  25                  30

Ala Lys Arg Arg Thr Arg Thr Leu Ser Glu Lys Arg Ala Pro Val Gly
            35                  40                  45

Pro Asp Gly Ala Ser Pro Thr Thr Glu Asn Gly Leu Gly Ala Ala Ala
        50                  55                  60

Gly Ala Gly Glu Asn Gly His Cys Ala Pro Pro Ala Asp Val Glu
65                  70                  75                  80

Pro Asp Glu Ser Ser Ala Ala Ala Glu Arg Arg Arg Arg Arg Gly Ala
                85                  90                  95

Leu Arg Arg Gly Gly Arg Arg Arg Ala Gly Ala Glu Gly Gly Ala Gly
                100                 105                 110

Gly Ala Asp Gly Gln Gly Ala Gly Pro Gly Ala Ala Glu Ser Gly Ala
            115                 120                 125

Leu Thr Ala Ser Arg Ser Pro Gly Pro Gly Gly Arg Leu Ser Arg Ala
        130                 135                 140

Ser Ser Arg Ser Val Glu Phe Phe Leu Ser Arg Arg Arg Arg Ala Arg
145                 150                 155                 160

Ser Ser Val Cys Arg Arg Lys Val Ala Gln Ala Arg Glu Lys Arg Phe
                165                 170                 175

Thr Phe Val Leu Ala Val Val Met Gly Val Phe Val Leu Cys Trp Phe
            180                 185                 190

Pro Phe Phe Phe Ile Tyr Ser Leu Tyr Gly Ile Cys Arg Glu
            195                 200                 205
```